(12) United States Patent
Daugherty et al.

(10) Patent No.: US 9,234,847 B2
(45) Date of Patent: *Jan. 12, 2016

(54) CELLULAR LIBRARIES OF PEPTIDE SEQUENCES (CLIPS) AND METHODS OF USING THE SAME

(75) Inventors: Patrick Sean Daugherty, Santa Barbara, CA (US); Kevin Todd Boulware, Santa Barbara, CA (US)

(73) Assignee: The Regents of the University of California, Oakland, CA (US)

(*) Notice: Subject to any disclaimer, the term of this patent is extended or adjusted under 35 U.S.C. 154(b) by 495 days.

This patent is subject to a terminal disclaimer.

(21) Appl. No.: 12/646,323

(22) Filed: Dec. 23, 2009

(65) Prior Publication Data

US 2010/0173349 A1    Jul. 8, 2010

Related U.S. Application Data

(63) Continuation of application No. 11/514,377, filed on Aug. 30, 2006, now Pat. No. 7,666,817.

(60) Provisional application No. 60/712,434, filed on Aug. 31, 2005.

(51) Int. Cl.
  *G01N 21/64* (2006.01)
  *C12N 15/10* (2006.01)
  *C40B 40/02* (2006.01)

(52) U.S. Cl.
  CPC ........ *G01N 21/6486* (2013.01); *C12N 15/1037* (2013.01); *C12N 15/1044* (2013.01); *C40B 40/02* (2013.01)

(58) Field of Classification Search
  None
  See application file for complete search history.

(56) References Cited

U.S. PATENT DOCUMENTS

| | | |
|---|---|---|
| 5,571,698 A | 11/1996 | Ladner et al. |
| 5,962,255 A | 10/1999 | Griffiths et al. |
| 5,990,275 A | 11/1999 | Whitlow et al. |
| 6,300,065 B1 | 10/2001 | Kieke et al. |
| 6,303,344 B1 | 10/2001 | Patten et al. |
| 6,423,538 B1 | 7/2002 | Wittrup et al. |
| 6,492,160 B1 | 12/2002 | Griffiths et al. |

(Continued)

FOREIGN PATENT DOCUMENTS

| | | |
|---|---|---|
| EP | 0474891 | 3/1992 |
| EP | 0474894 | 3/1992 |

(Continued)

OTHER PUBLICATIONS

Eisenstein, M. (2006) "Sorting Out the Best Targets." Nature Methods, 3(7):498.

(Continued)

*Primary Examiner* — Tracy Vivlemore
*Assistant Examiner* — Karen S Weiler
(74) *Attorney, Agent, or Firm* — Michael B. Rubin; Bozicevic, Field & Francis LLP

(57) ABSTRACT

The present invention provides compositions including peptide display scaffolds that present at least one candidate peptide and at least one detectable moiety in at least one of the N-terminal and C-terminal candidate peptide presenting domains that when expressed in a cell are accessible at a surface of the cell outermembrane. In addition, the present invention also provides kits and methods for screening a library of cells presenting the candidate peptides in peptide display scaffolds to identify a ligand for an enzyme.

25 Claims, 17 Drawing Sheets

(56) References Cited

U.S. PATENT DOCUMENTS

| | | | |
|---|---|---|---|
| 6,548,249 | B1 | 4/2003 | Anderson et al. |
| 6,660,257 | B1 | 12/2003 | McWherter et al. |
| 6,660,843 | B1 | 12/2003 | Feige et al. |
| 6,696,251 | B1 | 2/2004 | Wittrup et al. |
| 6,699,658 | B1 | 3/2004 | Wittrup et al. |
| 6,723,512 | B2 | 4/2004 | Larocca et al. |
| 7,256,038 | B2 | 8/2007 | Daugherty et al. |
| 7,612,019 | B2 | 11/2009 | Daugherty et al. |
| 7,666,817 | B2 | 2/2010 | Daugherty et al. |
| 8,293,685 | B2 | 10/2012 | Daugherty et al. |
| 2003/0013150 | A1 | 1/2003 | Manosroi et al. |
| 2003/0049729 | A1 | 3/2003 | Manosroi et al. |
| 2003/0082575 | A1 | 5/2003 | Schultz et al. |
| 2004/0146976 | A1 | 7/2004 | Wittrup et al. |
| 2005/0047461 | A1 | 3/2005 | Kihara et al. |
| 2005/0196406 | A1 | 9/2005 | Daugherty et al. |
| 2006/0003387 | A1 | 1/2006 | Peelle et al. |
| 2006/0029947 | A1 | 2/2006 | Georgiou et al. |
| 2007/0020678 | A1 | 1/2007 | Ault-Riche et al. |
| 2007/0065878 | A1 | 3/2007 | Daugherty et al. |
| 2009/0035317 | A1 | 2/2009 | Daugherty et al. |
| 2009/0062142 | A1 | 3/2009 | Daugherty et al. |
| 2010/0113303 | A1 | 5/2010 | Daugherty et al. |

FOREIGN PATENT DOCUMENTS

| | | |
|---|---|---|
| EP | 0922957 | 6/1999 |
| WO | WO 9817810 | 4/1998 |
| WO | WO2005047461 | 5/2005 |
| WO | WO 2005047461 | 5/2005 |

OTHER PUBLICATIONS

EPO Search Report: EP Supplementary Partial EPO Search Report for EP 04816813.2 dated Nov. 2, 2006; EPO Form 1507.2.

EPO Search Report: Supplementary EPO Search Report for EP 04816813.2 dated Jan. 30, 2007; EPO Form 1507.2.

Lee, et al. (2003) "Microbial Cell-Surface Display" Trends in Biotechnology, 21(1):46-52.

Roberts, et al. (1996) "Affinity Maturation of Proteins Displayed on Surface of M13 Bacteriophage as Major Coat Protein Fusions" Methods Enzymol., 267:68-82.

Taschner, et al. (2002) "Selection of Peptide Entry Motifs by Bacterial Surface Display," Biochem. J., 367:393-402.

Ahmed, et al. (2006) "Vascular Endothelial Growth Factor (VEGF) Inhibition by Small Molecules" J. Chemother. 16(Suppl. 4):59-63.

Beebe, et al. (2003) "Pharmacological Characterization of CP-547,632, a Novel Vascular Endothelial Growth Factor Receptor-2 Tyrosine Kinase Inhibitor for Cancer Therapy" Cancer Res. 63(21):7301-7309.

Bergsland, et al. (2004) "Vascular Endothelial Growth Factor as a Therapeutic Target in Cancer" Am. J. Health Syst. Pharm. 61(21 Suppl. 5):S4-S11.

Boder, et al. (1997) "Yeast Surface Display for Screening Combinational Polypeptide Libraries" Nat. Biotechnol. 15(6):553-557.

Boder, et al. (1998) "Optimal Screening of Surface-Displayed Polypeptide Libraries" Biotechnol. Prog. 14(1):55-62.

Boder, et al. (2000) "Directed Evolution of Antibody Fragments with Monovalent Femtomolar Antigen-Binding Affinity" PNAS USA 97(20):10701-10705.

Bos, et al. (2004) "Biogenesis of the Gram-Negative Bacterial Outer Membrane" Annu. Rev. Microbiol. 61:191-214.

Bupp, et al. (2002) "Altering Retroviral Tropism Using a Random-Display Envelope Library" Mol. Ther. 5(3):329-335.

Caponigro, et al. (2005) "New Drugs in Cancer Therapy, National Tumor Institute, Naples, Jun. 17-18, 2004" Anticancer Drugs 16(2):211-221.

Charbit, et al. (1986) "Probing the Topology of a Bacterial Membrane Protein by Genetic Insertion of a Foreign Epitope: Expression at the Cell Surface" EMBO J 5(11):3029-3037.

Christmann, et al. (1999) "The Cystine Knot of a Squash-Type Protease Inhibitor as a Structural Scaffold for Escherichia Coli Cell Surface Display of Conformationally Constrained Peptides" Protein Eng 12(9):797-806.

Ciafré, et al. (2004) "An Anti-VEGF Ribozyme Embedded within the Adenoviral VAI Sequence Inhibits Glioblastoma Cell Angiogenic Potential in Vitro" J. Vasc. Res. 41(3):220-228.

Dane, et al. (2006) "Isolation of Cell Specific Peptide Ligands Using Fluorescent Bacterial Display Libraries" J. Immunol. Methods 309(1-2):120-129.

Daugherty, et al. (2000) "Quantitative Analysis of the Effect of the Mutation Frequency on the Affinity Maturation of Single Chain Fv Antibodies" PNAS USA 97(5):2029-2034.

Feldhaus, et al. (2003) "Flow-Cytometric Isolation of Human Antibodies From A Nonimmune Saccharomyces Cerevisiae Surface Display Library" Nat. Biotechnol. 21(2):163-170.

Fields, et al. (1994) "The Two-Hybrid System: An Assay for Protein-Protein Interactions" Trends in Genetics 10(8):286-292.

Francisco, et al. (1992) "Transport and Anchoring of Beta Lactamase to the External Surface of Escherichia Coli" PNAS USA 89(7):2713-2717.

Gao, et al. (2002) "Down-Regulation of Vascular Endothelial Growth Factor and Up-Regulation of Pigment Epithelium-Derived Factor: A Possible Mechanism for the Anti-Angiogenic Activity of Plasminogen Kringle 5" J. Biol. Chem. 277(11):9492-9497.

Garrett, et al. (2003) "Effect of Linker Sequence on the Stability of Circularly Permuted Variants of Ribonuclease T1" Bioorg. Chem. 31(5):412-424.

Georgiou (2000) "Analysis of Large Libraries of Protein Mutants Using Flow Cytometry" Adv. Protein Chem. 55:293-315.

Georgiou, et al. (1997) "Display of Heterologous Proteins on the Surface of Microorganisms: From the Screening of Combinatorial Libraries to Live Recombinant Vaccines" Nat. Biotechnol. 15(1):29-34.

Giebel, et al. (1995) "Screening of Cyclic Peptide Phage Libraries Identifies Ligands That Bind Streptavidin with High Affinities" Biochemistry 34(47):15430-15435.

Hanes, et al. (1997) "In Vitro Selection and Evolution of Functional Proteins by Using Ribosome Display" PNAS USA 94(10):4937-4942.

Heinemann, et al. (1995) "Circular Permutation of Polypeptide Chains: Implications for Protein Folding and Stability" Prog Biophys Mol Biol. 64:121-143.

James, et al. (2003) "Antibody Multispecificity Media Ted by Conformational Diversity" Science 299:1362-1367.

Jung, et al. (1998) "Surface Display of Zymomonas Mobilis Levansucrase by Using the Ice-nucleation Protein of Pseudomonas Syringae" Nat Biotechnol. 16(6):576-580.

Kim, et al. (2000) "Isolation of Peptide Ligands That Inhibit Glutamate Racemase Activity from a Random Phage Display Library" J Biomol. Screen. 5(6):435-440.

Kjaergaard, et al. (2001) "Novel Zn(2+)-Chelating Peptides Selected from a Fimbria-Displayed Random Peptide Library" Appl Environ Microbiol. 67(12):5467-5473.

Kodadek (2001) "Protein Microarrays: Prospects and Problems" Chem. Biol. 8(2):105-115.

Konner & Dupont (2004) "Use of Soluble Recombinant Decoy Receptor Vascular Endothelial Growth Factor Trap (VEGF Trap) to Inhibit Vascular Endothelial Growth Factor Activity" Clin. Colorectal. Cancer 4 Suppl. 2:S81-S85.

Lu, et al. (1995) "Expression of Thioredoxin Random Peptide Libraries on the Escherichia Coli Cell Surface as Functional Fusions to Flagellin: A System Designed for Exploring Protein-Protein Interactions" Biotechnology 13(4):366-372.

Maurer, et al. (1997) "Autodisplay: One-Component System for Efficient Surface Display and Release of Soluble Recombinant Proteins from Escherichia Coli" J. Bacteriol. 179(3):794-804.

Morimoto, et al. (2004) "Gene Expression Profiling of Human Colon Xenograft Tumors Following Treatment with SU11248, a Multitargeted Tyrosine Kinase Inhibitor" Oncogene 23(8):1618-1626.

(56) References Cited

OTHER PUBLICATIONS

Müller, et al. (2003) "Random Peptide Libraries Displayed on Adeno-Associated Virus to Select for Targeted Gene Therapy Vectors" *Nat Biotechnol.* 21(9):1040-1046.

Nakajima, et al. (2000) "Expression of Random Peptide Fused to Invasin on Bacterial Cell Surface for Selection of Cell Targeting Peptides" *Gene* 260(1-2):121-131.

Nguyen, et al. (2005) "Evolutionary Optimization of Fluorescent Proteins for Intracellular FRET" *Nat Biotechnol.* 23(3):355-360.

Olsen, et al. (2003) "High-Throughput Facs Method for Directed Evolution of Substrate Specificity" *Methods Mol. Biol.* 230:329-342.

Pasqualini & Ruoslahti (1996) "Organ Targeting in Vivo Using Phage Display Peptide Libraries" *Nature* 380(67572):364-366.

Pautsch & Schulz (2000) "High-Resolution Structure of the OmpA Membrane Domain" *J. Mol. Biol.* 298(2):273-282.

Poul, et al. (2000) "Selection of Tumor Specific Internalizing Human Antibodies from Phage Libraries" *J Mol Biol.* 301(5):1149-1161.

Proba, et al. (1998) "Antibody scFv Fragments without Disulfide Bonds Made by Molecular Evolution" *J. Mol. Biol.* 275(2):245-253.

Riedel, et al. (2005) "Antiangiogenic Therapy of Head and Neck Squamous Cell Carcinoma by Vascular Endothelial Growth Factor Antisense Therapy" *Adv. Otorhinolaryngol.* 62:103-120.

Shusta, et al. (1999) "Biosynthetic Polypeptide Libraries" *Curr Opin Biotechnol.* 10(2):117-122.

Smith (1985) "Filamentous Fusion Phage: Novel Expression Vectors That Display Cloned Antigens on the Virion Surface" *Science* 228(4705):1315-1317.

Susman (2005) "Bevacizumab Adds Survival Benefit in Colorectal Cancer" *Lancet Oncol.* 6:136.

Tuccillo, et al. (2005) "Antitumor Activity of ZD6474, a Vascular Endothelial Growth Factor-2 and Epidermal Growth Factor Receptor Small Molecule Tyrosine Kinase Inhibitor, in Combination with SC-236, A Cyclooxygenase-2 Inhibitor" *Clin. Cancer Res.* 11(3):1268-1276.

Wentzel, et al. (2001) "Display of Passenger Proteins on the Surface of *Escherichia Coli* K-12 by the Enterohemorrhagic *E. coli* Intimin EaeA" *J. Bacteriol.* 183(24):7272-7284.

Whaley, et al. (2000) "Selection of Peptides with Semiconductor Binding Specificity for Directed Nanocrystal Assembly" *Nature* 405(6787):665-668.

Wild, et al. (2000) "Inhibition of Angiogenesis and Tumor Growth by VEGF121 Toxin Conjugate: Differential Effect on Proliferating Endothelial Cells" *Br. J. Cancer* 83(8):1077-1083.

Wilson, et al. (2001) "The Use of mRNA Display to Select High-Affinity Protein-Binding Peptides" *PNAS USA* 98(7):3750-3755.

Wittrup (2001) "Protein Engineering by Cell-Surface Display" *Curr. Opin. Biotechnol.* 12(4):395-399.

Yang, et al. (1995) "CDR Walking Mutagenesis for the Affinity Maturation of a Potent Human Anti-HIV-1 Antibody into the Picomolar Range" *J Mol. Biol.* 254(3):392-403.

Yonezawa, et al. (2003) "DNA Display for In Vitro Selection of Diverse Peptide Libraries" *Nucleic Acids Research* 31:e118.

Bos & Tommassen (2004) "Biogenesis of the Gram-negative bacterial outer membrane" Curr Opin Microbiol 7 (6):610-616.

Ascheim, et al., Clipping away at protease substrates, Nature Biothnology, 2006, vol. 24, No. 6, pp. 665.

Bessette, et al., Rapid isolation of high-affinity protein binding peptides using bacterial display, Protein Engineering, Design and Selection (2004) 17 (10): 731-739.

Bessette, et al., Flow Cytometric Screening of cDNA Expression Libraries for Fluorescent Proteins, Biotechnology Progress, vol. 20, Issue 3, pp. 963-967, 2004.

Boulware, et al., Protease specificity determination by using cellular libraries of peptide substrates (CLiPS)., Proc Natl Acad Sci U S A. May 16, 2006;103(20):7583-7588.

Camaj, et al., Ligand-mediated protection against phage lysis as a positive selection strategy for the enrichment of epitopes displayed on the surface of *E. coli* cells, Biol Chem. Dec. 2001;382(12):1669-1677.

Choo, et al., Designing DNA-binding proteins on the surface of filamentous phage., Current Opinion in Biotechnology vol. 6, Issue 4, 1995, pp. 431-436.

Daugherty, et al., Protein engineering with bacterial display, Curr Opin Struct Biol. Aug. 2007;17(4):474-480.

Daugherty, et al., Sorting out the best targets., Nature Methods 3, No. 7, p. 498 (2006).

Daugherty, et al., Flow cytometric screening of cell-based libraries., Journal of Immunological Methods vol. 243, Issues 1-2, Sep. 21, 2000, pp. 211-227.

Daugherty, et al., Development of an optimized expression system for the screening of antibody libraries displayed on the *Escherichia coli* surface., Protein Eng. (1999) 12 (7): 613-621.

Deperthes, D, Phage display substrate: a blind method for determining protease specificity., Biol Chem. Jul.-Aug. 2002;383(7-8):1107-1112.

Etz, et al., Bacterial phage receptors, versatile tools for display of polypeptides on the cell surface, Journal of Bacteriology, Dec. 2001, p. 6924-6935, vol. 183, No. 23.

Fernandez, et al., Solution NMR studies of the integral membrane proteins OmpX and OmpA from *Escherichia coli*, FEBS Lett. Aug. 31, 2001;504(3):173-178.

Freudl, Insertion of peptides into cell-surface-exposed areas of the *Escherichia coli* OmpA protein does not interfere with export and membrane assembly, Gene. Oct. 30, 1989;82(2):229-236.

Graf, et. al., Random circular permutation of genes and expressed polypeptide chains: application of the method to the catalytic chains of aspartate transcarbamoylase, Proc Natl Acad Sci U S A. Oct. 15, 1996;93(21):11591-11596.

Hoogenboom, H.R., Designing and optimizing library selection strategies for generating high-affinity antibodies., Trends in Biotechnology, vol. 15, Issue 2, Feb. 1997, pp. 62-70.

Koebnik, Membrane assembly of the *Escherichia coli* outer membrane protein OmpA: exploring sequence constraints on transmembrane beta-strands, J Mol Biol. Jan. 29, 1999;285(4):1801-1810.

Koebnik, et. al., Membrane assembly of circularly permuted variants of the *E. coli* outer membrane protein OmpA, J Mol Biol. Jul. 28, 1995;250(5):617-626.

Koebnik, et al.,Structural and functional roles of the surface-exposed loops of the beta-barrel membrane protein OmpA from *Escherichia coli*, Journal of Bacteriology, Jun. 1999, p. 3688-3694, vol. 181, No. 12.

Koebnik, et al. Structure and function of bacterial outer membrane proteins:barrels in a nutshell, Molecular Microbiology, (2000), 37(2), 239-253.

Ladner, R., Constrained peptides as binding entities.,Trends in Biotechnology, vol. 13, Issue 10, Oct. 1995, pp. 426-430.

Lowman., et al., Selecting high-affinity binding proteins by monovalent phage display., Biochemistry. Nov. 12, 1991;30(45):10832-10838.

Ley., et al., Obtaining a family of high-affinity, high-specificity protein inhibitors of plasmin and plasma kallikrein., Molecular Diversity,vol. 2, Nos. 1-2, 119-124, Oct. 1996.

MacIntyre, et al., The signal sequence of an *Escherichia coli* outer membrane protein can mediate translocation of a not normally secreted protein across the plasma membrane, J. Biol. Chem., vol. 262, Issue 17, 8416-8422, 06, 1987.

Markland, et al., Selection for protease inhibitors using bacteriophage display., Methods in Enzymology,vol. 267, 1996, pp. 28-51.

Markland, et al., Iterative Optimization of High-Affinity Protease Inhibitors Using Phage Display. 2. Plasma Kallikrein and Thrombin., Biochemistry, 1996, 35 (24), pp. 8058-8067.

Markland, et al., Iterative Optimization of High-Affinity Protease Inhibitors Using Phage Display. 1. Plasmin., Biochemistry, 1996, 35 (24), pp. 8045-8057.

Markland, et al., Affinity maturation of proteins displayed on surface of M13 bacteriophage as major coat protein fusions., Methods in Enzymology, vol. 267, 1996, pp. 68-82.

Markland, et al., Selection for protease inhibitors using bacteriophage display., Methods in Enzymology vol. 267, 1996, pp. 28-51.

(56) References Cited

OTHER PUBLICATIONS

Matthews, et al., Substrate phage: selection of protease substrates by monovalent phage display., Science May 21, 1993: vol. 260. No. 5111, pp. 1113-1117.

Mejare, et al., Selection of cadmium specific hexapeptides and their expression as OmpA fusion proteins in *Escherichia coli*, Protein Engineering, vol. 11, 489-494.

Rice, et al. Bacterial display using circularly permuted outer membrane protein OmpX yields high affinity peptide ligands, Protein Sci. Apr. 2006; 15(4): 825-836.

Rice, et al., Directed evolution of a biterminal bacterial display scaffold enhances the display of diverse peptides, Protein Eng Des Sel. Jul. 2008;21(7):435-442.

Takahara, et al., The ompA signal peptide directed secretion of *Staphylococcal nuclease* A by *Escherichia coli*,J. Biol. Chem., vol. 260, Issue 5, 2670-2674, 03, 1985.

Vogt, et al. The structure of the outer membrane protein OmpX from *Escherichia coli* reveals possible mechanisms of virulence, Structure (London), vol. 7, Issue 10, Oct. 15, 1999, pp. 1301-1309.

Wang, et al., Phage display of proteases and macromolecular inhibitors., Methods in Enzymology vol. 267, 1996, pp. 52-68.

Boulware, et al., Protease specificity determination by using cellular libraries of peptide substrates (CLiPS), PNAS May 16, 2006 vol. 103 No. 20 7583-7588.

Beutler, et al. (2000) "Folding and Activity of Circularly Permuted Forms of a Polytopic Membrane Protein" Proc. Natl. Acad. Sci. USA 97(4):1477-1482.

Baird, et al. (1999) "Circular Permutation and Receptor Insertion within Green Fluorescent Proteins" Proc. Natl. Acad. Sci. U.S.A. 96(20):11241-11246.

Cunningham, et al. (1979) "Favin versus Concanavalin A: Circularly Permuted Amino Acid Sequences" Proc. Natl. Acad. Sci. U.S.A. 76(7):3218-3222.

Francisco, et al. (1993) "Production and Fluoresence-Activated Cell Sorting of *Escherichia coli* Expressing a Functional Antibody Fragment Antibody Fragment on the External Surface" Proc. Natl. Acad. Sci. U.S.A. 90(22):10444-10448.

Goldenberg & Creighton (1983) "Circular and Circularly Permuted Forms of Bovine Pancreatic Trypsin Inhibitor" J. Mol. Biol. 165(2):407-413.

Ståhl & Uhlén (1997) "Bacterial Surface Display: Trends and Progress" Trends Biotechnol. 15(5):185-192.

Yu & Lutz (2011) "Circular Permutation: A Different Way to Engineer Enzyme Structure and Function" Trends Biotechnol. 29(1):18-25.

U.S. Appl. No. 13/615,072, filed Sep. 13, 2012, Daugherty, et al.

U.S. Appl. No. 13/631,206, filed Sep. 28, 2012, Daugherty, et al.

U.S. Appl. No. 13/722,915, filed Dec. 20, 2012, Daugherty, et al.

FIG. 5
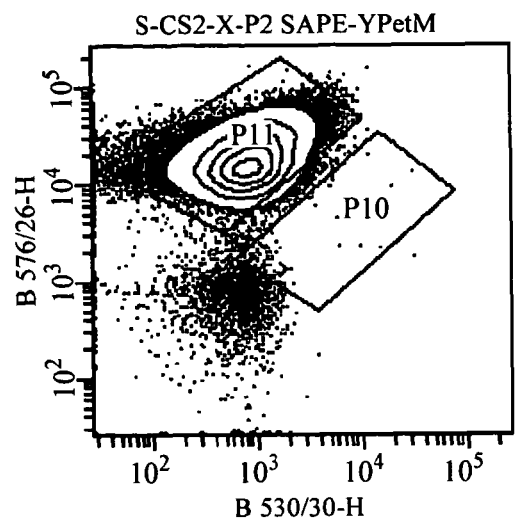
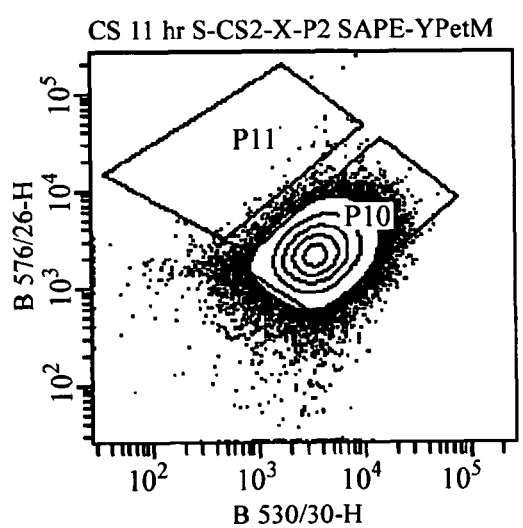

DNA sequence of OmpX with N- and C-terminal Detectable Moieties

```
  1    ATGAAAAAAA TTGCATGTCT TTCAGCACTG GCCGCAGTTC TGGCTTTCAC
 51    CGCAGGTACT TCCGTAGCTG GCCAGTCTGG CCAGTGGGTG TGCCACCCGA
101    TGTGGGAGGT GATGTGCCTG AGGGGAGGGT CTGGTCAAAG TGCCTCCGGC
151    CAATCCNNSN NSNNSNNSNN STCTCAATCT GCGGGAGGGC AGTCTGGGCA
201    GTCTGGTGAC TACAACAAAA ACCAGTACTA CGGCATCACT GCTGGTCCGG
251    CTTACCGCAT TAACGACTGG GCAAGCATCT ACGGTGTAGT GGGTGTGGGT
301    TATGGTAAAT TCCAGACCAC TGAATACCCG ACCTACAAAC ACGACACCAG
351    CGACTACGGT TTCTCCTACG GTGCGGGTCT GCAGTTCAAC CCGATGGAAA
401    ACGTTGCTCT GGACTTCTCT TACGAGCAGA GCCGTATTCG TAGCGTTGAC
451    GTAGGCACCT GGATTGCCGG TGTTGGTTAC CGCTTCGGAG GAAGCGGAGC
501    GACTTCTACT GTAACTGGCG GTTACGCACA GAGCGACGCT CAGGGCCAAA
551    TGAACAAAAT GGGCGGTTTC AACCTGAAAT ACCGCTATGA AGAAGACAAC
601    AGCCCGCTGG GTGTGATCGG TTCTTTCACT TACACCGAGA AAAGCCGTAC
651    TGCAAGCGGA GGTCAGTCCG GTCAGCCAGC TCCTTCGATA GACAGAAGCA
701    CGAAACCCCC ACTGTAA
```

FIG. 14

Amino Acid Sequences of OmpX with N- and C- Terminal Detectable Moieties

```
1    MKKIACLSAL AAVLAFTAGT SVAGQSGQWV CHPMWEVMCL RGGSGQSASG
51   QSXXXXXSQS AGGQSGQSGD YNKNQYYGIT AGPAYRINDW ASIYGVVGVG
101  YGKFQTTEYP TYKHDTSDYG FSYGAGLQFN PMENVALDFS YEQSRIRSVD
151  VGTWIAGVGY RFGGSGATST VTGGYAQSDA QGQMNKMGGF NLKYRYEEDN
201  SPLGVIGSFT YTEKSRTASG GQSGQPAPSI DRSTKPPL*
```

```
1    GQSGQWVCHP MWEVMCLRGG SGQSASGQSX XXXXSQSAGG QSGQSGDYNK
51   NQYYGITAGP AYRINDWASI YGVVGVGYGK FQTTEYPTYK HDTSDYGFSY
101  GAGLQFNPME NVALDFSYEQ SRIRSVDVGT WIAGVGYRFG GSGATSTVTG
151  GYAQSDAQGQ MNKMGGFNLK YRYEEDNSPL GVIGSFTYTE KSRTASGGQS
201  GQPAPSIDRS TKPPL*
```

FIG. 15

DNA Sequence of OmpX with an N-terminal Detectable Moiety

```
  1    atgaaaaaaa ttgcatgtct ttcagcactg gccgcagttc tggctttcac
 51    cgcaggtact tccgtagctg gccagtctgg ccagtgggtg tgccacccga
101    tgtgggaggt gatgtcctg aggggagggt ctnnsnnsnn snnsnnsnns
151    ggagggcagt ctgggcagtc tggtgactac aacaaaaacc agtactacgg
201    catcactgct ggtccggctt accgcattaa cgactgggca agcatctacg
251    gtgtagtggg tgtgggttat ggtaaattcc agaccactga atacccgacc
301    tacaaacacg acaccagcga ctacggtttc tcctacggtg cgggtctgca
351    gttcaacccg atggaaaacg ttgctctgga cttctcttac gagcagagcc
401    gtattcgtag cgttgacgta ggcacctgga ttgccggtgt tggttaccgc
451    ttcggaggaa gcggagcgac ttctactgta actggcggtt acgcacagag
501    cgacgctcag ggccaaatga acaaaatggg cggtttcaac ctgaaatacc
551    gctatgaaga agacaacagc ccgctgggtg tgatcggttc tttcacttac
601    accgagaaaa gccgtactgc aagctaa
```

FIG. 16

Amino Acid Sequences of OmpX with an N-terminal Detectable Moiety

```
1    MKKIACLSAL AAVLAFTAGT SVAGQSGQWV CHPMWEVMCL RGGSXXXXXX
51   GGQSGQSGDY NKNQYYGITA GPAYRINDWA SIYGVVGVGY GKFQTTEYPT
101  YKHDTSDYGF SYGAGLQFNP MENVALDFSY EQSRIRSVDV GTWIAGVGYR
151  FGGSGATSTV TGGYAQSDAQ GQMNKMGGFN LKYRYEEDNS PLGVIGSFTY
201  TEKSRTAS*
```

```
1    GQSGQWVCHP MWEVMCLRGG SXXXXXXGGQ SGQSGDYNKN QYYGITAGPA
51   YRINDWASIY GVVGVGYGKF QTTEYPTYKH DTSDYGFSYG AGLQFNPMEN
101  VALDFSYEQS RIRSVDVGTW IAGVGYRFGG SGATSTVTGG YAQSDAQGQM
151  NKMGGFNLKY RYEEDNSPLG VIGSFTYTEK SRTAS*
```

FIG. 17

SEQUENCE LISTING

<160> NUMBER OF SEQ ID NOS: 170

<210> SEQ ID NO 1
<211> LENGTH: 6
<212> TYPE: PRT
<213> ORGANISM: Artificial Sequence
<220> FEATURE:

<223> OTHER INFORMATION: synthetic peptide

<400> SEQUENCE: 1

Gly Gly Ser Gly Gly Ser
1               5

<210> SEQ ID NO 2
<211> LENGTH: 5
<212> TYPE: PRT
<213> ORGANISM: Artificial Sequence
<220> FEATURE:
<223> OTHER INFORMATION: synthetic peptide

<400> SEQUENCE: 2

Asp Asp Asp Asp Lys
1               5

<210> SEQ ID NO 3
<211> LENGTH: 6
<212> TYPE: PRT
<213> ORGANISM: Artificial Sequence
<220> FEATURE:
<223> OTHER INFORMATION: synthetic peptide

<400> SEQUENCE: 3

Val Asp Tyr Arg Phe Leu
1               5

<210> SEQ ID NO 4
<211> LENGTH: 6
<212> TYPE: PRT
<213> ORGANISM: Artificial Sequence
<220> FEATURE:
<223> OTHER INFORMATION: synthetic peptide

<400> SEQUENCE: 4

Ser Gly Asp Arg Met Trp
1               5

<210> SEQ ID NO 5
<211> LENGTH: 6
<212> TYPE: PRT
<213> ORGANISM: Artificial Sequence
<220> FEATURE:
<223> OTHER INFORMATION: synthetic peptide

<400> SEQUENCE: 5

Ser Gly Glu Arg Met Met
1               5

<210> SEQ ID NO 6
<211> LENGTH: 7
<212> TYPE: PRT
<213> ORGANISM: Artificial Sequence
<220> FEATURE:
<223> OTHER INFORMATION: synthetic peptide

<400> SEQUENCE: 6

Glu Asn Leu Tyr Phe Gln Ser
1               5

<210> SEQ ID NO 7
<211> LENGTH: 5
<212> TYPE: PRT
<213> ORGANISM: Artificial Sequence
<220> FEATURE:
<223> OTHER INFORMATION: synthetic peptide

<400> SEQUENCE: 7

Pro Glu Val Ile Tyr
1               5

<210> SEQ ID NO 8
<211> LENGTH: 717
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 157, 158, 160, 161, 163, 164, 166, 167, 169, 170
<223> OTHER INFORMATION: n = A,T,C or G

<400> SEQUENCE: 8

```
atgaaaaaaa ttgcatgtct ttcagcactg gccgcagttc tggctttcac cgcaggtact   60
tccgtagctg gccagtctgg ccagtgggtg tgccacccga tgtgggaggt gatgtgcctg  120
aggggagggt ctggtcaaag tgcctccggc caatccnnsn nsnnsnnsnn stctcaatct  180
gcgggagggc agtctgggca gtctggtgac tacaacaaaa accagtacta cggcatcact  240
gctggtccgg cttaccgcat taacgactgg gcaagcatct acggtgtagt gggtgtgggt  300
tatggtaaat tccagaccac tgaatacccg acctacaaac acgacaccag cgactacggt  360
ttctcctacg gtgcgggtct gcagttcaac ccgatggaaa acgttgctct ggacttctct  420
tacgagcaga gccgtattcg tagcgttgac gtaggcacct ggattgccgg tgttggttac  480
cgcttcggag gaagcggagc gacttctact gtaactggcg gttacgcaca gagcgacgct  540
cagggccaaa tgaacaaaat gggcggtttc aacctgaaat accgctatga agaagacaac  600
agcccgctgg gtgtgatcgg ttctttcact tacaccgaga aaagccgtac tgcaagcgga  660
ggtcagtccg gtcagccagc tccttcgata gacagaagca cgaaaccccc actgtaa    717
```

<210> SEQ ID NO 9
<211> LENGTH: 238
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 53, 54, 55, 56, 57
<223> OTHER INFORMATION: Xaa = Any Amino Acid

<400> SEQUENCE: 9

Met Lys Lys Ile Ala Cys Leu Ser Ala Leu Ala Ala Val Leu Ala Phe
1               5                   10                  15

Thr Ala Gly Thr Ser Val Ala Gly Gln Ser Gly Gln Trp Val Cys His
            20                  25                  30

Pro Met Trp Glu Val Met Cys Leu Arg Gly Gly Ser Gly Gln Ser Ala
        35                  40                  45

Ser Gly Gln Ser Xaa Xaa Xaa Xaa Xaa Ser Gln Ser Ala Gly Gly Gln
    50                  55                  60

Ser Gly Gln Ser Gly Asp Tyr Asn Lys Asn Gln Tyr Tyr Gly Ile Thr
65                  70                  75                  80

Ala Gly Pro Ala Tyr Arg Ile Asn Asp Trp Ala Ser Ile Tyr Gly Val
                85                  90                  95

Val Gly Val Gly Tyr Gly Lys Phe Gln Thr Thr Glu Tyr Pro Thr Tyr
            100                 105                 110

```
Lys His Asp Thr Ser Asp Tyr Gly Phe Ser Tyr Ala Gly Leu Gln
            115                 120                 125

Phe Asn Pro Met Glu Asn Val Ala Leu Asp Phe Ser Tyr Glu Gln Ser
130                 135                 140

Arg Ile Arg Ser Val Asp Val Gly Thr Trp Ile Ala Gly Val Gly Tyr
145                 150                 155                 160

Arg Phe Gly Gly Ser Gly Ala Thr Ser Thr Val Thr Gly Gly Tyr Ala
                165                 170                 175

Gln Ser Asp Ala Gln Gly Gln Met Asn Lys Met Gly Gly Phe Asn Leu
            180                 185                 190

Lys Tyr Arg Tyr Glu Glu Asp Asn Ser Pro Leu Gly Val Ile Gly Ser
        195                 200                 205

Phe Thr Tyr Thr Glu Lys Ser Arg Thr Ala Ser Gly Gly Gln Ser Gly
    210                 215                 220

Gln Pro Ala Pro Ser Ile Asp Arg Ser Thr Lys Pro Pro Leu
225                 230                 235
```

<210> SEQ ID NO 10
<211> LENGTH: 215
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 30, 31, 32, 33, 34
<223> OTHER INFORMATION: Xaa = Any Amino Acid

<400> SEQUENCE: 10

```
Gly Gln Ser Gly Gln Trp Val Cys His Pro Met Trp Glu Val Met Cys
1               5                   10                  15

Leu Arg Gly Gly Ser Gly Gln Ser Ala Ser Gly Gln Ser Xaa Xaa Xaa
                20                  25                  30

Xaa Xaa Ser Gln Ser Ala Gly Gly Gln Ser Gly Gln Ser Gly Asp Tyr
            35                  40                  45

Asn Lys Asn Gln Tyr Tyr Gly Ile Thr Ala Gly Pro Ala Tyr Arg Ile
50                  55                  60

Asn Asp Trp Ala Ser Ile Tyr Gly Val Val Gly Val Gly Tyr Gly Lys
65                  70                  75                  80

Phe Gln Thr Thr Glu Tyr Pro Thr Tyr Lys His Asp Thr Ser Asp Tyr
                85                  90                  95

Gly Phe Ser Tyr Gly Ala Gly Leu Gln Phe Asn Pro Met Glu Asn Val
            100                 105                 110

Ala Leu Asp Phe Ser Tyr Glu Gln Ser Arg Ile Arg Ser Val Asp Val
        115                 120                 125

Gly Thr Trp Ile Ala Gly Val Gly Tyr Arg Phe Gly Gly Ser Gly Ala
    130                 135                 140

Thr Ser Thr Val Thr Gly Gly Tyr Ala Gln Ser Asp Ala Gln Gly Gln
145                 150                 155                 160

Met Asn Lys Met Gly Gly Phe Asn Leu Lys Tyr Arg Tyr Glu Glu Asp
                165                 170                 175

Asn Ser Pro Leu Gly Val Ile Gly Ser Phe Thr Tyr Thr Glu Lys Ser
            180                 185                 190

Arg Thr Ala Ser Gly Gly Gln Ser Gly Gln Pro Ala Pro Ser Ile Asp
        195                 200                 205

Arg Ser Thr Lys Pro Pro Leu
    210                 215
```

<210> SEQ ID NO 11
<211> LENGTH: 627
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 133, 134, 136, 137, 139, 140, 142, 143, 145, 146, 148, 149
<223> OTHER INFORMATION: n = A,T,C or G

<400> SEQUENCE: 11

```
atgaaaaaaa ttgcatgtct ttcagcactg gccgcagttc tggctttcac cgcaggtact    60
tccgtagctg gccagtctgg ccagtgggtg tgccacccga tgtgggaggt gatgtgcctg   120
aggggagggt ctnnsnnsnn snnsnnsnns ggagggcagt ctgggcagtc tggtgactac   180
aacaaaaacc agtactacgg catcactgct ggtccggctt accgcattaa cgactgggca   240
agcatctacg gtgtagtggg tgtgggttat ggtaaattcc agaccactga atacccgacc   300
tacaaacacg acaccagcga ctacggtttc tcctacggtg cgggtctgca gttcaacccg   360
atggaaaacg ttgctctgga cttctcttac gagcagagcc gtattcgtag cgttgacgta   420
ggcacctgga ttgccggtgt tggttaccgc ttcggaggaa gcggagcgac ttctactgta   480
actggcggtt acgcacagag cgacgctcag ggccaaatga caaaatgggc ggtttcaac    540
ctgaaatacc gctatgaaga agacaacagc ccgctgggtg tgatcggttc tttcacttac   600
accgagaaaa gccgtactgc aagctaa                                        627
```

<210> SEQ ID NO 12
<211> LENGTH: 208
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 45, 46, 47, 48, 49, 50
<223> OTHER INFORMATION: Xaa = Any Amino Acid

<400> SEQUENCE: 12

```
Met Lys Lys Ile Ala Cys Leu Ser Ala Leu Ala Ala Val Leu Ala Phe
  1               5                  10                  15

Thr Ala Gly Thr Ser Val Ala Gly Gln Ser Gly Gln Trp Val Cys His
             20                  25                  30

Pro Met Trp Glu Val Met Cys Leu Arg Gly Gly Ser Xaa Xaa Xaa Xaa
         35                  40                  45

Xaa Xaa Gly Gly Gln Ser Gly Gln Ser Gly Asp Tyr Asn Lys Asn Gln
     50                  55                  60

Tyr Tyr Gly Ile Thr Ala Gly Pro Ala Tyr Arg Ile Asn Asp Trp Ala
 65                  70                  75                  80

Ser Ile Tyr Gly Val Val Gly Val Gly Tyr Gly Lys Phe Gln Thr Thr
                 85                  90                  95

Glu Tyr Pro Thr Tyr Lys His Asp Thr Ser Asp Tyr Gly Phe Ser Tyr
            100                 105                 110

Gly Ala Gly Leu Gln Phe Asn Pro Met Glu Asn Val Ala Leu Asp Phe
        115                 120                 125

Ser Tyr Glu Gln Ser Arg Ile Arg Ser Val Asp Val Gly Thr Trp Ile
    130                 135                 140
```

```
Ala Gly Val Gly Tyr Arg Phe Gly Gly Ser Gly Ala Thr Ser Thr Val
145                 150                 155                 160

Thr Gly Gly Tyr Ala Gln Ser Asp Ala Gln Gln Met Asn Lys Met
                165                 170                 175

Gly Gly Phe Asn Leu Lys Tyr Arg Tyr Glu Glu Asp Asn Ser Pro Leu
            180                 185                 190

Gly Val Ile Gly Ser Phe Thr Tyr Thr Glu Lys Ser Arg Thr Ala Ser
                195                 200                 205
```

<210> SEQ ID NO 13
<211> LENGTH: 185
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 22, 23, 24, 25, 26, 27
<223> OTHER INFORMATION: Xaa = Any Amino Acid

<400> SEQUENCE: 13

```
Gly Gln Ser Gly Gln Trp Val Cys His Pro Met Trp Glu Val Met Cys
1               5                   10                  15

Leu Arg Gly Gly Ser Xaa Xaa Xaa Xaa Xaa Xaa Gly Gly Gln Ser Gly
                20                  25                  30

Gln Ser Gly Asp Tyr Asn Lys Asn Gln Tyr Tyr Gly Ile Thr Ala Gly
            35                  40                  45

Pro Ala Tyr Arg Ile Asn Asp Trp Ala Ser Ile Tyr Gly Val Val Gly
50                  55                  60

Val Gly Tyr Gly Lys Phe Gln Thr Thr Glu Tyr Pro Thr Tyr Lys His
65                  70                  75                  80

Asp Thr Ser Asp Tyr Gly Phe Ser Tyr Gly Ala Gly Leu Gln Phe Asn
                85                  90                  95

Pro Met Glu Asn Val Ala Leu Asp Phe Ser Tyr Glu Gln Ser Arg Ile
            100                 105                 110

Arg Ser Val Asp Val Gly Thr Trp Ile Ala Gly Val Gly Tyr Arg Phe
        115                 120                 125

Gly Gly Ser Gly Ala Thr Ser Thr Val Thr Gly Gly Tyr Ala Gln Ser
    130                 135                 140

Asp Ala Gln Gly Gln Met Asn Lys Met Gly Gly Phe Asn Leu Lys Tyr
145                 150                 155                 160

Arg Tyr Glu Glu Asp Asn Ser Pro Leu Gly Val Ile Gly Ser Phe Thr
                165                 170                 175

Tyr Thr Glu Lys Ser Arg Thr Ala Ser
            180                 185
```

<210> SEQ ID NO 14
<211> LENGTH: 5
<212> TYPE: PRT
<213> ORGANISM: Artificial Sequence
<220> FEATURE:
<223> OTHER INFORMATION: synthetic peptide

<400> SEQUENCE: 14

```
Gly Ser Gly Gly Ser
1               5
```

<210> SEQ ID NO 15
<211> LENGTH: 4
<212> TYPE: PRT

```
<213> ORGANISM: Artificial Sequence
<220> FEATURE:
<223> OTHER INFORMATION: synthetic peptide

<400> SEQUENCE: 15

Gly Gly Gly Ser
 1

<210> SEQ ID NO 16
<211> LENGTH: 5
<212> TYPE: PRT
<213> ORGANISM: Artificial Sequence
<220> FEATURE:
<223> OTHER INFORMATION: synthetic peptide

<400> SEQUENCE: 16

Gly Gly Ser Gly Gly
 1               5

<210> SEQ ID NO 17
<211> LENGTH: 5
<212> TYPE: PRT
<213> ORGANISM: Artificial Sequence
<220> FEATURE:
<223> OTHER INFORMATION: synthetic peptide

<400> SEQUENCE: 17

Gly Ser Gly Ser Gly
 1               5

<210> SEQ ID NO 18
<211> LENGTH: 5
<212> TYPE: PRT
<213> ORGANISM: Artificial Sequence
<220> FEATURE:
<223> OTHER INFORMATION: synthetic peptide

<400> SEQUENCE: 18

Gly Ser Gly Gly Gly
 1               5

<210> SEQ ID NO 19
<211> LENGTH: 5
<212> TYPE: PRT
<213> ORGANISM: Artificial Sequence
<220> FEATURE:
<223> OTHER INFORMATION: synthetic peptide

<400> SEQUENCE: 19

Gly Gly Gly Ser Gly
 1               5

<210> SEQ ID NO 20
<211> LENGTH: 5
<212> TYPE: PRT
<213> ORGANISM: Artificial Sequence
<220> FEATURE:
<223> OTHER INFORMATION: synthetic peptide

<400> SEQUENCE: 20

Gly Ser Ser Ser Gly
 1               5

<210> SEQ ID NO 21
<211> LENGTH: 60
<212> TYPE: DNA
<213> ORGANISM: Artificial Sequence
```

-continued

<220> FEATURE:
<223> OTHER INFORMATION: synthetic primer

<400> SEQUENCE: 21
tgcccagact gccctccttt atcatcgtca tcttgtccag accctcccct caggcacatc    60

<210> SEQ ID NO 22
<211> LENGTH: 59
<212> TYPE: DNA
<213> ORGANISM: Artificial Sequence
<220> FEATURE:
<223> OTHER INFORMATION: synthetic primer

<400> SEQUENCE: 22
tgatgtgcct gaggggaggg tctggtcaag atgaagttga tggagggcag tctgggcag     59

<210> SEQ ID NO 23
<211> LENGTH: 60
<212> TYPE: DNA
<213> ORGANISM: Artificial Sequence
<220> FEATURE:
<223> OTHER INFORMATION: synthetic primer

<400> SEQUENCE: 23
tgactgaggc cagtctggcc agtgggtgtg ccacccgatg tgggaggtga tgtgcctgag    60

<210> SEQ ID NO 24
<211> LENGTH: 60
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 27, 28, 30, 31, 33, 34, 36, 37, 39, 40, 42, 43
<223> OTHER INFORMATION: n = A,T,C or G

<400> SEQUENCE: 24
aggtgatgtg cctgagggga gggtctnnsn nsnnsnnsnn snnsggaggg cagtctgggc    60

<210> SEQ ID NO 25
<211> LENGTH: 77
<212> TYPE: DNA
<213> ORGANISM: Artificial Sequence
<220> FEATURE:
<223> OTHER INFORMATION: synthetic primer

<400> SEQUENCE: 25
caaaacagcc aagcttgcat gcggccacct tggccttatt agtggtggtg gtggtggtgt    60
ttgtacaatt cattcat                                                  77

<210> SEQ ID NO 26
<211> LENGTH: 60
<212> TYPE: DNA
<213> ORGANISM: Artificial Sequence
<220> FEATURE:
<223> OTHER INFORMATION: synthetic primer

<400> SEQUENCE: 26
ggtagcggta gcggtaccat gtcgggggag cggtggggca gcggtagcgg tggcagcatg    60

<210> SEQ ID NO 27
<211> LENGTH: 60
<212> TYPE: DNA
<213> ORGANISM: Artificial Sequence
<220> FEATURE:

<223> OTHER INFORMATION: synthetic primer

<400> SEQUENCE: 27
ggtagcggta gcggtaccgt ggactaccgc ttcctcggca gcggtagcgg tggcagcatg     60

<210> SEQ ID NO 28
<211> LENGTH: 60
<212> TYPE: DNA
<213> ORGANISM: Artificial Sequence
<220> FEATURE:
<223> OTHER INFORMATION: synthetic primer

<400> SEQUENCE: 28
ggtagcggta gcggtaccat gcacggggag aggatgggca gcggtagcgg tggcagcatg     60

<210> SEQ ID NO 29
<211> LENGTH: 60
<212> TYPE: DNA
<213> ORGANISM: Artificial Sequence
<220> FEATURE:
<223> OTHER INFORMATION: synthetic primer

<400> SEQUENCE: 29
ggtagcggta gcggtacctc cggggacagg atgtggggca gcggtagcgg tggcagcatg     60

<210> SEQ ID NO 30
<211> LENGTH: 60
<212> TYPE: DNA
<213> ORGANISM: Artificial Sequence
<220> FEATURE:
<223> OTHER INFORMATION: synthetic primer

<400> SEQUENCE: 30
ggtagcggta gcggtaccgg tgatgatgat gataaaggca gcggtagcgg tggcagcatg     60

<210> SEQ ID NO 31
<211> LENGTH: 60
<212> TYPE: DNA
<213> ORGANISM: Artificial Sequence
<220> FEATURE:
<223> OTHER INFORMATION: synthetic primer

<400> SEQUENCE: 31
ggtagcggta gcggtaccgg tggcagcggc ggtagcggtg gtggtagcgg tggcagcatg     60

<210> SEQ ID NO 32
<211> LENGTH: 7
<212> TYPE: PRT
<213> ORGANISM: Artificial Sequence
<220> FEATURE:
<223> OTHER INFORMATION: synthetic peptide

<400> SEQUENCE: 32

Asp Asp Asp Asp Lys Gly Gly
 1               5

<210> SEQ ID NO 33
<211> LENGTH: 6
<212> TYPE: PRT
<213> ORGANISM: Artificial Sequence
<220> FEATURE:
<223> OTHER INFORMATION: synthetic peptide

<400> SEQUENCE: 33

Ser Gly Asp Arg Met Trp
 1               5

<210> SEQ ID NO 34
<211> LENGTH: 12
<212> TYPE: PRT
<213> ORGANISM: Artificial Sequence
<220> FEATURE:
<223> OTHER INFORMATION: synthetic peptide

<400> SEQUENCE: 34

Trp Cys His Pro Met Trp Glu Val Met Cys Leu Arg
 1               5                  10

<210> SEQ ID NO 35
<211> LENGTH: 60
<212> TYPE: DNA
<213> ORGANISM: Artificial Sequence
<220> FEATURE:
<223> OTHER INFORMATION: synthetic primer

<400> SEQUENCE: 35
ctggccagtc tggccagtgg gtgtgccacc cgatgtggga ggtgatgtgc ctgaggggag    60

<210> SEQ ID NO 36
<211> LENGTH: 57
<212> TYPE: DNA
<213> ORGANISM: Artificial Sequence
<220> FEATURE:
<223> OTHER INFORMATION: synthetic primer

<400> SEQUENCE: 36
tgggaggtga tgtgcctgag gggagggtct ggtcaaagtg cctccggcgg tggcagc       57

<210> SEQ ID NO 37
<211> LENGTH: 57
<212> TYPE: DNA
<213> ORGANISM: Artificial Sequence
<220> FEATURE:
<223> OTHER INFORMATION: synthetic primer

<400> SEQUENCE: 37
gcctccggcg gtggcagcgg cggtagctct caatctgcgg gagggcagtc tgggcag       57

<210> SEQ ID NO 38
<211> LENGTH: 59
<212> TYPE: DNA
<213> ORGANISM: Artificial Sequence
<220> FEATURE:
<223> OTHER INFORMATION: synthetic primer

<400> SEQUENCE: 38
cttctgtcta tcgaaggagc tggctgaccg gactgacctc cgcttgcagt acggctttt     59

<210> SEQ ID NO 39
<211> LENGTH: 56
<212> TYPE: DNA
<213> ORGANISM: Artificial Sequence
<220> FEATURE:
<223> OTHER INFORMATION: synthetic primer

<400> SEQUENCE: 39
agcttggcca ccttggcctt attacagtgg gggtttcgtg cttctgtcta tcgaag        56

<210> SEQ ID NO 40
<211> LENGTH: 60
<212> TYPE: DNA
<213> ORGANISM: Artificial Sequence

```
<220> FEATURE:
<223> OTHER INFORMATION: synthetic primer

<400> SEQUENCE: 40
tgggaggtga tgtgcctgag gggagggtct ggtcaaagtg cctccggcga aaacgtctac    60

<210> SEQ ID NO 41
<211> LENGTH: 60
<212> TYPE: DNA
<213> ORGANISM: Artificial Sequence
<220> FEATURE:
<223> OTHER INFORMATION: synthetic primer

<400> SEQUENCE: 41
tccggcgaaa acgtctactt tcagagctct caatctgcgg gagggcagtc tgggcagtct    60

<210> SEQ ID NO 42
<211> LENGTH: 18
<212> TYPE: DNA
<213> ORGANISM: Artificial Sequence
<220> FEATURE:
<223> OTHER INFORMATION: synthetic primer

<400> SEQUENCE: 42
ggctgaaaat cttctctc                                                  18

<210> SEQ ID NO 43
<211> LENGTH: 60
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 25, 26, 28, 29, 31, 32, 34, 35, 37, 38
<223> OTHER INFORMATION: n = A,T,C or G

<400> SEQUENCE: 43
ggtcaaagtg cctccggcca atccnnsnns nnsnnsnnst ctcaatctgc gggagggcag    60

<210> SEQ ID NO 44
<211> LENGTH: 6
<212> TYPE: PRT
<213> ORGANISM: Artificial Sequence
<220> FEATURE:
<223> OTHER INFORMATION: synthetic peptide

<400> SEQUENCE: 44

Gly Gly Gln Ser Gly Gln
 1               5

<210> SEQ ID NO 45
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (2)...(2)
<223> OTHER INFORMATION: Xaa = E,G,V,S,T,Q,Y,F or M

<400> SEQUENCE: 45

Asp Xaa Val Asp Gly
 1               5

<210> SEQ ID NO 46
```

```
<211> LENGTH: 6
<212> TYPE: PRT
<213> ORGANISM: Artificial Sequence
<220> FEATURE:
<223> OTHER INFORMATION: synthetic peptide

<400> SEQUENCE: 46

Asp Asp Asp Asp Lys Gly
1               5

<210> SEQ ID NO 47
<211> LENGTH: 9
<212> TYPE: PRT
<213> ORGANISM: Artificial Sequence
<220> FEATURE:
<223> OTHER INFORMATION: synthetic peptide

<400> SEQUENCE: 47

Gln Asp Glu Val Asp Gly Gly Gln Ser
1               5

<210> SEQ ID NO 48
<211> LENGTH: 9
<212> TYPE: PRT
<213> ORGANISM: Artificial Sequence
<220> FEATURE:
<223> OTHER INFORMATION: synthetic peptide

<400> SEQUENCE: 48

Ser Asp Gly Val Asp Gly Trp Gly Gly
1               5

<210> SEQ ID NO 49
<211> LENGTH: 9
<212> TYPE: PRT
<213> ORGANISM: Artificial Sequence
<220> FEATURE:
<223> OTHER INFORMATION: synthetic peptide

<400> SEQUENCE: 49

Ser Asp Val Val Asp Gly Trp Gly Gly
1               5

<210> SEQ ID NO 50
<211> LENGTH: 9
<212> TYPE: PRT
<213> ORGANISM: Artificial Sequence
<220> FEATURE:
<223> OTHER INFORMATION: synthetic peptide

<400> SEQUENCE: 50

Ser Asp Gly Val Asp Gly Val Gly Gly
1               5

<210> SEQ ID NO 51
<211> LENGTH: 9
<212> TYPE: PRT
<213> ORGANISM: Artificial Sequence
<220> FEATURE:
<223> OTHER INFORMATION: synthetic peptide

<400> SEQUENCE: 51

Gly Gly Ser Leu Asp Thr Trp Thr Ala
1               5

<210> SEQ ID NO 52
<211> LENGTH: 9
```

```
<212> TYPE: PRT
<213> ORGANISM: Artificial Sequence
<220> FEATURE:
<223> OTHER INFORMATION: synthetic peptide

<400> SEQUENCE: 52

Leu Asp Thr Val Asp Arg Gly Gly Gln
 1               5

<210> SEQ ID NO 53
<211> LENGTH: 9
<212> TYPE: PRT
<213> ORGANISM: Artificial Sequence
<220> FEATURE:
<223> OTHER INFORMATION: synthetic peptide

<400> SEQUENCE: 53

Ser Asp Ser Thr Asp Ser Gly Gly Gly
 1               5

<210> SEQ ID NO 54
<211> LENGTH: 9
<212> TYPE: PRT
<213> ORGANISM: Artificial Sequence
<220> FEATURE:
<223> OTHER INFORMATION: synthetic peptide

<400> SEQUENCE: 54

Gly Ser Gln Val Asp Gly Val Gly Gly
 1               5

<210> SEQ ID NO 55
<211> LENGTH: 9
<212> TYPE: PRT
<213> ORGANISM: Artificial Sequence
<220> FEATURE:
<223> OTHER INFORMATION: synthetic peptide

<400> SEQUENCE: 55

Gly Ser Glu Val Asp Gly Arg His Gly
 1               5

<210> SEQ ID NO 56
<211> LENGTH: 9
<212> TYPE: PRT
<213> ORGANISM: Artificial Sequence
<220> FEATURE:
<223> OTHER INFORMATION: synthetic peptide

<400> SEQUENCE: 56

Ser Thr Glu Val Asp Gly Pro Gly Gly
 1               5

<210> SEQ ID NO 57
<211> LENGTH: 9
<212> TYPE: PRT
<213> ORGANISM: Artificial Sequence
<220> FEATURE:
<223> OTHER INFORMATION: synthetic peptide

<400> SEQUENCE: 57

Gly Ser Glu Val Asp Gly Gly Trp Gly
 1               5

<210> SEQ ID NO 58
<211> LENGTH: 9
<212> TYPE: PRT
```

```
<213> ORGANISM: Artificial Sequence
<220> FEATURE:
<223> OTHER INFORMATION: synthetic peptide

<400> SEQUENCE: 58

Thr Asp Gly Thr Asp Gly Gly Gly Gln
 1               5

<210> SEQ ID NO 59
<211> LENGTH: 9
<212> TYPE: PRT
<213> ORGANISM: Artificial Sequence
<220> FEATURE:
<223> OTHER INFORMATION: synthetic peptide

<400> SEQUENCE: 59

Gln Asp Gly Val Asp Thr Gly Gly Gln
 1               5

<210> SEQ ID NO 60
<211> LENGTH: 9
<212> TYPE: PRT
<213> ORGANISM: Artificial Sequence
<220> FEATURE:
<223> OTHER INFORMATION: synthetic peptide

<400> SEQUENCE: 60

Gly Ser Glu Val Asp Gly Ser Arg Gly
 1               5

<210> SEQ ID NO 61
<211> LENGTH: 9
<212> TYPE: PRT
<213> ORGANISM: Artificial Sequence
<220> FEATURE:
<223> OTHER INFORMATION: synthetic peptide

<400> SEQUENCE: 61

Gly Ser Tyr Val Asp Gly Val Val Gly
 1               5

<210> SEQ ID NO 62
<211> LENGTH: 9
<212> TYPE: PRT
<213> ORGANISM: Artificial Sequence
<220> FEATURE:
<223> OTHER INFORMATION: synthetic peptide

<400> SEQUENCE: 62

Ser Asp Phe Val Asp Arg Val Gly Gly
 1               5

<210> SEQ ID NO 63
<211> LENGTH: 9
<212> TYPE: PRT
<213> ORGANISM: Artificial Sequence
<220> FEATURE:
<223> OTHER INFORMATION: synthetic peptide

<400> SEQUENCE: 63

Gly Ser Met Val Asp Gly Ala Met Gly
 1               5

<210> SEQ ID NO 64
<211> LENGTH: 6
<212> TYPE: PRT
<213> ORGANISM: Artificial Sequence
```

```
<220> FEATURE:
<223> OTHER INFORMATION: synthetic peptide
<220> FEATURE:
<221> NAME/KEY: VARIANT
<222> LOCATION: (1)...(1)
<223> OTHER INFORMATION: Xaa = Q,S,G,L or T
<220> FEATURE:
<221> NAME/KEY: VARIANT
<222> LOCATION: (3)...(3)
<223> OTHER INFORMATION: Xaa = E,G,V,S,T,Q,Y,F or M

<400> SEQUENCE: 64

Xaa Asp Xaa Val Asp Gly
  1               5

<210> SEQ ID NO 65
<211> LENGTH: 9
<212> TYPE: PRT
<213> ORGANISM: Artificial Sequence
<220> FEATURE:
<223> OTHER INFORMATION: synthetic peptide

<400> SEQUENCE: 65

Asp Asp Asp Asp Lys Gly Gly Gln Ser
  1               5

<210> SEQ ID NO 66
<211> LENGTH: 9
<212> TYPE: PRT
<213> ORGANISM: Artificial Sequence
<220> FEATURE:
<223> OTHER INFORMATION: synthetic peptide

<400> SEQUENCE: 66

Ser Ser Gly Asp Arg Met Trp Gly Gly
  1               5

<210> SEQ ID NO 67
<211> LENGTH: 9
<212> TYPE: PRT
<213> ORGANISM: Artificial Sequence
<220> FEATURE:
<223> OTHER INFORMATION: synthetic peptide

<400> SEQUENCE: 67

Ser Ser Gly Glu Arg Met Met Gly Gly
  1               5

<210> SEQ ID NO 68
<211> LENGTH: 9
<212> TYPE: PRT
<213> ORGANISM: Artificial Sequence
<220> FEATURE:
<223> OTHER INFORMATION: synthetic peptide

<400> SEQUENCE: 68

Gly Ser Asp Asp Arg Arg Ala Gly Gly
  1               5

<210> SEQ ID NO 69
<211> LENGTH: 9
<212> TYPE: PRT
<213> ORGANISM: Artificial Sequence
<220> FEATURE:
<223> OTHER INFORMATION: synthetic peptide

<400> SEQUENCE: 69

Val Arg Asp Tyr Arg Met Gly Gly Gln
```

```
1               5
```

<210> SEQ ID NO 70
<211> LENGTH: 9
<212> TYPE: PRT
<213> ORGANISM: Artificial Sequence
<220> FEATURE:
<223> OTHER INFORMATION: synthetic peptide

<400> SEQUENCE: 70

```
Gly Ser Ser Asp Arg Ala Arg Val Trp
1               5
```

<210> SEQ ID NO 71
<211> LENGTH: 9
<212> TYPE: PRT
<213> ORGANISM: Artificial Sequence
<220> FEATURE:
<223> OTHER INFORMATION: synthetic peptide

<400> SEQUENCE: 71

```
Ser Val Asp Tyr Arg Phe Leu Gly Ser
1               5
```

<210> SEQ ID NO 72
<211> LENGTH: 9
<212> TYPE: PRT
<213> ORGANISM: Artificial Sequence
<220> FEATURE:
<223> OTHER INFORMATION: synthetic peptide

<400> SEQUENCE: 72

```
Met His Gly Glu Arg Met Gly Gly Ser
1               5
```

<210> SEQ ID NO 73
<211> LENGTH: 9
<212> TYPE: PRT
<213> ORGANISM: Artificial Sequence
<220> FEATURE:
<223> OTHER INFORMATION: synthetic peptide

<400> SEQUENCE: 73

```
Met Ser Gly Glu Arg Met Gly Gly Ser
1               5
```

<210> SEQ ID NO 74
<211> LENGTH: 9
<212> TYPE: PRT
<213> ORGANISM: Artificial Sequence
<220> FEATURE:
<223> OTHER INFORMATION: synthetic peptide

<400> SEQUENCE: 74

```
Gly Ser Ser Glu Arg Ala Ala Ala Gly
1               5
```

<210> SEQ ID NO 75
<211> LENGTH: 9
<212> TYPE: PRT
<213> ORGANISM: Artificial Sequence
<220> FEATURE:
<223> OTHER INFORMATION: synthetic peptide

<400> SEQUENCE: 75

```
Ser Val Leu Asp Arg Trp Met Gly Gly
1               5
```

```
<210> SEQ ID NO 76
<211> LENGTH: 9
<212> TYPE: PRT
<213> ORGANISM: Artificial Sequence
<220> FEATURE:
<223> OTHER INFORMATION: synthetic peptide

<400> SEQUENCE: 76

Ser Glu Tyr Asp Arg Gln Leu Gly Ser
 1               5

<210> SEQ ID NO 77
<211> LENGTH: 9
<212> TYPE: PRT
<213> ORGANISM: Artificial Sequence
<220> FEATURE:
<223> OTHER INFORMATION: synthetic peptide

<400> SEQUENCE: 77

Ala Ala Val Glu Arg Trp Gly Gly Ser
 1               5

<210> SEQ ID NO 78
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (1)...(1)
<223> OTHER INFORMATION: Xaa = S,R,V,H,E or A
<220> FEATURE:
<221> NAME/KEY: VARIANT
<222> LOCATION: (2)...(2)
<223> OTHER INFORMATION: Xaa = G,D,S,L,Y, or V
<220> FEATURE:
<221> NAME/KEY: VARIANT
<222> LOCATION: (3)...(3)
<223> OTHER INFORMATION: Xaa = D or E
<220> FEATURE:
<221> NAME/KEY: VARIANT
<222> LOCATION: (6)...(6)
<223> OTHER INFORMATION: Xaa = W,M,A,G,R,L or M

<400> SEQUENCE: 78

Xaa Xaa Xaa Arg Met Xaa
 1               5

<210> SEQ ID NO 79
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (2)...(2)
<223> OTHER INFORMATION: Xaa = E,G,V,S,T,Q,Y,F or M
<220> FEATURE:
<221> NAME/KEY: VARIANT
<222> LOCATION: (3)...(3)
<223> OTHER INFORMATION: Xaa = V or L

<400> SEQUENCE: 79

Asp Xaa Xaa Asp Gly
 1               5

<210> SEQ ID NO 80
```

```
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (2)...(2)
<223> OTHER INFORMATION: Xaa = E,G,V,S,T,Q,Y,F or M

<400> SEQUENCE: 80

Asp Xaa Val Asp
 1

<210> SEQ ID NO 81
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (2)...(2)
<223> OTHER INFORMATION: Xaa = E,G,V,S,T,Q,Y,F or M

<400> SEQUENCE: 81

Asp Xaa Val Asp Gly
 1               5

<210> SEQ ID NO 82
<211> LENGTH: 5
<212> TYPE: PRT
<213> ORGANISM: Artificial Sequence
<220> FEATURE:
<223> OTHER INFORMATION: synthetic peptide

<400> SEQUENCE: 82

Glu Glu Glu Leu Tyr
 1               5

<210> SEQ ID NO 83
<211> LENGTH: 5
<212> TYPE: PRT
<213> ORGANISM: Artificial Sequence
<220> FEATURE:
<223> OTHER INFORMATION: synthetic peptide

<400> SEQUENCE: 83

Glu Glu Glu Leu Trp
 1               5

<210> SEQ ID NO 84
<211> LENGTH: 5
<212> TYPE: PRT
<213> ORGANISM: Artificial Sequence
<220> FEATURE:
<223> OTHER INFORMATION: synthetic peptide

<400> SEQUENCE: 84

Arg Glu Val Leu Tyr
 1               5

<210> SEQ ID NO 85
<211> LENGTH: 7
<212> TYPE: PRT
<213> ORGANISM: Artificial Sequence
<220> FEATURE:
<223> OTHER INFORMATION: synthetic peptide
```

```
<400> SEQUENCE: 85

Glu Asn Val Tyr Phe Gln Ser
 1               5

<210> SEQ ID NO 86
<211> LENGTH: 7
<212> TYPE: PRT
<213> ORGANISM: Artificial Sequence
<220> FEATURE:
<223> OTHER INFORMATION: synthetic peptide

<400> SEQUENCE: 86

Glu Asn Val Tyr Phe Gln Ser
 1               5

<210> SEQ ID NO 87
<211> LENGTH: 5
<212> TYPE: PRT
<213> ORGANISM: Artificial Sequence
<220> FEATURE:
<223> OTHER INFORMATION: synthetic peptide

<400> SEQUENCE: 87

Gly Glu His Val Tyr
 1               5

<210> SEQ ID NO 88
<211> LENGTH: 5
<212> TYPE: PRT
<213> ORGANISM: Artificial Sequence
<220> FEATURE:
<223> OTHER INFORMATION: synthetic peptide

<400> SEQUENCE: 88

Glu Glu Ala Val Leu
 1               5

<210> SEQ ID NO 89
<211> LENGTH: 5
<212> TYPE: PRT
<213> ORGANISM: Artificial Sequence
<220> FEATURE:
<223> OTHER INFORMATION: synthetic peptide

<400> SEQUENCE: 89

Asp Val Gln Leu Tyr
 1               5

<210> SEQ ID NO 90
<211> LENGTH: 5
<212> TYPE: PRT
<213> ORGANISM: Artificial Sequence
<220> FEATURE:
<223> OTHER INFORMATION: synthetic peptide

<400> SEQUENCE: 90

Leu Tyr Phe Gln Gly
 1               5

<210> SEQ ID NO 91
<211> LENGTH: 5
<212> TYPE: PRT
<213> ORGANISM: Artificial Sequence
<220> FEATURE:
<223> OTHER INFORMATION: synthetic peptide

<400> SEQUENCE: 91
```

```
Asp Ser Glu Leu Tyr
1               5

<210> SEQ ID NO 92
<211> LENGTH: 5
<212> TYPE: PRT
<213> ORGANISM: Artificial Sequence
<220> FEATURE:
<223> OTHER INFORMATION: synthetic peptide

<400> SEQUENCE: 92

Asp Arg Glu Leu Tyr
1               5

<210> SEQ ID NO 93
<211> LENGTH: 5
<212> TYPE: PRT
<213> ORGANISM: Artificial Sequence
<220> FEATURE:
<223> OTHER INFORMATION: synthetic peptide

<400> SEQUENCE: 93

Trp Glu Ser Leu Tyr
1               5

<210> SEQ ID NO 94
<211> LENGTH: 5
<212> TYPE: PRT
<213> ORGANISM: Artificial Sequence
<220> FEATURE:
<223> OTHER INFORMATION: synthetic peptide

<400> SEQUENCE: 94

Leu Glu Gln Leu Ile
1               5

<210> SEQ ID NO 95
<211> LENGTH: 5
<212> TYPE: PRT
<213> ORGANISM: Artificial Sequence
<220> FEATURE:
<223> OTHER INFORMATION: synthetic peptide

<400> SEQUENCE: 95

Leu Glu Trp Leu Lys
1               5

<210> SEQ ID NO 96
<211> LENGTH: 5
<212> TYPE: PRT
<213> ORGANISM: Artificial Sequence
<220> FEATURE:
<223> OTHER INFORMATION: synthetic peptide

<400> SEQUENCE: 96

Leu Glu Ser Leu Val
1               5

<210> SEQ ID NO 97
<211> LENGTH: 5
<212> TYPE: PRT
<213> ORGANISM: Artificial Sequence
<220> FEATURE:
<223> OTHER INFORMATION: synthetic peptide

<400> SEQUENCE: 97
```

```
Arg Arg Met Ala Glu
1               5

<210> SEQ ID NO 98
<211> LENGTH: 5
<212> TYPE: PRT
<213> ORGANISM: Artificial Sequence
<220> FEATURE:
<223> OTHER INFORMATION: synthetic peptide

<400> SEQUENCE: 98

Leu Arg Glu Leu Trp
1               5

<210> SEQ ID NO 99
<211> LENGTH: 5
<212> TYPE: PRT
<213> ORGANISM: Artificial Sequence
<220> FEATURE:
<223> OTHER INFORMATION: synthetic peptide

<400> SEQUENCE: 99

Gly Glu Asp Leu Leu
1               5

<210> SEQ ID NO 100
<211> LENGTH: 5
<212> TYPE: PRT
<213> ORGANISM: Artificial Sequence
<220> FEATURE:
<223> OTHER INFORMATION: synthetic peptide

<400> SEQUENCE: 100

Gly Glu Ala Leu Phe
1               5

<210> SEQ ID NO 101
<211> LENGTH: 5
<212> TYPE: PRT
<213> ORGANISM: Artificial Sequence
<220> FEATURE:
<223> OTHER INFORMATION: synthetic peptide

<400> SEQUENCE: 101

Met Glu Met Leu Arg
1               5

<210> SEQ ID NO 102
<211> LENGTH: 5
<212> TYPE: PRT
<213> ORGANISM: Artificial Sequence
<220> FEATURE:
<223> OTHER INFORMATION: synthetic peptide

<400> SEQUENCE: 102

Ser Glu Pro Leu Arg
1               5

<210> SEQ ID NO 103
<211> LENGTH: 5
<212> TYPE: PRT
<213> ORGANISM: Artificial Sequence
<220> FEATURE:
<223> OTHER INFORMATION: synthetic peptide

<400> SEQUENCE: 103

Ser Glu Asp Leu Trp
```

```
<210> SEQ ID NO 104
<211> LENGTH: 5
<212> TYPE: PRT
<213> ORGANISM: Artificial Sequence
<220> FEATURE:
<223> OTHER INFORMATION: synthetic peptide

<400> SEQUENCE: 104

Met Glu Trp Leu Trp
 1               5

<210> SEQ ID NO 105
<211> LENGTH: 5
<212> TYPE: PRT
<213> ORGANISM: Artificial Sequence
<220> FEATURE:
<223> OTHER INFORMATION: synthetic peptide

<400> SEQUENCE: 105

Trp Glu Pro Leu Trp
 1               5

<210> SEQ ID NO 106

<400> SEQUENCE: 106

000

<210> SEQ ID NO 107
<211> LENGTH: 5
<212> TYPE: PRT
<213> ORGANISM: Artificial Sequence
<220> FEATURE:
<223> OTHER INFORMATION: synthetic peptide

<400> SEQUENCE: 107

Phe Glu Asp Leu Leu
 1               5

<210> SEQ ID NO 108
<211> LENGTH: 5
<212> TYPE: PRT
<213> ORGANISM: Artificial Sequence
<220> FEATURE:
<223> OTHER INFORMATION: synthetic peptide

<400> SEQUENCE: 108

Met Glu Asp Leu Met
 1               5

<210> SEQ ID NO 109
<211> LENGTH: 5
<212> TYPE: PRT
<213> ORGANISM: Artificial Sequence
<220> FEATURE:
<223> OTHER INFORMATION: synthetic peptide

<400> SEQUENCE: 109

Met Glu Glu Val Tyr
 1               5

<210> SEQ ID NO 110
<211> LENGTH: 5
<212> TYPE: PRT
<213> ORGANISM: Artificial Sequence
```

```
<220> FEATURE:
<223> OTHER INFORMATION: synthetic peptide

<400> SEQUENCE: 110

Asp Gly Ala Leu Tyr
1               5

<210> SEQ ID NO 111
<211> LENGTH: 5
<212> TYPE: PRT
<213> ORGANISM: Artificial Sequence
<220> FEATURE:
<223> OTHER INFORMATION: synthetic peptide

<400> SEQUENCE: 111

Asp Arg Glu Leu Tyr
1               5

<210> SEQ ID NO 112
<211> LENGTH: 5
<212> TYPE: PRT
<213> ORGANISM: Artificial Sequence
<220> FEATURE:
<223> OTHER INFORMATION: synthetic peptide

<400> SEQUENCE: 112

Glu Thr Ile Leu Tyr
1               5

<210> SEQ ID NO 113
<211> LENGTH: 5
<212> TYPE: PRT
<213> ORGANISM: Artificial Sequence
<220> FEATURE:
<223> OTHER INFORMATION: synthetic peptide

<400> SEQUENCE: 113

Gly Glu Ala Leu Phe
1               5

<210> SEQ ID NO 114
<211> LENGTH: 5
<212> TYPE: PRT
<213> ORGANISM: Artificial Sequence
<220> FEATURE:
<223> OTHER INFORMATION: synthetic peptide

<400> SEQUENCE: 114

Gly Glu Pro Leu Trp
1               5

<210> SEQ ID NO 115
<211> LENGTH: 5
<212> TYPE: PRT
<213> ORGANISM: Artificial Sequence
<220> FEATURE:
<223> OTHER INFORMATION: synthetic peptide

<400> SEQUENCE: 115

Glu Glu Tyr Leu Trp
1               5

<210> SEQ ID NO 116
<211> LENGTH: 5
<212> TYPE: PRT
<213> ORGANISM: Artificial Sequence
<220> FEATURE:
```

```
<223> OTHER INFORMATION: synthetic peptide

<400> SEQUENCE: 116

Glu Glu Asn Leu Gly
 1               5

<210> SEQ ID NO 117
<211> LENGTH: 4
<212> TYPE: PRT
<213> ORGANISM: Artificial Sequence
<220> FEATURE:
<223> OTHER INFORMATION: synthetic peptide

<400> SEQUENCE: 117

Glu Glu Leu Tyr
 1

<210> SEQ ID NO 118
<211> LENGTH: 5
<212> TYPE: PRT
<213> ORGANISM: Artificial Sequence
<220> FEATURE:
<223> OTHER INFORMATION: synthetic peptide

<400> SEQUENCE: 118

Phe Glu Asp Gly Leu
 1               5

<210> SEQ ID NO 119
<211> LENGTH: 5
<212> TYPE: PRT
<213> ORGANISM: Artificial Sequence
<220> FEATURE:
<223> OTHER INFORMATION: synthetic peptide

<400> SEQUENCE: 119

Gly Glu Thr Val Tyr
 1               5

<210> SEQ ID NO 120
<211> LENGTH: 5
<212> TYPE: PRT
<213> ORGANISM: Artificial Sequence
<220> FEATURE:
<223> OTHER INFORMATION: synthetic peptide

<400> SEQUENCE: 120

Arg Glu Leu Val Tyr
 1               5

<210> SEQ ID NO 121
<211> LENGTH: 5
<212> TYPE: PRT
<213> ORGANISM: Artificial Sequence
<220> FEATURE:
<223> OTHER INFORMATION: synthetic peptide

<400> SEQUENCE: 121

Val Glu Pro Ile Tyr
 1               5

<210> SEQ ID NO 122
<211> LENGTH: 5
<212> TYPE: PRT
<213> ORGANISM: Artificial Sequence
<220> FEATURE:
<223> OTHER INFORMATION: synthetic peptide
```

```
<400> SEQUENCE: 122

Arg Glu Val Gly Tyr
1               5

<210> SEQ ID NO 123
<211> LENGTH: 5
<212> TYPE: PRT
<213> ORGANISM: Artificial Sequence
<220> FEATURE:
<223> OTHER INFORMATION: synthetic peptide

<400> SEQUENCE: 123

Arg Asp Asp Gly Tyr
1               5

<210> SEQ ID NO 124
<211> LENGTH: 5
<212> TYPE: PRT
<213> ORGANISM: Artificial Sequence
<220> FEATURE:
<223> OTHER INFORMATION: synthetic peptide

<400> SEQUENCE: 124

Gly Asp Met Gly Tyr
1               5

<210> SEQ ID NO 125
<211> LENGTH: 5
<212> TYPE: PRT
<213> ORGANISM: Artificial Sequence
<220> FEATURE:
<223> OTHER INFORMATION: synthetic peptide

<400> SEQUENCE: 125

Ala Arg Gln Ile Arg
1               5

<210> SEQ ID NO 126
<211> LENGTH: 5
<212> TYPE: PRT
<213> ORGANISM: Artificial Sequence
<220> FEATURE:
<223> OTHER INFORMATION: synthetic peptide

<400> SEQUENCE: 126

Ala Glu Trp Gly Arg
1               5

<210> SEQ ID NO 127
<211> LENGTH: 5
<212> TYPE: PRT
<213> ORGANISM: Artificial Sequence
<220> FEATURE:
<223> OTHER INFORMATION: synthetic peptide

<400> SEQUENCE: 127

Gly Glu Ala Gly Val
1               5

<210> SEQ ID NO 128
<211> LENGTH: 5
<212> TYPE: PRT
<213> ORGANISM: Artificial Sequence
<220> FEATURE:
<223> OTHER INFORMATION: synthetic peptide
```

```
<400> SEQUENCE: 128

Gly Glu Ala Gly Phe
1               5

<210> SEQ ID NO 129
<211> LENGTH: 5
<212> TYPE: PRT
<213> ORGANISM: Artificial Sequence
<220> FEATURE:
<223> OTHER INFORMATION: synthetic peptide

<400> SEQUENCE: 129

Glu Glu Tyr Leu Trp
1               5

<210> SEQ ID NO 130
<211> LENGTH: 4
<212> TYPE: PRT
<213> ORGANISM: Artificial Sequence
<220> FEATURE:
<223> OTHER INFORMATION: synthetic peptide

<400> SEQUENCE: 130

Gly Glu Leu Tyr
1

<210> SEQ ID NO 131
<211> LENGTH: 5
<212> TYPE: PRT
<213> ORGANISM: Artificial Sequence
<220> FEATURE:
<223> OTHER INFORMATION: synthetic peptide

<400> SEQUENCE: 131

Gly Glu Val Leu Trp
1               5

<210> SEQ ID NO 132
<211> LENGTH: 5
<212> TYPE: PRT
<213> ORGANISM: Artificial Sequence
<220> FEATURE:
<223> OTHER INFORMATION: synthetic peptide

<400> SEQUENCE: 132

Asp Arg Glu Leu Tyr
1               5

<210> SEQ ID NO 133
<211> LENGTH: 5
<212> TYPE: PRT
<213> ORGANISM: Artificial Sequence
<220> FEATURE:
<223> OTHER INFORMATION: synthetic peptide

<400> SEQUENCE: 133

Trp Glu Ser Leu Tyr
1               5

<210> SEQ ID NO 134
<211> LENGTH: 5
<212> TYPE: PRT
<213> ORGANISM: Artificial Sequence
<220> FEATURE:
<223> OTHER INFORMATION: synthetic peptide

<400> SEQUENCE: 134
```

```
Leu Glu Gln Leu Ile
 1               5

<210> SEQ ID NO 135
<211> LENGTH: 5
<212> TYPE: PRT
<213> ORGANISM: Artificial Sequence
<220> FEATURE:
<223> OTHER INFORMATION: synthetic peptide

<400> SEQUENCE: 135

Trp Glu Pro Leu Trp
 1               5

<210> SEQ ID NO 136
<211> LENGTH: 5
<212> TYPE: PRT
<213> ORGANISM: Artificial Sequence
<220> FEATURE:
<223> OTHER INFORMATION: synthetic peptide

<400> SEQUENCE: 136

Glu Glu Glu Leu Tyr
 1               5

<210> SEQ ID NO 137
<211> LENGTH: 5
<212> TYPE: PRT
<213> ORGANISM: Artificial Sequence
<220> FEATURE:
<223> OTHER INFORMATION: synthetic peptide

<400> SEQUENCE: 137

Gly Glu Asp Leu Leu
 1               5

<210> SEQ ID NO 138
<211> LENGTH: 5
<212> TYPE: PRT
<213> ORGANISM: Artificial Sequence
<220> FEATURE:
<223> OTHER INFORMATION: synthetic peptide

<400> SEQUENCE: 138

Glu Glu Ala Val Leu
 1               5

<210> SEQ ID NO 139
<211> LENGTH: 6
<212> TYPE: PRT
<213> ORGANISM: Artificial Sequence
<220> FEATURE:
<223> OTHER INFORMATION: synthetic peptide

<400> SEQUENCE: 139

Ala Leu Tyr Ile Gln Gly
 1               5

<210> SEQ ID NO 140
<211> LENGTH: 6
<212> TYPE: PRT
<213> ORGANISM: Artificial Sequence
<220> FEATURE:
<223> OTHER INFORMATION: synthetic peptide

<400> SEQUENCE: 140
```

```
Phe Leu Tyr Leu Gln Gly
 1               5

<210> SEQ ID NO 141
<211> LENGTH: 6
<212> TYPE: PRT
<213> ORGANISM: Artificial Sequence
<220> FEATURE:
<223> OTHER INFORMATION: synthetic peptide

<400> SEQUENCE: 141

Ser Leu Tyr Val Gln Gly
 1               5

<210> SEQ ID NO 142
<211> LENGTH: 6
<212> TYPE: PRT
<213> ORGANISM: Artificial Sequence
<220> FEATURE:
<223> OTHER INFORMATION: synthetic peptide

<400> SEQUENCE: 142

Val Leu Tyr Leu Gln Ser
 1               5

<210> SEQ ID NO 143
<211> LENGTH: 6
<212> TYPE: PRT
<213> ORGANISM: Artificial Sequence
<220> FEATURE:
<223> OTHER INFORMATION: synthetic peptide

<400> SEQUENCE: 143

Asp Leu Tyr Trp Gln Gly
 1               5

<210> SEQ ID NO 144
<211> LENGTH: 6
<212> TYPE: PRT
<213> ORGANISM: Artificial Sequence
<220> FEATURE:
<223> OTHER INFORMATION: synthetic peptide

<400> SEQUENCE: 144

Ser Leu Tyr Trp Gln Gly
 1               5

<210> SEQ ID NO 145
<211> LENGTH: 6
<212> TYPE: PRT
<213> ORGANISM: Artificial Sequence
<220> FEATURE:
<223> OTHER INFORMATION: synthetic peptide

<400> SEQUENCE: 145

Glu Leu Tyr Trp Gln Gly
 1               5

<210> SEQ ID NO 146
<211> LENGTH: 6
<212> TYPE: PRT
<213> ORGANISM: Artificial Sequence
<220> FEATURE:
<223> OTHER INFORMATION: synthetic peptide

<400> SEQUENCE: 146

Trp Leu Tyr Leu Gln Gly
```

```
1               5

<210> SEQ ID NO 147
<211> LENGTH: 6
<212> TYPE: PRT
<213> ORGANISM: Artificial Sequence
<220> FEATURE:
<223> OTHER INFORMATION: synthetic peptide

<400> SEQUENCE: 147

Gln Leu Tyr Phe Gln Ser
1               5

<210> SEQ ID NO 148
<211> LENGTH: 6
<212> TYPE: PRT
<213> ORGANISM: Artificial Sequence
<220> FEATURE:
<223> OTHER INFORMATION: synthetic peptide

<400> SEQUENCE: 148

Glu Val Tyr Val Gln Gly
1               5

<210> SEQ ID NO 149
<211> LENGTH: 6
<212> TYPE: PRT
<213> ORGANISM: Artificial Sequence
<220> FEATURE:
<223> OTHER INFORMATION: synthetic peptide

<400> SEQUENCE: 149

Glu Leu Tyr Ala Gln Gly
1               5

<210> SEQ ID NO 150
<211> LENGTH: 6
<212> TYPE: PRT
<213> ORGANISM: Artificial Sequence
<220> FEATURE:
<223> OTHER INFORMATION: synthetic peptide

<400> SEQUENCE: 150

Val Leu Tyr Thr Gln Gly
1               5

<210> SEQ ID NO 151
<211> LENGTH: 6
<212> TYPE: PRT
<213> ORGANISM: Artificial Sequence
<220> FEATURE:
<223> OTHER INFORMATION: synthetic peptide

<400> SEQUENCE: 151

Asp Val Tyr Val Gln Gly
1               5

<210> SEQ ID NO 152
<211> LENGTH: 6
<212> TYPE: PRT
<213> ORGANISM: Artificial Sequence
<220> FEATURE:
<223> OTHER INFORMATION: synthetic peptide

<400> SEQUENCE: 152

Leu Leu Tyr Ile Gln Gly
1               5
```

```
<210> SEQ ID NO 153
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (4)...(4)
<223> OTHER INFORMATION: Xaa = L or V
<220> FEATURE:
<221> NAME/KEY: VARIANT
<222> LOCATION: (5)...(5)
<223> OTHER INFORMATION: Xaa = Y or W
<220> FEATURE:
<221> NAME/KEY: VARIANT
<222> LOCATION: 1, 3, 6
<223> OTHER INFORMATION: Xaa = Any Amino Acid

<400> SEQUENCE: 153

Xaa Glu Xaa Xaa Xaa Xaa
 1               5

<210> SEQ ID NO 154
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (3)...(3)
<223> OTHER INFORMATION: Xaa = L or V
<220> FEATURE:
<221> NAME/KEY: VARIANT
<222> LOCATION: (4)...(4)
<223> OTHER INFORMATION: Xaa = Y,W,or S
<220> FEATURE:
<221> NAME/KEY: VARIANT
<222> LOCATION: 2, 5, 6, 7
<223> OTHER INFORMATION: Xaa = Any Amino Acid

<400> SEQUENCE: 154

Glu Xaa Xaa Xaa Xaa Xaa Xaa
 1               5

<210> SEQ ID NO 155
<211> LENGTH: 5
<212> TYPE: PRT
<213> ORGANISM: Artificial Sequence
<220> FEATURE:
<223> OTHER INFORMATION: synthetic peptide

<400> SEQUENCE: 155

Val Pro Leu Asn Met
 1               5

<210> SEQ ID NO 156
<211> LENGTH: 5
<212> TYPE: PRT
<213> ORGANISM: Artificial Sequence
<220> FEATURE:
<223> OTHER INFORMATION: synthetic peptide

<400> SEQUENCE: 156

Val Pro Met Val Val
 1               5

<210> SEQ ID NO 157
```

```
<211> LENGTH: 5
<212> TYPE: PRT
<213> ORGANISM: Artificial Sequence
<220> FEATURE:
<223> OTHER INFORMATION: synthetic peptide

<400> SEQUENCE: 157

Pro Val Asn Val Val
1               5

<210> SEQ ID NO 158
<211> LENGTH: 5
<212> TYPE: PRT
<213> ORGANISM: Artificial Sequence
<220> FEATURE:
<223> OTHER INFORMATION: synthetic peptide

<400> SEQUENCE: 158

Val Pro Val Asn Met
1               5

<210> SEQ ID NO 159
<211> LENGTH: 5
<212> TYPE: PRT
<213> ORGANISM: Artificial Sequence
<220> FEATURE:
<223> OTHER INFORMATION: synthetic peptide

<400> SEQUENCE: 159

Pro Val Ala Met Arg
1               5

<210> SEQ ID NO 160
<211> LENGTH: 5
<212> TYPE: PRT
<213> ORGANISM: Artificial Sequence
<220> FEATURE:
<223> OTHER INFORMATION: synthetic peptide

<400> SEQUENCE: 160

Pro Met Ala Val Ile
1               5

<210> SEQ ID NO 161
<211> LENGTH: 5
<212> TYPE: PRT
<213> ORGANISM: Artificial Sequence
<220> FEATURE:
<223> OTHER INFORMATION: synthetic peptide

<400> SEQUENCE: 161

Met Pro Leu Val Met
1               5

<210> SEQ ID NO 162
<211> LENGTH: 5
<212> TYPE: PRT
<213> ORGANISM: Artificial Sequence
<220> FEATURE:
<223> OTHER INFORMATION: synthetic peptide

<400> SEQUENCE: 162

Val Pro Leu Asn Met
1               5

<210> SEQ ID NO 163
<211> LENGTH: 5
```

```
<212> TYPE: PRT
<213> ORGANISM: Artificial Sequence
<220> FEATURE:
<223> OTHER INFORMATION: synthetic peptide

<400> SEQUENCE: 163

Pro Met Ala Val Thr
1               5

<210> SEQ ID NO 164
<211> LENGTH: 5
<212> TYPE: PRT
<213> ORGANISM: Artificial Sequence
<220> FEATURE:
<223> OTHER INFORMATION: synthetic peptide

<400> SEQUENCE: 164

Pro Val Pro Met Val
1               5

<210> SEQ ID NO 165
<211> LENGTH: 5
<212> TYPE: PRT
<213> ORGANISM: Artificial Sequence
<220> FEATURE:
<223> OTHER INFORMATION: synthetic peptide

<400> SEQUENCE: 165

Val Pro Met Val Val
1               5

<210> SEQ ID NO 166
<211> LENGTH: 5
<212> TYPE: PRT
<213> ORGANISM: Artificial Sequence
<220> FEATURE:
<223> OTHER INFORMATION: synthetic peptide

<400> SEQUENCE: 166

Met Pro Val Val Leu
1               5

<210> SEQ ID NO 167
<211> LENGTH: 5
<212> TYPE: PRT
<213> ORGANISM: Artificial Sequence
<220> FEATURE:
<223> OTHER INFORMATION: synthetic peptide

<400> SEQUENCE: 167

Thr Pro Leu Ala Leu
1               5

<210> SEQ ID NO 168
<211> LENGTH: 5
<212> TYPE: PRT
<213> ORGANISM: Artificial Sequence
<220> FEATURE:
<223> OTHER INFORMATION: synthetic peptide

<400> SEQUENCE: 168

Val Pro Val Val Met
1               5

<210> SEQ ID NO 169
<211> LENGTH: 18
<212> TYPE: DNA
```

```
<213> ORGANISM: Artificial Sequence
<220> FEATURE:
<223> OTHER INFORMATION: synthetic primer

<400> SEQUENCE: 169
ggctgaaaat cttctctc                                                   18

<210> SEQ ID NO 170
<211> LENGTH: 60
<212> TYPE: DNA
<213> ORGANISM: Artificial Sequence
<220> FEATURE:
<223> OTHER INFORMATION: synthetic primer

<400> SEQUENCE: 170
ctggccagtc tggccagtgg gtgtgccacc cgatgtggga ggtgatgtgc ctgagggag      60
```

CELLULAR LIBRARIES OF PEPTIDE SEQUENCES (CLIPS) AND METHODS OF USING THE SAME

CROSS-REFERENCE

This application is a continuation of U.S. application Ser. No. 11/514,377 filed on Aug. 30, 2006, now U.S. Pat. No. 7,666,817 which claims the benefit of U.S. Provisional Application No. 60/712,434 filed Aug. 31, 2005, which applications are incorporated herein by reference.

GOVERNMENT RIGHTS

This invention was made with government support under federal grant no. BES-0449399 awarded by the National Science Foundation, The United States Government has certain rights in this invention.

BACKGROUND OF THE INVENTION

Combinatorial library screening and selection methods have become a common tool for identifying substrates or inhibitors of enzymes. The most widespread technique is phage display, whereby the protein of interest is expressed as a polypeptide fusion to a bacteriophage coat protein and subsequently screened by binding to immobilized or soluble biotinylated ligand. Phage display has been successfully applied to antibodies, DNA binding proteins, protease inhibitors, short peptides, and enzymes (Choo & Klug, 1995, Hoogenboom, 1997, Ladner, 1995, Lowman et al., 1991, Markland et al., 1996, Matthews & Wells, 1993, Wang et al., 1996).

Nevertheless, phage display possesses several shortcomings. For example, the nature of phage display precludes quantitative and direct discrimination of ligand binding parameters, such as quantitative characterization of protease specificity and substrate cleavage kinetics. Furthermore, some eukaryotic secreted proteins and cell surface proteins require post-translational modifications such as glycosylation or extensive disulfide isomerization which are unavailable in bacterial cells.

Accordingly, there remains a need in this art for systems and methods that provide efficient display and screening of polypeptides at the cell surface, as well as qualitative and quantitative characterization of the candidate polypeptides. The present invention addresses this need.

RELEVANT LITERATURE

U.S. Pat. Nos. 6,723,512, 6,699,658, 6,696,251, 6,423,538, 6,300,065; United States Patent Publication Nos. 2004/0146976, 2005/0196406, 2006/0003387, 2006/0029947; Bessette et al., Prot. Eng., Design & Sel. 17(10):731-739 (2004); Deperthes et al., Biol. Chem., 383:1107-1112 (2002); Bessette et al., Biotechnol. Prog. 20:963-967 (2004); Daugherty et al., J. Immunol. Meth., 243:211-227 (2000); Daugherty et al., Protein. Eng., 12(7):613-621 (1999); Boulware et al., PNAS 103(20):7583-7588 (2006); and WO 2005/047461.

SUMMARY OF THE INVENTION

The present invention provides compositions including peptide display scaffolds that present at least one candidate peptide and at least one detectable moiety in at least one of the N-terminal and C-terminal candidate peptide presenting domains that when expressed in a cell are accessible at a surface of the cell outermembrane. In addition, the present invention also provides kits and methods for screening a library of cells presenting the candidate peptides in peptide display scaffolds to identify a ligand for an enzyme.

The present invention provides a method for screening a library of cells presenting candidate peptides in peptide display scaffolds to identify a peptide substrate for an enzyme, by contacting an enzyme with a cell library enriched for expression of peptide display scaffolds, wherein each peptide display scaffold includes:

[D-C]-TM wherein TM is a transmembrane protein, C is a candidate peptide; and D is a detectable moiety, wherein the cells of the cell library exhibit a D signal prior to contacting with the enzyme; and detecting the presence or absence of a D signal, wherein a decrease in the D signal in the presence of the enzyme as compared to the absence of the enzyme indicates that at least one cell of the cell library expresses a candidate peptide that is a substrate for the enzyme.

In some embodiments, the cell library enriched for expression of peptide display scaffolds is produced by fluorescence activated cell sorting of cells exhibiting the D signal. In certain embodiments, detecting the presence or absence of the D signal is by fluorescence activated cell sorting. In some embodiments, the TM protein is a bacterial outer membrane protein. In some embodiments, the peptide display scaffold further comprises a linker between C and TM. In some embodiments, D is an affinity ligand, such as a streptavadin binding peptide, a monocytic adaptor protein (MONA) binding peptide, or a T7 binding peptide.

In certain embodiments C is [A-$C_S$] or [$C_S$-A] wherein A is an allosteric regulator for the enzyme and $C_s$ is a candidate substrate for the enzyme, and wherein a decrease in the D signal indicates that at least one cell of the cell library expresses a candidate peptide that is a substrate for the enzyme.

The present invention also provides a method for screening a library of cells presenting candidate peptides in peptide display scaffolds to identify a peptide inhibitor for an enzyme, by contacting an enzyme with a cell library enriched for expression of peptide display scaffolds, wherein each peptide display scaffold comprises:

[D-S-$C_i$]-TM wherein TM is a transmembrane protein, S is a substrate for the enzyme, $C_i$ is a candidate inhibitor peptide, and D is a detectable moiety, wherein the cells of the cell library exhibit a D signal prior to contacting with the enzyme; and detecting the presence or absence of a D signal, wherein maintenance of the D signal in the presence of the enzyme as compared to the absence of the enzyme indicates that $C_i$ is an inhibitor for the enzyme.

In some embodiments, the cell library enriched for expression of peptide display scaffolds is produced by fluorescence activated cell sorting of cells exhibiting the D signal. In certain embodiments, detecting the presence or absence of the D signal is by fluorescence activated cell sorting. In some embodiments, the TM protein is a bacterial outer membrane protein. In some embodiments, the peptide display scaffold further comprises a linker between $C_i$ and TM. In some embodiments, D is an affinity ligand, such as a streptavadin binding peptide, a monocytic adaptor protein (MONA) binding peptide, or a T7 binding peptide.

The present invention also provides a peptide display scaffold, including:

[$D_1$-$C_1$]-TM-[$D_2$]

wherein TM is a transmembrane protein; $C_1$ is a first candidate peptide; and $D_1$ and $D_2$ are first and second detectable moieties, wherein $D_1$ and $D_2$ are not the same and wherein when $D_1$ provides a detectable signal $D_2$ does not provide a detectable signal; and wherein when the peptide display scaffold is expressed in a cell, $D_1$-$C_1$ and $D_2$ are accessible at a surface of the cell outermembrane.

In some embodiments, the peptide display scaffold further includes at least one linker, wherein the linker is between $C_1$ and TM or $D_2$ and TM. In some embodiments, the TM protein is a bacterial outer membrane protein. In some embodiments, the peptide display scaffold further comprises a linker between $C_i$ and TM. In some embodiments, $D_1$ and $D_2$ are affinity ligands, such as a streptavadin binding peptide, a monocytic adaptor protein (MONA) binding peptide, or a T7 binding peptide.

In certain embodiments, the peptide display scaffold further includes a $C_2$ between TM and $D_2$, wherein the peptide display scaffold has the formula

[$D_1$-$C_1$]-TM-[$C_2$-$D_2$]

wherein $C_2$ is a second candidate peptide, and $C_1$ and $C_2$ are not the same, and wherein when the peptide display scaffold is expressed in a cell, $D_1$-$C_1$ and $C_1$-$D_2$ are accessible at a surface of the cell outermembrane.

In some embodiments, the peptide display scaffold further includes at least one linker, wherein the linker is between $C_1$ and TM or $C_2$ and TM. In some embodiments, the TM protein is a bacterial outer membrane protein. In some embodiments, the peptide display scaffold further comprises a linker between $C_i$ and TM. In some embodiments, $D_1$ and $D_2$ are affinity ligands, such as a streptavadin binding peptide, a monocytic adaptor protein (MONA) binding peptide, or a T7 binding peptide.

The present invention also provides a method for identifying a peptide substrate for an enzyme, by contacting a cell with an enzyme, wherein the cell expresses the following a peptide display scaffold

[$D_1$-$C_1$]-TM-[$D_2$]

wherein TM is a transmembrane protein; $C_1$ is a first candidate peptide; and $D_1$ and $D_2$ are first and second detectable moieties, wherein $D_1$ and $D_2$ are not the same and wherein when $D_1$ provides a detectable signal $D_2$ does not provide a detectable signal; and wherein when the peptide display scaffold is expressed in a cell, $D_1$-$C_1$ and $D_2$ are accessible at a surface of the cell outermembrane, wherein prior to contacting the cell with the enzyme, the cell exhibits a $D_1$ signal and does not exhibit a detectable $D_2$ signal; and detecting the presence or absence of a $D_2$ signal, wherein an increase in the $D_2$ signal indicates that at least one cell of the cell library expresses a candidate peptide that is a substrate for the enzyme.

In certain embodiments, the detecting the presence or absence of the $D_2$ signal is by fluorescence activated cell sorting. In some embodiments, an increase in the $D_2$ signal relative to the $D_1$ signal in the absence of the enzyme indicates that the cell expresses a candidate peptide that interacts with the enzyme. In other embodiments, an increase in the $D_2$ signal relative to the $D_1$ signal indicates that the cell expresses a candidate peptide that is a substrate for the enzyme.

In certain embodiments, C is [A-$C_S$] or [$C_S$-A] wherein A is an allosteric regulator for the enzyme and $C_S$ is a candidate substrate for the enzyme, and wherein an increase in the $D_2$ signal indicates that the cell expresses a candidate peptide that is a substrate for the enzyme.

The present invention also provides a method for identifying a peptide ligand of an enzyme, by contacting a cell with an enzyme, wherein the cell expresses the following a peptide display scaffold

[$D_1$-$C_1$]-TM-[$C_2$-$D_2$]

wherein $C_2$ is a second candidate peptide, and $C_1$ and $C_2$ are not the same, and wherein when the peptide display scaffold is expressed in a cell, $D_1$-$C_1$ and $C_1$-$D_2$ are accessible at a surface of the cell outermembrane, and wherein when $D_1$ is present $D_2$ does not provide a detectable signal; detecting the presence or absence of a $D_1$ signal and a $D_2$ signal, wherein said detecting indicates whether $C_2$ is a peptide ligand for the enzyme.

In some embodiments, the detecting the presence or absence of the $D_1$ signal and the $D_2$ signal is by fluorescence activated cell sorting. In certain embodiments, when $C_1$ is a substrate for the enzyme $C_2$ is a candidate inhibitor for the enzyme, a change in the $D_2$ signal relative to the $D_1$ signal indicates that $C_2$ is an inhibitor for the enzyme. In other embodiments, when $C_1$ is an allosteric regulator for the enzyme and $C_2$ is a candidate substrate, a change in the $D_2$ signal relative to the $D_1$ signal indicates that $C_2$ is a substrate for the enzyme.

The present invention also provides a method for identifying a peptide inhibitor for an enzyme, by contacting a cell expressing a peptide display scaffold with an enzyme, wherein the peptide display scaffold includes:

[$D_1$-S-$C_i$]-TM-[$D_2$]

wherein TM is a transmembrane protein; S is a substrate for the enzyme $C_i$ is a candidate inhibitor peptide; and $D_1$ and $D_2$ are first and second detectable moieties, wherein $D_1$ and $D_2$ are different, and wherein prior to contacting the cell with the enzyme, the cell exhibits a $D_1$ and does not exhibit a detectable $D_2$ signal; and detecting the presence or absence of a $D_1$ signal and a $D_2$ signal, wherein maintenance of the $D_1$ signal relative to the $D_2$ signal indicates that $C_i$ is an inhibitor for the enzyme.

In some embodiments, the cell library enriched for expression of peptide display scaffolds is produced by fluorescence activated cell sorting of cells exhibiting the $D_1$ signal. In some embodiments, the detecting the presence or absence of the $D_1$ signal and the $D_2$ signal is by fluorescence activated cell sorting. In some embodiments, the peptide display scaffold further includes a linker between C and TM. In some embodiments, the TM protein is a bacterial outer membrane protein. In certain embodiments, $D_1$ and $D_2$ are affinity ligands, such as such as a streptavadin binding peptide, a monocytic adaptor protein (MONA) binding peptide, or a T7 binding peptide.

The present invention also provides nucleic acids encoding the peptide display scaffolds as well as expression vectors encoding the peptide display scaffolds. In addition, the present invention provides a host cell including a nucleic acid molecule encoding a peptide display scaffold as well as kits including an expression vector encoding a peptide display scaffold.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 5 shows flow cytometric analysis of cells expressing CPX with a caspase-3 cleavage site, a streptavidin tag and a SH3-mona tag before (top panel) and after (bottom panel) caspase-3 incubation. Both populations labeled with SAPE and YPet-Mona. B530/30 channels shows green fluorescence. B576/26 channel shows red fluorescence.

FIG. 14 provides the nucleic acid sequence (SEQ ID NO:08) of an exemplary peptide display scaffold with N- and C-terminal detectable moieties for use in a dual-color system. Nucleotides 1-69 encode a signal sequence for membrane localization, nucleotides 70-84 encode a flexible linker for a sfi I restriction endonuclease site, nucleotides 85-123 encode a streptavidin binding peptide, nucleotides 124-156 encode a flexible linker, nucleotides 157-171 encode randomized candidate peptide, nucleotides 172-201 encode a flexible linker, nucleotides 202-657 encode a bacterial outermembrane protein X (OmpX) sequence, nucleotides 658-675 encode a flexible linker, and nucleotides 676-717 encode a SH3 domain of Mona binding peptide.

FIG. 15 provides the amino acid sequence of the exemplary peptide display scaffold of FIG. 14 with the signal sequence (top panel) (SEQ ID NO:09) and without the signal sequence (bottom panel) (SEQ ID NO:10). The amino acid sequence of the top panel includes: amino acids 1-23 is the signal sequence for membrane localization, amino acids 24-28 is the flexible linker for the sfi I restriction endonuclease site, amino acids 29-41 is the streptavidin binding peptide, amino acids 42-52 is the flexible linker, amino acids 53-57 is the randomized candidate peptide, amino acids 172-67 is the flexible linker, amino acids 202-219 is the OmpX, amino acids 220-225 is the flexible linker, and amino acids 226-238 is the SH3 domain of Mona binding peptide. The amino acid sequence of the bottom panel includes: amino acids 1-5 is the flexible linker for the sfi I restriction endonuclease site, amino acids 6-18 is the streptavidin binding peptide, amino acids 19-29 is the flexible linker, amino acids 30-34 is the randomized candidate peptide, amino acids 35-44 is the flexible linker, amino acids 45-196 is the OmpX, amino acids 197-202 is the flexible linker, and amino acids 203-215 is the SH3 domain of Mona binding peptide.

FIG. 16 provides the nucleic acid sequence (SEQ ID NO:11) of an exemplary peptide display scaffold with an N-terminal detectable moiety for use in a single-color system. Nucleotides 1-69 encode a signal sequence for membrane localization, nucleotides 70-84 encode a flexible linker for sfi I restriction endonuclease site, nucleotides 85-123 encode a streptavidin binding peptide, nucleotides 124-132 encode a flexible linker, nucleotides 133-150 encode a randomized candidate peptide, nucleotides 151-168 encode a flexible linker, and nucleotides 169-627 encode OmpX.

FIG. 17 provides the amino acid sequence of the exemplary peptide display scaffold of FIG. 16 with the signal sequence (top panel) (SEQ ID NO:12) and without the signal sequence (bottom panel) (SEQ ID NO:13). The amino acid sequence of the top panel includes: amino acids 1-23 is the signal sequence, amino acids 24-28 is the flexible linker for the sfi I restriction endonuclease site, amino acids 29-41 is the streptavidin binding peptide, amino acids 42-44 is the flexible linker, amino acids 45-50 is the randomized candidate peptide, amino acids 51-56 is the flexible linker, and amino acids 57-208 is OmpX. The amino acid sequence of the bottom panel includes: amino acids 1-5 is the flexible linker for the sfi I restriction endonuclease site, amino acids 6-18 is the streptavidin binding peptide, amino acids 19-21 is the flexible linker, amino acids 22-27 is the randomized candidate peptide, amino acids 28-33 is the flexible linker, and amino acids 34-186 is OmpX.

DEFINITIONS

Figure 1:
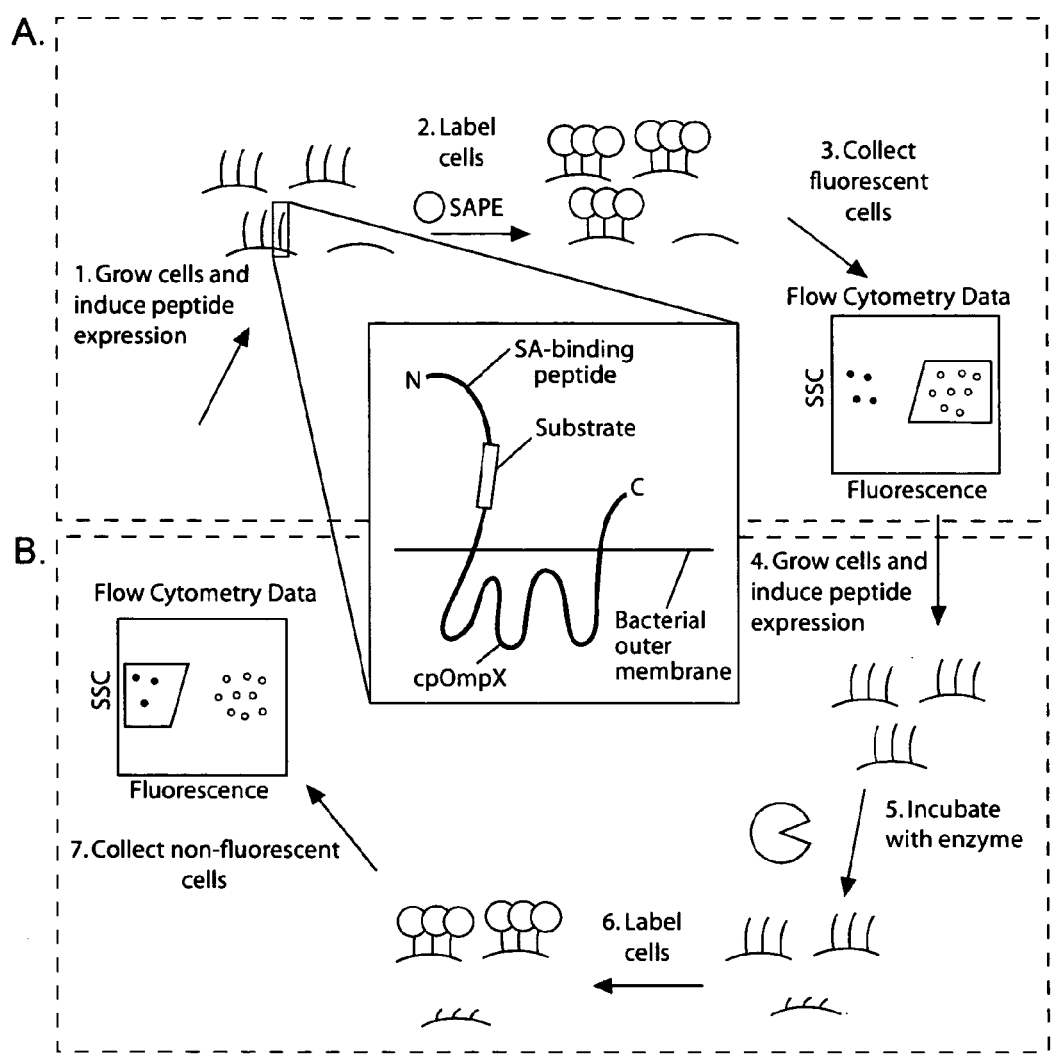
FIG. 1 shows a schematic method of screening Cellular Libraries of Peptide Sequences (CLiPS). Panel A shows an initial enrichment step where cells are screened for those that properly display the candidate peptides in the display scaffolds. A detectable moiety is added to a culture of cells and only those cells that display the reporter substrates on the surface of the cell as fusions to the N-terminus of circularly-permuted outer membrane protein OmpX (CPX). Panel B shows a detection step where the enriched cells are contacted with an enzyme and substrate cleavage is detected by flow cytometry. Substrate libraries are screened by depleting the library pool of clones that do not display a peptide and then enriching clones with hydrolyzed substrates.

Unless defined otherwise, all technical and scientific terms used herein have the same meaning as commonly understood by those of ordinary skill in the art to which this invention pertains. Any methods and materials similar or equivalent to those described herein can be used in the practice or testing of the present invention, the described methods and materials being exemplary.

The terms "substantially pure" or "isolated," when referring to proteins and polypeptides denote those polypeptides that are separated from proteins or other contaminants with which they are naturally associated. A protein or polypeptide is considered substantially pure when that protein makes up greater than about 50% of the total protein content of the composition containing that protein, and typically, greater than about 60% of the total protein content. More typically, a substantially pure or isolated protein or polypeptide will make up at least 75%, more preferably, at least 90%, of the total protein. Preferably, the protein will make up greater than about 90%, and more preferably, greater than about 95% of the total protein in the composition.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences that are immunologically identifiable with a polypeptide encoded by the sequence.

A "vector" is capable of transferring gene sequences to target cells. Typically, "vector construct," "expression vector," and "gene transfer vector," mean any nucleic acid construct capable of directing the expression of a gene of interest in a host cell. Thus, the term includes cloning, and expression vehicles, as well as integrating vectors.

As used herein, "recombinant" has the usual meaning in the art, and refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide.

The term "recombinant" when used with reference to a cell indicates that the cell contains a heterologous nucleic acid, or expresses a peptide or protein encoded by such a heterologous nucleic acid, and usually provides for replication of such heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "heterologous sequence", "heterologous nucleic acid", "heterologous polypeptide" or "heterologous amino acid sequence" as used herein, is one that originates from a source foreign to the particular host cell, or, if from the same source, is modified from its original form. Thus, a heterologous nucleic acid in a host cell includes nucleic acid that, although being endogenous to the particular host cell, has been modified (e.g., so that it encodes an amino acid sequence different from that of a naturally-occurring or parent nucleic acid, to a nucleic acid to provide a sequence not normally found in the host cell, and the like). Modification of the heterologous sequence can be accomplished by a variety of methods, e.g., by treating the DNA with a restriction enzyme to generate a DNA fragment that is capable of being operably linked to the promoter or by operably linking the DNA to a heterologous promoter to provide an expression cassette that is not endogenous to the host cell. Techniques such as site-directed mutagenesis are also useful for modifying a heterologous nucleic acid.

The term "operably linked" refers to functional linkage between nucleic acids to provide a desired activity, e.g., a functional linkage between a nucleic acid expression control sequence (such as a promoter, signal sequence, or array of transcription factor binding sites) and a second polynucleotide, wherein the expression control sequence affects transcription and/or translation of the second polynucleotide. "Operably linked" in the context of a polypeptide refers to a functional linkage between amino acid sequences (e.g., of different domains) to provide for a described activity of the polypeptide (e.g., a nuclear localization signal is operably linked to a heterologous amino acid sequence to provide to association of the fusion protein with the nucleus in a mammalian cell).

A "recombinant expression cassette" or simply an "expression cassette" is a nucleic acid construct, generated recombinantly and/or synthetically, that has control elements that are capable of affecting expression of a structural gene that is operably linked to the control elements in hosts compatible with such sequences. Expression cassettes include at least promoters and optionally, transcription termination signals. Typically, the recombinant expression cassette includes at least a nucleic acid to be transcribed and a promoter. Additional factors necessary or helpful in effecting expression can also be used as described herein. For example, transcription termination signals, enhancers, and other nucleic acid sequences that influence gene expression, can also be included in an expression cassette.

As used herein, "contacting" has its normal meaning and refers to combining two or more entities (e.g., two proteins, an enzyme and a cell, a cell and a candidate agent, etc.). Contacting can occur in a test tube or other container (e.g., combining of two or more agents [e.g., an enzyme and a cell expressing a peptide display scaffold]), in a cell (e.g., two polypeptides can be contacted in a cell by coexpression in the cell, of recombinant polynucleotides encoding the two polypeptides), or in a cell-free-system (e.g., combining an enzyme with a cell membranes, synthetic membrane, or other membranes for presentation of a peptide display scaffold without the need for intact cells.

As used herein, a "ligand" refers to a molecule(s) that binds to a binding partner molecule(s), e.g., a substrate, inhibitor, or allosteric regulator binding to an enzyme, and includes natural and synthetic biomolecules, such as proteins, polypeptides, peptides, nucleic acid molecules, carbohydrates, sugars, lipids, lipoproteins, small molecules, natural and synthetic organic and inorganic materials, synthetic polymers, and the like. The binding of the ligand to a binding partner may be at the active site, e.g., binding of a substrate or inhibitor with an enzyme, or at a site other than the active site (a "secondary site") e.g., binding of an allosteric regulator or non-competitive inhibitor with an enzyme.

"Binding" as used herein generally refers to a covalent or non-covalent interaction between two molecules (e.g., a substrate and an enzyme, and inhibitor and an enzyme, and allosteric regulator and an enzyme), which binding is usually specific.

As used herein, "specifically binds" or "binds specifically" refers to the character of an enzyme, receptor or other binding partner which recognizes and interacts with a ligand (e.g., substrate, inhibitor, allosteric regulator) but does not substantially recognize and interact with other molecules in a sample under given conditions.

As used herein, "fluorescent group" refers to a molecule that, when excited with light having a selected wavelength, emits light of a different wavelength. Fluorescent groups may also be referred to as "fluorophores".

The term "detecting" or "assessing" includes any form of qualitative or quantitative measurement, and includes determining if an element is present or absent. The terms "determining", "measuring", "evaluating", "assessing" and "assaying" are used interchangeably and includes quantitative and qualitative determinations. Assessing may be relative or absolute. "Assessing the presence of" includes determining the amount of something present, and/or determining whether it is present or absent. As used herein, the terms "detecting," "determining," "measuring," and "assessing," and "assaying" are used interchangeably and include both quantitative and qualitative determinations.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

DETAILED DESCRIPTION OF THE INVENTION

The present invention provides compositions including peptide display scaffolds that present at least one candidate peptide and at least one detectable moiety in at least one of the N-terminal and C-terminal candidate peptide presenting domains that when expressed in a cell are accessible at a surface of the cell outermembrane. In addition, the present invention also provides kits and methods for screening a library of cells presenting the candidate peptides in peptide display scaffolds to identify a ligand for an enzyme.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the compounds" includes reference to one or more compounds and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Introduction

The present invention provides compositions and methods for screening a library of cells presenting candidate peptides in peptide display scaffolds to identify a peptide that interacts with an enzyme. The cellular libraries of peptide sequences (CLiPS) disclosed herein provide a qualitative and/or quantitative approach to identify a peptide ligand for an enzyme as well as determining the specificity of the peptide that interacts with an enzyme (e.g., a substrate for the enzyme or an inhibitor of the activity of the enzyme).

The inventors have found that in contrast to phagemid or phage libraries displaying candidate peptides, the peptide display scaffolds disclosed herein provide display of up to about $10^3$-$10^4$ copies of the candidate peptide on the surface of a single cell, thereby enabling identification of a peptide ligand for an enzyme as well as providing for quantitative and qualitative measurement of the interaction between the candidate peptide displayed in the peptide display scaffold and the enzyme.

The methods are based on the use of single-cell fluorescence as an indicator of substrate conversion enabling library screening. Likewise, whole-cell fluorescence measurements enable calculation of substrate cleavage kinetics for isolated clones, eliminating the need to prepare soluble substrates using synthetic or recombinant methods. Finally, the cell libraries disclosed herein can be manipulated with relative ease and amplified indefinitely by growth without introducing measurable library bias. As such, this approach enables generation of candidate peptide libraries of arbitrary amino acid compositions and lengths that are self renewing. Given the simplicity of library manipulation and screening, CLiPS provides a scalable solution to rapidly identify candidate peptides as well as characterize enzymes, such as proteases.

The following description provides guidance for making and using the compositions of the invention, and for carrying out the methods of the invention.

Peptide Display Scaffolds

In general, the peptide display scaffolds include a transmembrane protein having N-terminal and C-terminal candidate peptide presenting domains that are accessible at a surface of the cell outermembrane, i.e. are displayed at the extracellular surface of the cell outer membrane. The peptide display scaffolds include at least one N-terminal and C-terminal domain and at least one N-terminal and C-terminal detectable domains. When expressed in a cell, the peptide display scaffolds display the candidate peptides as terminal fusion proteins thereby providing a more accurate measurement of the interaction capability between the candidate peptide and the tested enzyme. In other words, the measurement of the interaction between terminally displayed candidate peptides and enzymes provided by the present peptide display scaffolds more closely approximates values obtained from measurements of the same interaction in solution with soluble peptides. The peptide display scaffolds are described in greater detail below.

The peptide display scaffolds allow the display of candidate peptides at either the N-terminal domain or the C-terminal domain as well as simultaneous display of a different peptide at each of the N-terminal domain and the C-terminal domain.

In some embodiments, the peptide display scaffolds are generally described by Formula (I) as follows:

$$[D-C]\text{-TM} \qquad (I)$$

wherein TM is a transmembrane protein, C is a candidate peptide; and D is a detectable moiety (e.g., affinity tag), wherein when the peptide display scaffold is expressed in a cell, D-C is accessible at a surface of the cell outermembrane (e.g., D-C is on the extracellular surface of the cell). It is to be understood that the D-C may be at either the N-terminus or the C-terminus.

In certain embodiments, C is [S-$C_i$] or [$C_i$-S] and the peptide display scaffold is generally described by Formula (II) or Formula (III) as follows:

$$[D\text{-}S\text{-}C_i]\text{-TM} \qquad (II)$$

$$[D\text{-}C_i\text{-}S]\text{-TM} \qquad (III)$$

wherein S is a known substrate for the enzyme, $C_i$ is a candidate inhibitor for the enzyme, TM is a transmembrane protein, and D is a detectable moiety (e.g., affinity tag), wherein when the peptide display scaffold is expressed in a cell, D-S-$C_i$ and D-$C_i$-S is accessible at a surface of the cell outermembrane (e.g., $D_1$-S-$C_i$ are $D_1$-$C_i$-S are on the extracellular surface of the cell). It is to be understood that the D-S-$C_i$ (or D-$C_i$-S) may be at either the N-terminus or the C-terminus.

In other embodiments, C is [A-$C_S$] or [$C_S$-A] and the peptide display scaffold is generally described by Formula (IV) or Formula (V) as follows:

$$[D\text{-}A\text{-}C_S]\text{-TM} \qquad (IV)$$

$$[D\text{-}C_S\text{-}A]\text{-TM} \qquad (V)$$

wherein A is an allosteric regulator for the enzyme, $C_S$ is a candidate substrate for the enzyme, TM is a transmembrane protein, and D is a detectable moiety (e.g., affinity tag), wherein when the peptide display scaffold is expressed in a cell, $D_1$-A-$C_S$ and $D_1$-$C_S$-A are accessible at a surface of the cell outermembrane (e.g., $D_1$-A-$C_S$ and $D_1$-$C_S$-A are on the extracellular surface of the cell). It is to be understood that the $D_1$-A-$C_S$ (or $D_1$-$C_S$-A) may be at either the N-terminus or the C-terminus.

Figure 11:
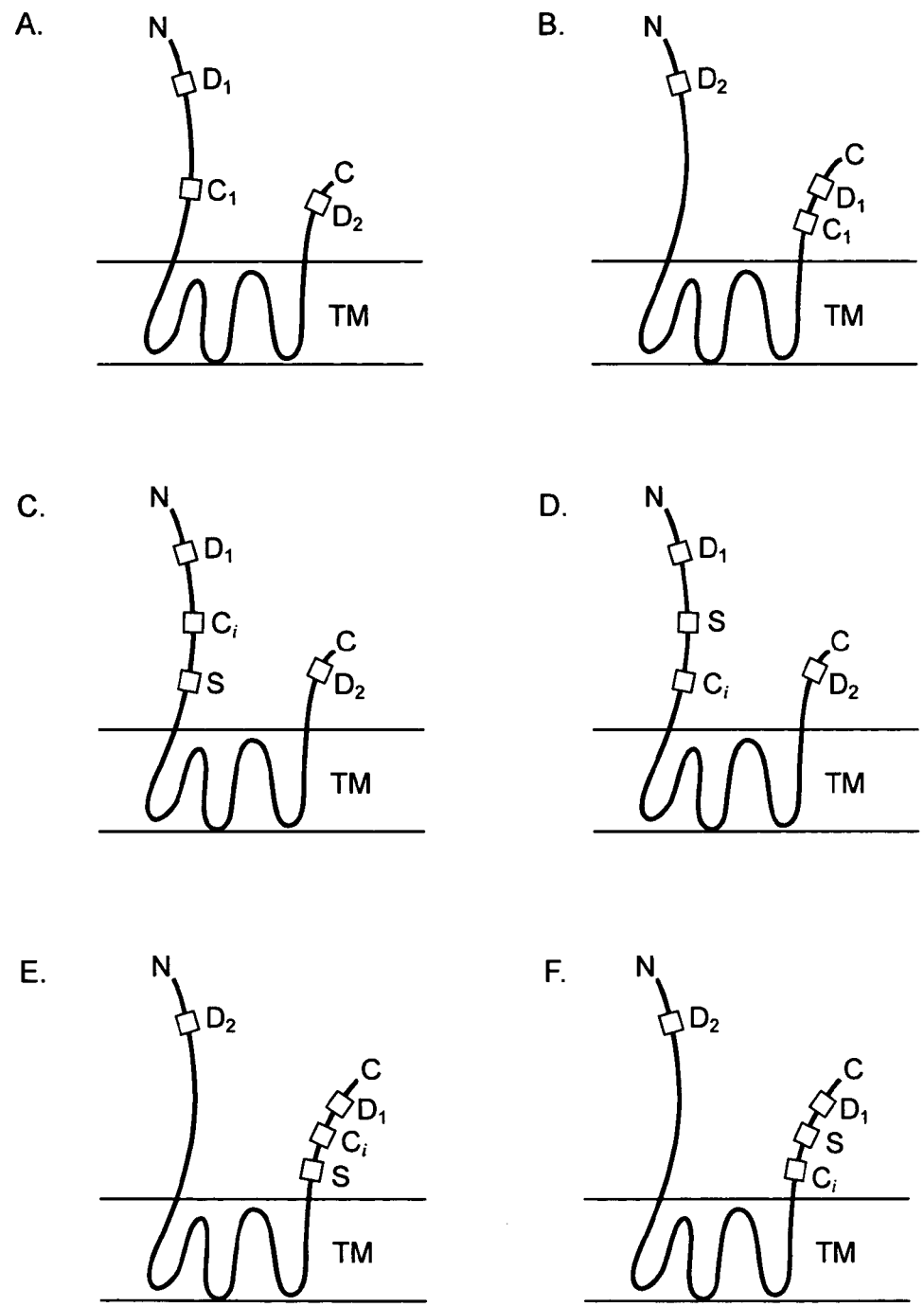
FIG. 11 shows schematics of exemplary peptide display scaffolds. Panel A shows an exemplary peptide display scaffold including a transmembrane protein (TM), an N-terminal domain including a candidate peptide (C) and a first detectable moiety ($D_1$), and a C-terminal domain including a second detectable moiety ($D_2$). Panel B shows an exemplary peptide display scaffold including a transmembrane protein (TM), a C-terminal domain including a candidate peptide (C) and a first detectable moiety ($D_1$), and an N-terminal domain including a second detectable moiety ($D_2$). Panels C and D show exemplary peptide display scaffolds including a transmembrane protein (TM), an N-terminal domain including a candidate inhibitor peptide ($C_i$), a substrate for the enzyme (S) and a first detectable moiety ($D_1$), and a C-terminal domain including a second detectable moiety ($D_2$). Panels E and F show exemplary peptide display scaffolds including a transmembrane protein (TM), a C-terminal domain including a candidate inhibitor peptide ($C_i$), a substrate for the enzyme (S) and a first detectable moiety ($D_1$), and an N-terminal domain including a second detectable moiety ($D_2$).

In some embodiments, the peptide display scaffolds are generally described by Formula (VI) as follows:

[$D_1$-C]-TM-[$D_2$]     (VI)

wherein TM is a transmembrane protein, C is a candidate peptide; and $D_1$ and $D_2$ are first and second detectable moieties (e.g., affinity tags), wherein $D_1$ and $D_2$ are different and wherein when the peptide display scaffold is expressed in a cell, $D_1$-C and $D_2$ are accessible at a surface of the cell outermembrane (e.g., $D_1$-C and $D_2$ are on the extracellular surface of the cell) and wherein when $D_1$ is present (e.g., provides a detectable signal by binding of an affinity ligand labeled fluorescent moiety) $D_2$ does not provide a detectable signal (FIG. 11, panels A and B). It is to be understood that the $D_1$-C may be at either the N-terminus or the C-terminus and $D_2$ may be at either the N-terminus or the C-terminus. For example, when the $D_1$-C is at the N-terminus the $D_2$ is at the C-terminus (FIG. 11, panel A) and when the $D_1$-C is at the C-terminus the $D_2$ is at the N-terminus (FIG. 11, panel B).

In certain embodiments, C is [S-$C_i$] or [$C_i$-S] and the peptide display scaffold is generally described by Formula (VII) or Formula (VIII) as follows:

[$D_1$-S-$C_i$]-TM-[$D_2$]     (VII)

[$D_1$-$C_i$-S]-TM-[$D_2$]     (VIII)

wherein S is a substrate for the enzyme, $C_i$ is a candidate inhibitor for the enzyme, TM is a transmembrane protein, and $D_1$ and $D_2$ are first and second detectable moieties (e.g., affinity tags), wherein $D_1$ and $D_2$ are different and wherein when the peptide display scaffold is expressed in a cell, $D_1$-S-$C_i$, $D_1$-$C_i$-S, and $D_2$ are accessible at a surface of the cell outermembrane (e.g., $D_1$-S-$C_i$, $D_1$-$C_i$-S, and $D_2$ are on the extracellular surface of the cell) and wherein when $D_1$ is present (e.g., provides a detectable signal by binding of an affinity ligand labeled fluorescent moiety) $D_2$ does not provide a detectable signal (FIG. 11, panels C, D, E, and F). It is to be understood that the $D_1$-S-$C_i$ (or $D_1$-$C_i$-S) may be at either the N-terminus or the C-terminus and $D_2$ may be at either the N-terminus or the C-terminus. For example, when the $D_1$-S-$C_i$ (or $D_1$-$C_i$-S) is at the N-terminus the $D_2$ is at the C-terminus (FIG. 11, panels C and D) and when the $D_1$-S-$C_i$ (or $D_1$-$C_i$-S) is at the C-terminus the $D_2$ is at the N-terminus (FIG. 11, panels E and F).

In other embodiments, C is [A-$C_S$] or [$C_S$-A] and the peptide display scaffold is generally described by Formula (IX) or Formula (X) as follows:

[$D_1$-A-$C_S$-TM-$D_2$]     (IX)

Figure 12:
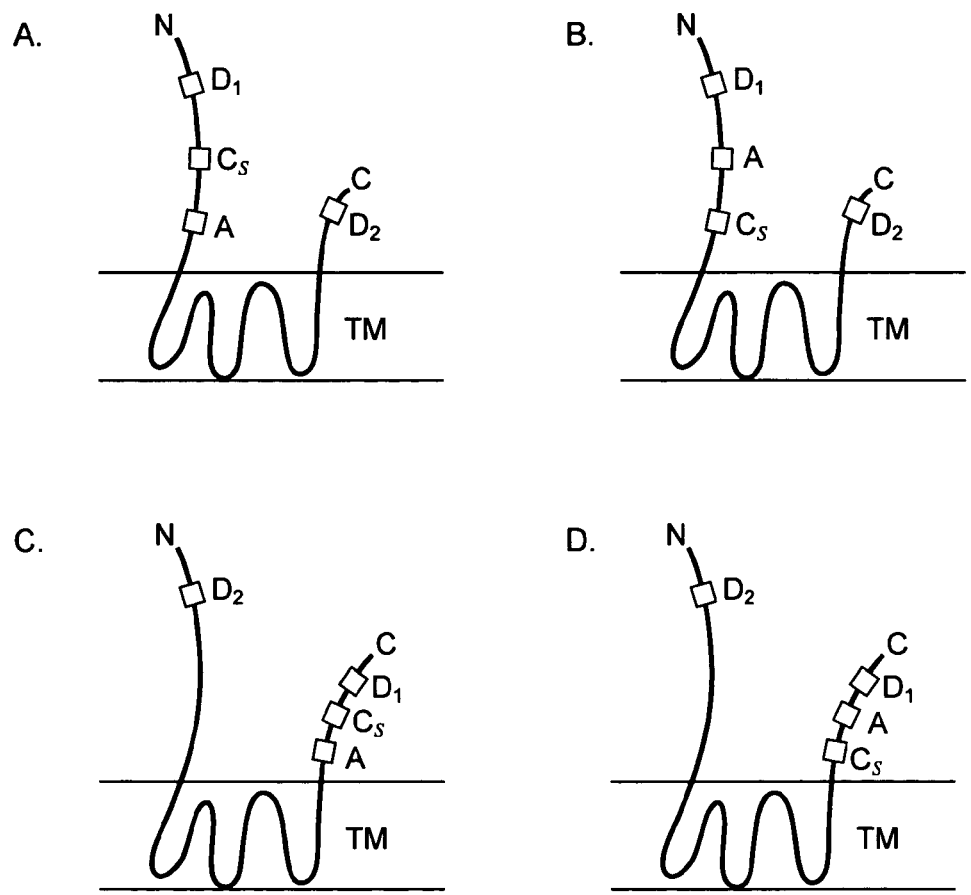
FIG. 12 shows schematics of exemplary peptide display scaffolds. Panels A and B show exemplary peptide display scaffolds including a transmembrane protein (TM), an N-terminal domain including a candidate substrate peptide ($C_S$), an allosteric regulator for the enzyme (A) and a first detectable moiety. ($D_1$), and a C-terminal domain including a second detectable moiety ($D_2$). Panels C and D show exemplary peptide display scaffolds including a transmembrane protein (TM), a C-terminal domain including a candidate substrate peptide ($C_S$), an allosteric regulator for the enzyme (A) and a first detectable moiety ($D_1$), and an N-terminal domain including a second detectable moiety ($D_2$).

[$D_1$-$C_S$-A]-TM-[$D_2$]     (X)

wherein A is an allosteric regulator for the enzyme, $C_S$ is a candidate substrate for the enzyme, TM is a transmembrane protein, and $D_1$ and $D_2$ are first and second detectable moieties (e.g., affinity tags), wherein $D_1$ and $D_2$ are different and wherein when the peptide display scaffold is expressed in a cell, $D_1$-A-$C_S$, $D_1$-$C_S$-A, and $D_2$ are accessible at a surface of the cell outermembrane (e.g., $D_1$-A-$C_S$, $D_1$-$C_S$-A, and $D_2$ are on the extracellular surface of the cell) and wherein when $D_1$ is present $D_2$ does not provide a detectable signal (FIG. 12, panels A, B, C, and D). It is to be understood that the $D_1$-A-$C_S$ (or $D_1$-$C_S$-A) may be at either the N-terminus or the C-terminus and $D_2$ may be at either the N-terminus or the C-terminus. For example, when the $D_1$-A-$C_S$ (or $D_1$-$C_S$-A) is at the N-terminus the $D_2$ is at the C-terminus (FIG. 12, panels A and B) and when the $D_1$-A-$C_S$ (or $D_1$-$C_S$-A) is at the C-terminus the $D_2$ is at the N-terminus (FIG. 12, panels C and D).

Figure 13:
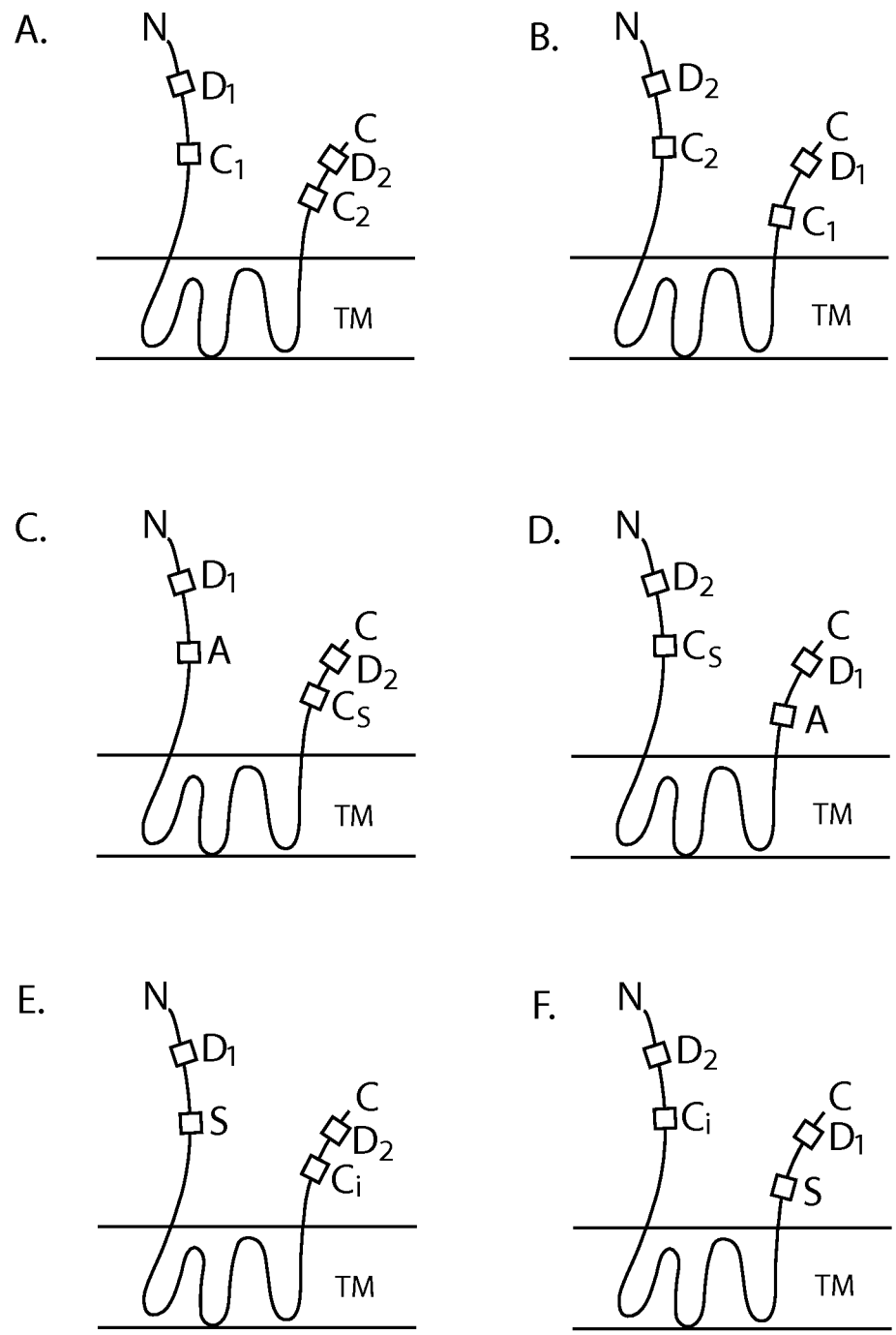
FIG. 13 shows schematics of exemplary peptide display scaffolds. Panel A shows an exemplary peptide display scaffold including a transmembrane protein (TM), an N-terminal domain including a first candidate peptide ($C_1$) and a first detectable moiety ($D_1$), and a C-terminal domain including a second candidate peptide ($C_2$) and a second detectable moiety ($D_2$). Panel B shows an exemplary peptide display scaffold including a transmembrane protein (TM), a C-terminal domain including a first candidate peptide ($C_1$) and a first detectable moiety ($D_1$), and an N-terminal domain including a second candidate peptide ($C_2$) and a second detectable moiety ($D_2$). Panel C shows an exemplary peptide display scaffold including a transmembrane protein (TM), an N-terminal domain including an allosteric regulator (A) and a first detectable moiety ($D_1$), and a C-terminal domain including a candidate substrate ($C_S$) and a second detectable moiety ($D_2$). Panel D shows an exemplary peptide display scaffold including a transmembrane protein (TM), a C-terminal domain including an allosteric regulator (A) and a first detectable moiety ($D_1$), and an N-terminal domain including a candidate substrate ($C_S$) and a second detectable moiety ($D_2$). Panel E shows an exemplary peptide display scaffold including a transmembrane protein (TM), an N-terminal domain including a known substrate (S) and a first detectable moiety ($D_1$), and a C-terminal domain including a candidate inhibitor ($C_i$) and a second detectable moiety ($D_2$). Panel F shows an exemplary peptide display scaffold including a transmembrane protein (TM), a C-terminal domain including a known substrate (S) and a first detectable moiety ($D_1$), and an N-terminal domain including a candidate inhibitor ($C_i$) and a second detectable moiety ($D_2$).

In other embodiments, the peptide display scaffolds are generally described by Formula (XI) as follows:

[$D_1$-$C_1$]-TM-[$C_2$-$D_2$]     (XI)

wherein TM is a transmembrane protein, $C_1$ and $C_2$ are first and second candidate peptides, wherein $C_1$ and $C_2$ are not the same; $D_1$ and $D_2$ are first and second detectable moieties (e.g., affinity tags), wherein $D_1$ and $D_2$ are not the same; and wherein when the peptide display scaffold is expressed in a cell, $D_1$-$C_1$ and $C_2$-$D_2$ are accessible at a surface of the cell outermembrane (e.g., $D_1$-$C_1$ and $C_2$-$D_2$ are on the extracellular surface of the cell) (FIG. 13, panels A and B). It is to be understood that the $D_1$-$C_1$ may be at either the N-terminus or the C-terminus and $C_2$-$D_2$ may be at either the N-terminus or the C-terminus. For example, when the $D_1$-$C_1$ is at the N-terminus the $C_2$-$D_2$ is at the C-terminus (FIG. 13, panel A) and when the $D_1$-$C_1$ is at the C-terminus the $C_2$-$D_2$ is at the N-terminus (FIG. 13, panel B). In certain embodiments, $C_1$ is an allosteric regulator and $C_2$ is a candidate substrate (FIG. 13, panels C and D). In other embodiments, $C_1$ is a known substrate and $C_2$ is a candidate inhibitor (FIG. 13, panels E and F).

Exemplary transmembrane proteins (TM) and methods for modifying the same for use with the peptide display scaffolds are described in greater detail in U.S. patent application Ser. No. 10/920,244, the disclosure of which is incorporated herein by reference in its entirety. It should be noted that any transmembrane protein localized on the outer surface of a biological entity, presenting one or more loop sequences accessible on the cell surface and the like may be modified in order to generate and present a C-terminus, an N-terminus, or both at the outer surface of a biological entity and fused with a passenger polypeptide is suitable for use with the peptide display scaffolds. Transmembrane proteins suitable for rearrangement for terminal fusion display from an internal loop include bacterial outer membrane proteins (Omps), such as OmpA, OmpX, OmpT, OmpC, OmpS, LamB, TraT, IgA protease, and the like, and other extracellular structural adhesion proteins of bacteria, such as FimH, PapA, PapG, and the like, transporter proteins of mammalian cells such as MCAT-1, capsid and coat proteins of bacteriophage (e.g., gpVIII from M13) and the envelope, and capsid proteins of eukaryotic cell viruses (e.g., HIV env, retroviral env, AAV capsid protein), and the like.

In certain embodiments, the peptide display scaffolds further include a flexible linker between the transmembrane protein (TM) and one or both of the N-terminal and C-terminal domains, such as $D_1$-C, $D_1$-S-$C_i$, $D_1$-$C_i$-S, $D_1$-A-$C_S$, $D_1$-$C_S$-A, $D_2$, $D_1$-$C_1$ and $C_2$-$D_2$. For example, in some embodiments, the peptide display scaffold further includes a linker between C and TM or at least one linker between $C_1$ and TM or $C_2$ and TM.

A linker suitable for use with the peptide display scaffold will be one that provides flexibility to the N-terminal or C-terminal domains when present and does not interfere with the presentation of the candidate peptide on the surface of the cell. The flexible linker will be variable length, such as from about 3 amino acids to about 25 amino acids, including about 4 amino acids to about 23 amino acids, about 5 amino acids to about 20 amino acids, about 6 amino acids to about 18 amino acids, about 7 amino acids to about 16 amino acids, about 8 amino acids to about 14 amino acids, and about 9 amino acids to about 12 amino acids.

Exemplary flexible linkers include glycine polymers $(G)_n$, glycine-serine polymers (including, for example, $(GS)_n$, (GSGGS)$_n$ (SEQ ID NO:14) and (GGGS)$_n$ (SEQ ID NO:15), where n is an integer of at least one), glycine-alanine polymers, alanine-serine polymers, and other flexible linkers such as the tether for the shaker potassium channel, and a large variety of other flexible linkers, as will be appreciated by those in the art. Glycine and glycine-serine polymers are of interest since both of these amino acids are relatively unstructured, and therefore may be able to serve as a neutral tether between components. Glycine polymers are of particular interests glycine accesses significantly more phi-psi space than even alanine, and is much less restricted tan residues with longer side chains (see Scheraga, Rev. Computational Chem. 11173-142 (1992)). Exemplary flexible linkers include, but are not limited Gly-Gly-Ser-Gly-Gly (SEQ ID NO:16), Gly-Ser-Gly-Ser-Gly (SEQ ID NO:17), Gly-Ser-Gly-Gly-Gly (SEQ ID NO:18), Gly-Gly-Gly-Ser-Gly (SEQ ID NO:19), Gly-Ser-Ser-Ser-Gly (SEQ ID NO:20), and the like.

As described above, the candidate peptides (C) are generally situated on a cell surface accessible region of a peptide display scaffold, such that the candidate peptides can interact with extracellular or cell surface-associated elements. The candidate peptides can be screened to identify a peptide ligand for the tested enzyme. As used herein, "ligand" or "peptide ligand" refer to a molecule(s) that binds (e.g., by covalent or non-covalent interaction) to a binding partner molecule(s), e.g., a substrate, inhibitor, or allosteric regulator binding to an enzyme. The binding of the ligand to the binding partner may be at the active site, e.g., binding of a substrate or inhibitor with an enzyme, or at another secondary site e.g., binding of an allosteric regulator or non-competitive inhibitor with an enzyme. As such, exemplary candidate peptides include candidate enzyme substrates, candidate enzyme inhibitors, and the like.

Candidate peptides can range from about 2 amino acids in length to about 100 amino acids, including polypeptides ranging from about 2 to about 50, with from about 2 to about 30 being of particular interest, such as from about 2 to about 10 amino acids in length. Generally, candidate peptides may be about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In general, the candidate peptide are randomized, either fully randomized or are biased in their randomization, e.g. in nucleotide/residue frequency generally or per position. By "randomized" is meant that each candidate peptide consists of essentially random amino acids. As is more fully described below, the candidate peptides, or candidate nucleic acids encoding the same, are chemically synthesized, and thus may incorporate any amino acid or nucleotide at any position. The synthetic process can be designed to generate randomized peptides, to allow the formation of all or most of the possible combinations over the length of the peptide, thus forming a library of randomized candidate peptides.

As such, in some embodiments, the library of candidate peptides is fully randomized, with no sequence preferences or constants at any position. In other embodiments, the library of candidate peptides is biased. That is, some positions within the sequence are either held constant, or are selected from a limited number of possibilities. For example, in one embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

The first and second detectable moieties ($D_1$ and $D_2$) can be any detectable label that provides a detectable signal that can be assessed qualitatively (positive/negative) and quantitatively (comparative degree of fluorescence). As noted in greater detail above, the first and second detectable moieties ($D_1$ and $D_2$) of a peptide display scaffold are different. As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, streptavidin or haptens) and the like. The term "fluorescer" refers to a substance or a portion thereof which is capable of exhibiting fluorescence in the detectable range. Exemplary detectable moieties suitable for use with the peptide display scaffolds include, affinity tags and fluorescent proteins.

The term "affinity tag" is used herein to denote a peptide segment that can be attached to peptide display scaffolds at position D (e.g., $D_1$ or $D_2$) that can be detected using a molecule that binds the affinity tag and provides a detectable signal (e.g., a fluorescent compound or protein). In principal, any peptide or protein for which an antibody or other specific binding agent is available can be used as an affinity tag. Exemplary affinity tags suitable for use include, but are not limited to, a monocytic adaptor protein (MONA) binding peptide, a T7 binding peptide, a streptavidin binding peptide, a polyhistidine tract, protein A (Nilsson et al., EMBO J. 4:1075 (1985); Nilsson et al., Methods Enzymol. 198:3 (1991)), glutathione S transferase (Smith and Johnson, Gene 67:31 (1988)), Glu-Glu affinity tag (Grussenmeyer et al., Proc. Natl. Acad. Sci. USA 82:7952 (1985)), substance P, FLAG peptide (Hopp et al., Biotechnology 6:1204 (1988)), or other antigenic epitope or binding domain. See, in general, Ford et al., Protein Expression and Purification 2:95 (1991). DNA molecules encoding affinity tags are available from commercial suppliers (e.g., Pharmacia Biotech, Piscataway, N.J.).

Any fluorescent polypeptide (also referred to herein as a fluorescent label) well known in the art is suitable for use as a detectable moiety or with an affinity tag of the peptide display scaffolds described herein. A suitable fluorescent polypeptide will be one that can be expressed in a desired host cell, such as a bacterial cell or a mammalian cell, and will readily provide a detectable signal that can be assessed qualitatively (positive/negative) and quantitatively (comparative degree of fluorescence). Exemplary fluorescent polypeptides include, but are not limited to, yellow fluorescent protein (YFP), cyan fluorescent protein (CFP), GFP, mRFP, RFP (tdimer2), HCRED, etc., or any mutant (e.g., fluorescent proteins modified to provide for enhanced fluorescence or a shifted emission spectrum), analog, or derivative thereof. Further suitable fluorescent polypeptides, as well as specific examples of those listed herein, are provided in the art and are well known.

Nucleic Acids Encoding Peptide Display Scaffolds

Also described herein are nucleic acid compositions encoding the peptide display scaffolds described herein. For example, the nucleic acid molecules encode the peptide display scaffolds of Formulas VI-XI. Nucleic acid compositions of particular interest comprise a sequence of DNA having an open reading frame that encodes a peptide display scaffold and is capable, under appropriate conditions, of being expressed and provide display of the candidate peptide at the extracellular surface of the cell outer membrane.

In certain embodiments, the nucleic acid encoding the peptide display scaffolds of Formulas VI-X may further include at least one restriction endonuclease site (e.g., a single endonuclease site or a multiple cloning site (e.g., polylinker)) between $D_1$ and C (or $C_i$, S, $C_S$, A) and at least one restriction endonuclease site (e.g., a single endonuclease site or a multiple cloning site (e.g., polylinker)) between TM and $D_2$. In other embodiments, the nucleic acid encoding the peptide display scaffold of Formula XI may further include at least one restriction endonuclease site (e.g., a single endonuclease site or a multiple cloning site (e.g., polylinker)) between $D_1$ and $C_1$ and at least one restriction endonuclease site (e.g., a single endonuclease site or a multiple cloning site (e.g., polylinker)) between $D_2$ and $C_2$. Also encompassed in this term are nucleic acids that are homologous, substantially similar or identical to the nucleic acids disclosed herein.

In certain embodiments, the nucleic acids may be present in an appropriate vector for extrachromosomal maintenance or for integration into a host genome, as described in greater detail below.

In some embodiments, the vector includes a nucleic acid encoding a peptide display scaffold generally described by Formula (XII) as follows:

$$[D_1\text{-RE}]\text{-TM-}[D_2] \quad (XII)$$

wherein TM is a transmembrane protein, RE is a restriction endonuclease site for insertion of a nucleic acid sequence encoding a candidate peptide; and $D_1$ and $D_2$ are first and second detectable moieties (e.g., affinity tags), wherein $D_1$ and $D_2$ are different.

In certain embodiments, the vector includes a nucleic acid encoding a peptide display scaffold generally described by Formula (XIII) or Formula (XIV) as follows:

$$[D_1\text{-Y-RE}]\text{-TM-}[D_2] \quad (XIII)$$

$$[D_1\text{-RE-Y}]\text{-TM-}[D_2] \quad (XIV)$$

wherein Y is a substrate for the enzyme or an allosteric regulator for the enzyme, RE is a restriction endonuclease site for insertion of a nucleic acid sequence encoding a candidate inhibitor for the enzyme, TM is a transmembrane protein, and $D_1$ and $D_2$ are first and second detectable moieties (e.g., affinity tags), wherein $D_1$ and $D_2$ are different.

In other embodiments, the peptide display scaffolds are generally described by Formula (XV) as follows:

$$[D_1\text{-RE}_1]\text{-TM-}[\text{RE}_2\text{-}D_2] \quad (XV)$$

wherein TM is a transmembrane protein, $RE_1$ and $RE_2$ are first and second restriction endonuclease sites, and $D_1$ and $D_2$ are first and second detectable moieties (e.g., affinity tags), wherein $D_1$ and $D_2$ are different and $RE_1$ and $RE_2$ are different.

Any restriction endonuclease site can be used at RE, $RE_1$, and $RE_2$ that provides for efficient restriction and insertion of a nucleic acid encoding a candidate peptide is suitable for use. Exemplary restriction endonuclease sites suitable for use include, but are not limited to, Not1, BamH1, Hind3, EcoR1, Hpa1, Sal1, Sfi1, Cla1, Rsr2, and the like.

It will be appreciated that in some embodiments it will be desirable to use a single polylinker having at least two more different endonuclease sites at the RE, $RE_1$, and $RE_2$. In such embodiments, the expression vector includes a polylinker at RE, $RE_1$, and $RE_2$ having at least two or more different restriction endonuclease sites (e.g., multiple cloning site). For example, in such embodiments, the vectors encoding the peptide display scaffold includes a polylinker having two or more sites to provide for insertion of a nucleic acid sequence encoding a candidate peptide using a first restriction endonuclease site and allow for excision of the nucleic acid once a specific clone that has been identified as being of particular interest using two flanking restriction endonuclease sites.

The polynucleotides and constructs thereof can be generated synthetically by a number of different protocols known to those of skill in the art. Appropriate polynucleotide constructs are purified using standard recombinant DNA techniques as described in, for example, Sambrook et al., *Molecular Cloning: A Laboratory Manual*, 2nd Ed., (1989) Cold Spring Harbor Press, Cold Spring Harbor, N.Y., and under current regulations described in United States Dept. of HHS, National Institute of Health (NIH) Guidelines for Recombinant DNA Research.

Also provided are constructs comprising the nucleic acids described herein inserted into a vector, where such constructs may be used for a number of different screening applications as described in greater detail below. In some embodiments, a single vector (e.g., a plasmid) will contain nucleic acid coding sequence for a single peptide display scaffold. In other embodiments, a single vector (e.g., a plasmid) will contain nucleic acid coding sequence for a two or more peptide display scaffolds.

Viral and non-viral vectors may be prepared and used, including plasmids, which provide for replication of biosensor-encoding DNA and/or expression in a host cell. The choice of vector will depend on the type of cell in which propagation is desired and the purpose of propagation. Certain vectors are useful for amplifying and making large amounts of the desired DNA sequence. Other vectors are suitable for expression in cells in culture. Still other vectors are suitable for transformation and expression in cells in a whole animal or person. The choice of appropriate vector is well within the skill of the art. Many such vectors are available commercially. To prepare the constructs, the partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Also provided are expression cassettes or systems that find use in, among other applications, the synthesis of the peptide display scaffolds. For expression, the gene product encoded by a polynucleotide of the invention is expressed in any convenient expression system, including, for example, bacterial, yeast, insect, amphibian and mammalian systems. Suitable vectors and host cells are described in U.S. Pat. No. 5,654,173. In the expression vector, a polynucleotide is linked to a regulatory sequence as appropriate to obtain the desired expression properties. These regulatory sequences can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the species from which the nucleic acid is obtained, or may be derived from exogenous sources.

Eukaryotic promoters suitable for use include, but are not limited to, the following: the promoter of the mouse metallothionein I gene sequence (Hamer et al., J. Mol. Appl. Gen. 1:273-288, 1982); the TK promoter of Herpes virus (McKnight, Cell 31:355-365, 1982); the SV40 early promoter (Benoist et al., Nature (London) 290:304-310, 1981); the yeast gal1 gene sequence promoter (Johnston et al., Proc. Natl. Acad. Sci. (USA) 79:6971-6975, 1982); Silver et al., Proc. Natl. Acad. Sci. (USA) 81:5951-59SS, 1984), the CMV promoter, the EF-1 promoter, Ecdysone-responsive promoter(s), tetracycline-responsive promoter, and the like.

Promoters may be, furthermore, either constitutive or regulatable. Inducible elements are DNA sequence elements that act in conjunction with promoters and may bind either repressors (e.g. lacO/LAC Iq repressor system in *E. coli*) or inducers (e.g. gal1/GAL4 inducer system in yeast). In such cases, transcription is virtually "shut off" until the promoter is derepressed or induced, at which point transcription is "turned-on."

Expression vectors generally have convenient restriction sites located near the promoter sequence to provide for the insertion of nucleic acid sequences encoding heterologous proteins. A selectable marker operative in the expression host may be present. Expression vectors may be used for, among other things, the screening methods described in greater detail below.

Expression cassettes may be prepared comprising a transcription initiation region, the gene or fragment thereof, and a transcriptional termination region. After introduction of the DNA, the cells containing the construct may be selected by means of a selectable marker, the cells expanded and then used for expression.

The above described expression systems may be employed with prokaryotes or eukaryotes in accordance with conventional ways, depending upon the purpose for expression. In some embodiments, a unicellular organism, such as *E. coli, B. subtilis, S. cerevisiae*, insect cells in combination with baculovirus vectors, or cells of a higher organism such as vertebrates, e.g. COS 7 cells, HEK 293, CHO, *Xenopus Oocytes*, etc., may be used as the expression host cells. In other situations, it is desirable to use eukaryotic cells, where the expressed protein will benefit from native folding and post-translational modifications.

Specific expression systems of interest include bacterial, yeast, insect cell and mammalian cell derived expression systems. Expression systems in bacteria include those described in Chang et al., *Nature* (1978) 275:615; Goeddel et al., *Nature* (1979) 281:544; Goeddel et al., *Nucleic Acids Res.* (1980) 8:4057; EP 0 036,776; U.S. Pat. No. 4,551,433; DeBoer et al., *Proc. Natl. Acad. Sci. (USA)* (1983) 80:21-25; and Siebenlist et al., *Cell* (1980) 20:269.

Mammalian expression is accomplished as described in Dijkema et al., *EMBO J.* (1985) 4:761, Gorman et al., *Proc. Natl. Acad. Sci. (USA)* (1982) 79:6777, Boshart et al., *Cell* (1985) 41:521 and U.S. Pat. No. 4,399,216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657, 866, 4,927,762, 4,560,655, WO 90/103430, WO 87/00195, and U.S. RE 30,985.

Host Cells Presenting Peptide Display Scaffolds

As will be appreciated by those in the art, the type of host cells suitable for use can vary widely. In some embodiments, the cell is a bacterial cell, a yeast cell or a mammalian cell. In some preferred embodiments, the biological entity is a bacterial cell. In some preferred embodiments, the bacterial cell is *Escherichia coli, Shigella sonnei, Shigella dysenteriae, Shingella flexneri, Salmonella typhimurium, Salmonella enterica, Enterobacter aerogenes, Serratia marcescens, Yersinia pestis*, or *Klebsiella pneumoniae*.

Generally, any mammalian cells may be used, with mouse, rat, primate and human cells being of particular interest. Accordingly, suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, etc.

The constructs can be introduced into the host cell by any one of the standard means practiced by one with skill in the art to produce a cell line of the invention. The nucleic acid constructs can be delivered, for example, with cationic lipids (Goddard, et al, Gene Therapy, 4:1231-1236, 1997; Gorman, et al, Gene Therapy 4:983-992, 1997; Chadwick, et al, Gene Therapy 4:937-942, 1997; Gokhale, et al, Gene Therapy 4:1289-1299, 1997; Gao, and Huang, Gene Therapy 2:710-722, 1995, all of which are incorporated by reference herein), using viral vectors (Monahan, et al, Gene Therapy 4:40-49, 1997; Onodera, et al, Blood 91:30-36, 1998, all of which are incorporated by reference herein), by uptake of "naked DNA", and the like.

Cellular Libraries of Peptide Sequences (CLiPS)

Also disclosed herein are cellular libraries of candidate peptide sequences including a plurality of cells each expressing a peptide display scaffold and presenting at least one candidate peptide. By a "plurality of cells" or a "population of host cells" herein is meant roughly from about $10^3$ cells to $10^8$ or $10^9$, with from $10^6$ to $10^8$ being of particular interest. This plurality of cells comprises a cellular library, wherein generally each cell within the library includes at least one peptide display scaffold at the outer membrane. In certain embodiments, the library is enriched for cells expressing peptide display scaffolds presenting candidate peptides. By "enriched" is meant that the cells of the library exhibit at least one detectable signal from the peptide display scaffolds. The enrichment of the cells cane done by, for example, fluorescence activated cell sorting.

In some embodiments, each cell of the cellular library expresses a single type of peptide display scaffold. For example, each cell expresses at least one peptide display scaffold on the extracellular surface of the cell outer membrane, wherein all the peptide display scaffolds of the cell present the same candidate peptide.

In other embodiments, the cellular library includes cells expressing two or more different types of peptide display scaffolds, including three or more and four or more, etc. By "different types of peptide display scaffolds" is meant that each type of peptide display scaffold displayed on the surface of the cell presents a candidate peptide that is different than the candidate peptide presented by the other type of peptide display scaffold displayed on the surface of the cell. For example, in embodiments in which a cellular library includes a cell expressing a first and second peptide display scaffold, the candidate peptide presented by the first peptide display scaffold is different from the candidate peptide presented by the second peptide display scaffold. It will be appreciated by one of skill in the art that in such embodiments, the $D_1$ and $D_2$ of the first peptide display scaffold will be different than the $D_1$ and $D_2$ of the second peptide display scaffold.

In one embodiment, the CLiPS is a library of fully randomized candidate peptides, with no sequence preferences or constants at any position. In another embodiment, the CLiPS is a library of biased candidate peptides. That is, some positions within the sequence are either held constant, or are selected from a limited number of possibilities. For example, in one embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In another embodiment, the bias is towards peptides that interact with known classes of enzymes, e.g., proteases. A number of molecules or protein domains are suitable as starting points for the generation of biased randomized candidate regulator polypeptides. A large number of small molecule domains are known that confer a common function, structure or affinity. In addition, as is appreciated in the art, areas of weak amino acid homology may have strong structural homology. A number of these molecules, domains, and/or corresponding consensus sequences, are known, including, but are not limited to, SH-2 domains, SH-3 domains, Pleckstrin, death domains, protease cleavage/recognition sites, enzyme inhibitors, enzyme substrates, Traf, etc. In addition, agonists and antagonists of any number of molecules may be used as the basis of biased randomization of candidate regulator polypeptides as well.

Methods

As mentioned above, the peptide display scaffolds described herein find particular utility in assays designed to screen candidate peptides and identify a peptide that interacts with an enzyme. As used herein, "interact" or "interaction" with respect to a candidate peptide and an enzyme is meant the recognition and involvement between the enzyme and peptide to produce an effect either on the peptide or the enzyme. For example, "interaction" includes cleavage of a candidate substrate by the enzyme, inhibition of an enzyme by a candidate inhibitor, modulation of enzyme specificity and/or activity by a candidate allosteric regulator, modulation of enzyme specificity and/or activity with respect to a candidate peptide (e.g., candidate substrate or candidate inhibitor) by a known allosteric regulator, and the like. As such, exemplary candidate peptides include candidate enzyme substrates, candidate enzyme inhibitors, candidate allosteric regulators of enzymes, and the like.

The screening methods may be part of a multi-step screening process of evaluating candidate peptides for their efficacy (and safety) in interacting, e.g., as a substrate, inhibitor, or allosteric regulator, with an enzyme. In multi-step screening processes, a candidate peptide or library of candidate peptides is subjected to screening in a second in vivo model, e.g. a mouse model, following screening in the in vitro cell system. Following the initial screening in the cell lines, the positive compounds are then screened in non-human mammalian animal models.

Enrichment

In some embodiments of the methods disclosed herein, the cells are enriched prior to screening the library of cells presenting candidate peptides in peptide display scaffolds to identify a peptide that interacts with an enzyme, the library of cells is optionally enriched for cells expressing peptide display scaffolds. The optional enrichment allows for removal of cells from the cell library that (1) do not express peptide display scaffolds on the cell outer membrane or (2) express non-functional peptide display scaffolds on the cell outer membrane. By "non-functional" is meant that the peptide display scaffold does not properly display a candidate peptide, e.g., as a result of a stop codon or a deletion mutation, or does not properly display one or both detectable moieties.

Enrichment for cells can be accomplished by growing the cell population and inducing expression of the peptide display scaffolds. The cells are then sorted to collect all cells that have a $D_1$ signal and cells that do not have a $D_1$ signal are discarded. Cells that properly display a candidate peptide in a peptide display scaffolds are not truncated and will have a $D_1$ detectable moiety linked to the candidate peptide (C). For example, if expression of a peptide display scaffold from an expression vector that includes within the sequence for the candidate peptide a stop codon, the resulting expressed peptide display scaffold would by truncated due to the stop codon and would not have a $D_1$ detectable moiety and no $D_1$ signal. As a result of the enrichment, the cell that expresses the truncated peptide display scaffold would not be identified by the $D_1$ signal and would be discarded because it does not properly display a candidate peptide. A screen for only those cells that have a D1 signal ensures that only those cells that properly display the candidate peptide are included in the screening assay.

An exemplary enrichment protocol is schematically described in FIG. 1, panel A. The exemplary enrichment step uses a strepavadin binding peptide as the $D_1$ detectable moiety. Following expression of the peptide display scaffolds, the cells are contacted with strepavadin conjugated phycoerythrin. As a result, all cells that properly express the peptide display scaffold will be labeled with the strepavadin conjugated phycoerythrin, which binds to the strepavadin binding peptide. The cells are then subjected to fluorescence activated cell sorting to collect the cells exhibiting the $D_1$ signal (e.g., phycoerythrin). Following the optional enrichment step, the cellular library can then be screened to identify a peptide that interacts with an enzyme.

In one embodiments, a library of cells presenting candidate peptides in peptide display scaffolds is screened to identify a peptide that interacts with an enzyme (e.g., a ligand of an enzyme), by contacting a cell library enriched for expression of peptide display scaffolds with an enzyme, wherein each peptide display scaffold is described by Formula (I):

[D-C]-TM  (I)

wherein TM is a transmembrane protein, C is a candidate peptide; and D is a detectable moiety, wherein the cells of the cell library exhibit a D signal prior to contacting with the enzyme; and detecting the presence or absence of a D signal, by for example fluorescence activated cell sorting, wherein a decrease in the D signal in the presence of the enzyme as compared to the absence of the enzyme indicates that at least one cell of the cell library expresses a candidate peptide that is a substrate for the enzyme.

In such embodiments, prior to addition of the enzyme (e.g., a peptidase) the enriched library exhibits a D signal. Following the addition of the enzyme, if at least one-cell presents a candidate peptide that is a substrate for the enzyme, the candidate peptide will be cleaved, thereby releasing the domain having the D detectable moiety. Therefore, the cell will not exhibit a D signal and instead will no detectable signal. As such, following the addition of the enzyme, cells exhibiting no detectable signal can be collected and the sequence of the candidate peptide determined to identify substrates for the enzyme. In such embodiments, a decrease in the D signal in the presence of the enzyme relative to the D signal in the absence of the enzyme indicates that at least one cell of the cell library expresses a candidate peptide that is a substrate for the enzyme.

In certain embodiments C is [A-$C_S$] or [$C_S$-A] wherein A is an allosteric regulator for the enzyme and $C_s$ is a candidate substrate for the enzyme and a decrease in the D signal indicates that at least one cell of the cell library expresses a candidate peptide that is a substrate for the enzyme.

This embodiment is particularly useful for identifying a secondary substrate for an enzyme that is cleaved in the presence of an allosteric regulator. In such embodiments, prior to addition of the enzyme (e.g., a peptidase) the cell exhibits a D signal. Following the addition of the enzyme, if the candidate peptide is a substrate for the enzyme that cleaved is in the presence of an allosteric regulator, the candidate peptide will be cleaved, thereby releasing the domain having the D detectable moiety. Therefore, the cell will not exhibit a D signal and instead will exhibit no detectable signal. As such, following the addition of the enzyme, cells exhibiting no detectable signal can be collected and the sequence of the candidate peptide determined to identify substrates for the enzyme that are cleaved in the presence of an allosteric regulator. In such embodiments, a decrease in the D signal in the presence of the enzyme relative to the D signal in the absence of the enzyme indicates that at least one cell of the cell library expresses a candidate peptide that is a substrate for the enzyme that is cleaved in the presence of an allosteric regulator.

In another embodiment, a library of cells presenting candidate peptides in peptide display scaffolds is screened to identify a peptide that interacts with an enzyme (e.g., a ligand of an enzyme), by contacting a cell library enriched for expression of peptide display scaffolds with an enzyme, wherein each peptide display scaffold is described by Formula (II) or Formula (III):

[D-S-$C_i$]-TM (II)

[D-$C_i$-S]-TM (III)

wherein TM is a transmembrane protein, S is a known substrate for the enzyme, $C_i$ is a candidate inhibitor peptide, D is a detectable moiety, wherein the cells of the cell-library exhibit a D signal prior to contacting with the enzyme, and detecting the presence or absence of a D signal, by for example fluorescence activated cell sorting, wherein maintenance of the D signal in the presence of the enzyme as compared to the absence of the enzyme indicates that $C_i$ is an inhibitor for the enzyme.

In such embodiments, prior to addition of the enzyme (e.g., a peptidase) the cell exhibits a D signal. Following the addition of the enzyme, the known substrate will be cleaved by the enzyme thereby releasing the domain having the D detectable moiety. Therefore, the cell will not exhibit a D signal. However, if the candidate peptide is an inhibitor of the enzyme, it will inhibit the activity of the enzyme upon the known substrate, thereby preventing cleavage and release of the D detectable moiety. As such, following the addition of the enzyme, cells that maintain the D signal can be collected and the sequence of the candidate peptide determined to identify an inhibitor for the enzyme. In such embodiments, maintenance of the D signal indicates that $C_i$ is an inhibitor for the enzyme.

Dual-Signal Screening

In other embodiment, a library of cells presenting candidate peptides in peptide display scaffolds is screened to identify a peptide that interacts with an enzyme (e.g., a ligand of an enzyme), by contacting a cell library that is optionally enriched for expression of peptide display scaffolds as described above with an enzyme, wherein each peptide display scaffold is described by Formula (VI):

[$D_1$-C]-TM-[$D_2$] (VI)

wherein TM is a transmembrane protein, C is a candidate peptide, and $D_1$ and $D_2$ are first and second detectable moieties, wherein $D_1$ and $D_2$ are different (e.g., the $D_1$ detectable signal is different from the $D_2$ detectable signal, such as a different color) and wherein prior to contacting the cell with the enzyme, the cell exhibits a $D_1$ signal and does not exhibit a detectable $D_2$ signal above a background level (e.g., when $D_1$ provides a detectable signal by binding of an affinity ligand labeled fluorescent moiety $D_2$ does not provide a detectable signal), and wherein the cells of the cell library exhibit a $D_1$ signal prior to contacting with the enzyme and detecting the presence or absence of a $D_1$ signal and the presence or absence of a $D_2$ signal, by for example, fluorescence activated cell sorting. In such embodiments, an increase in the $D_2$ signal indicates that at least one cell of the cell library expresses a candidate peptide that interacts with the enzyme.

In certain embodiments, C is a candidate substrate for the enzyme. In such embodiments, prior to addition of the enzyme (e.g., a peptidase) the cell exhibits a $D_1$ signal. Following the addition of the enzyme, if the candidate peptide is a substrate for the enzyme, the candidate peptide will be cleaved, thereby releasing the domain having the $D_1$ detectable moiety. Therefore, the cell will not exhibit a $D_1$ signal and instead will exhibit a $D_2$ signal because the absence of the $D_1$ detectable moiety allows binding of an affinity ligand labeled fluorescent moiety to bind $D_2$ and provide a detectable signal. As such, following the addition of the enzyme, cells exhibiting the $D_2$ signal can be collected and the sequence of the candidate peptide determined to identify substrates for the enzyme. In such embodiments, an increase in the $D_2$ signal relative to the $D_1$ signal indicates that at least one cell of the cell library expresses a candidate peptide that is a substrate for the enzyme. Likewise, an increase in the $D_2$ signal relative to the $D_1$ signal in the absence of the enzyme indicates that at least one cell of the cell library expresses a candidate peptide that interacts with the enzyme.

In other embodiments, C is [S-$C_i$] or [$C_i$-S] where S is known substrate for the enzyme and $C_i$ is a candidate inhibitor. In such embodiments, prior to addition of the enzyme (e.g., a peptidase) the cell exhibits a $D_1$ signal. Following the addition of the enzyme, the known substrate will be cleaved by the enzyme thereby releasing the domain having the $D_1$ detectable moiety. Therefore, the cell will not exhibit a $D_1$ signal and instead will exhibit a $D_2$ signal because the absence of the $D_1$ detectable moiety allows binding of an affinity ligand labeled fluorescent moiety to bind $D_2$ and provide a detectable signal. However, if the candidate peptide is an inhibitor of the enzyme, it will inhibit the activity of the enzyme upon the known substrate, thereby preventing cleavage and release of the $D_1$ detectable moiety. As such, following the addition of the enzyme, cells that maintain the $D_1$ signal can be collected and the sequence of the candidate peptide determined to identify an inhibitor for the enzyme. In such embodiments, maintenance of the $D_1$ signal relative to the $D_2$ signal indicates that $C_i$ is an inhibitor for the enzyme.

In other embodiments, C is [A-$C_S$] or [$C_S$-A] where A is a known allosteric regulator of the enzyme and $C_i$ is a candidate substrate for the enzyme. This embodiment is particularly useful for identifying a secondary substrate for an enzyme that is cleaved in the presence of an allosteric regulator. In such embodiments, prior to addition of the enzyme (e.g., a peptidase) the cell exhibits a $D_1$ signal. Following the addition of the enzyme, if the candidate peptide is a substrate for the enzyme that cleaved is in the presence of an allosteric regulator, the candidate peptide will be cleaved, thereby releasing the domain having the $D_1$ detectable moiety. Therefore, the cell will not exhibit a $D_1$ signal and instead will exhibit a $D_2$ signal because the absence of the $D_1$ detectable moiety allows binding of an affinity ligand labeled fluorescent moiety to bind $D_2$ and provide a detectable signal. As such, following the addition of the enzyme, cells exhibiting the $D_2$ signal can be collected and the sequence of the candidate peptide determined to identify substrates for the enzyme that are cleaved in the presence of an allosteric regulator. In such embodiments, an increase in the $D_2$ signal relative to the $D_1$ signal indicates that at least one cell of the cell library expresses a candidate peptide that is a substrate for the enzyme that is cleaved in the presence of an allosteric regulator.

In another embodiment, a library of cells presenting candidate peptides in peptide display scaffolds is screened to identify a peptide ligand for an enzyme (e.g., a ligand for an enzyme), by contacting a cell library optionally enriched for expression of peptide display scaffolds with an enzyme, wherein each peptide display scaffold is described by Formula (XI):

[$D_1$-$C_i$]-TM-[$C_2$-$D_2$]     (XI)

wherein TM is a transmembrane protein, $C_1$ and $C_2$ are first and second candidate peptides, $D_1$ and $D_2$ are first and second detectable moieties, wherein $D_1$ and $D_2$ are different and wherein prior to contacting the cell with the enzyme, the cell exhibits a $D_1$ signal and does not exhibit a detectable $D_2$ signal above a background level (e.g., when $D_1$ provides a detectable signal by binding of an affinity ligand labeled fluorescent moiety $D_2$ does not provide a detectable signal), detecting the presence or absence of a $D_1$ signal and the presence or absence of a $D_2$ signal, by for example, fluorescence activated cell sorting, wherein the detecting indicates whether $C_2$ is a peptide ligand for the enzyme.

In certain embodiments, $C_1$ is a substrate for the enzyme and $C_2$ is a candidate inhibitor for the enzyme. In such embodiments, prior to addition of the enzyme (e.g., a peptidase) the cell exhibits a $D_1$ signal. Following the addition of the enzyme, the known substrate will be cleaved by the enzyme thereby releasing the domain having the $D_1$ detectable moiety. Therefore, the cell will not exhibit a $D_1$ signal and instead will exhibit a $D_2$ signal because the absence of the $D_1$ detectable moiety allows binding of an affinity ligand labeled fluorescent moiety to bind $D_2$ and provide a detectable signal. However, if the candidate peptide is an inhibitor of the enzyme, it will inhibit the activity of the enzyme upon the known substrate, thereby preventing cleavage and release of the $D_1$ detectable moiety. As such, following the addition of the enzyme, cells that maintain the $D_1$ signal can be collected and the sequence of the candidate peptide determined to identify an inhibitor for the enzyme. In such embodiments, maintenance of the $D_1$ signal relative to the $D_2$ signal indicates that $C_2$ is an inhibitor for the enzyme.

In other embodiments, $C_1$ is a known allosteric regulator of the enzyme and $C_2$ is a candidate substrate for the enzyme. This embodiment is particularly useful for identifying a secondary substrate for an enzyme that is cleaved in the presence of an allosteric regulator. In such embodiments, prior to addition of the enzyme (e.g., a peptidase) the cell exhibits a $D_2$ signal. Following the addition of the enzyme, if the candidate peptide is a substrate for the enzyme that is cleaved in the presence of an allosteric regulator, the candidate peptide will be cleaved, thereby releasing the domain having the $D_2$ detectable moiety. Therefore, the cell will not exhibit a $D_2$ signal and instead will exhibit a $D_1$ signal because the absence of the $D_2$ detectable moiety allows binding of an affinity ligand labeled fluorescent moiety to bind $D_1$ and provide a detectable signal. As such, following the addition of the enzyme, cells exhibiting the $D_1$ signal can be collected and the sequence of the candidate peptide determined to identify substrates for the enzyme that are cleaved in the presence of an allosteric regulator. In such embodiments, an increase in the $D_1$ signal relative to the $D_2$ signal indicates that at least one cell of the cell library expresses a candidate peptide that is a substrate for the enzyme that is cleaved in the presence of an allosteric regulator.

Generally a plurality of assay mixtures is performed in parallel with different enzyme concentrations to obtain a differential response to the various concentrations of enzyme and candidate peptide. Typically, one of these concentrations serves as a negative control, i.e. no compound. In a preferred embodiment, a high throughput screening protocol is employed, in which a large number of candidate agents are tested in parallel using a large number of cell populations. By "large number" is meant a plurality, where plurality means at least 10 to 50, usually at least 100, and more usually at least 1000, where the number of may be 10,000 or 50,000 or more, but in many instances will not exceed 5000.

Methods of measuring and/or monitoring fluorescence are well known in the art. Both qualitative assessments (positive/negative) and quantitative assessments (comparative degree of fluorescence) may be provided by the present methods. Brightness can be measured using any known method, including, but not limited to, visual screening, spectrophotometry, spectrofluorometry, fluorescent microscopy, by fluorescence activated cell sorting (FACS) machines, etc. In some embodiments, monitoring of fluorescent biosensor polypeptides includes the use of an automated imaging system such as an Axon ImageXpress 5000 equipped with a live cell imaging chamber. Other suitable imaging systems include, but are not limited to, BD Biosciences (Pathway HT); Cellomics (ArrayScan V); Amersham (IN Cell Analyzer 1000, IN Cell Analyzer 3000); Molecular Devices (Discovery-1, Discovery-TMA, ImageXpress), and the like.

Automated Screening Methods

The screening methods may be automated to provide convenient, real time, high volume methods of screening a cellular library of peptide sequences for activity in interacting with an enzyme. Automated methods are designed to detect changes in the fluorescence of one or more of the detectable moieties of the peptide display scaffolds in the presence of the enzyme as compared to the absence of the enzyme, or by comparison to a control apparatus, which is not exposed to the test sample, or by comparison to pre-established indicia. Both qualitative assessments (positive/negative) and quantitative assessments (e.g., quantity of cells emitting a $D_1$ detectable signal and the quantity of cells emitting a $D_2$ detectable signal) may be provided by the present automated methods.

Measurement points may be over time following addition of enzyme, or among test and control samples. A computer program product controls operation of the measuring means and performs numerical operations relating to the above-described steps. The preferred computer program product comprises a computer readable storage medium having computer-readable program code means embodied in the medium. Hardware suitable for use in such automated apparatus will be apparent to those of skill in the art, and may include computer controllers, automated sample handlers, fluorescence measurement tools, printers and optical displays. The measurement tool may contain one or more photodetectors for measuring the fluorescence signals from samples where fluorescently detectable molecules are utilized. The measurement tool may also contain a computer-controlled stepper motor so that each control and/or test sample can be arranged as an array of samples and automatically and repeatedly positioned opposite a photodetector during the step of measuring fluorescence intensity.

The measurement tool (e.g., a fluorescence activated cell sorter) is preferably operatively coupled to a general purpose or application specific computer controller. The controller preferably comprises a computer program produce for controlling operation of the measurement tool and performing numerical operations relating to the above-described steps. The controller may accept set-up and other related data via a file, disk input or data bus. A display and printer may also be provided to visually display the operations performed by the controller. It will be understood by those having skill in the art that the functions performed by the controller may be realized in whole or in part as software modules running on a general purpose computer system. Alternatively, a dedicated stand-alone system with application specific integrated circuits for performing the above described functions and operations may be provided.

Kits and Systems

Also described herein are kits and systems for use in practicing the screening methods, where the kits typically include elements for making the CLiPS e.g., a construct comprising a vector that includes a coding region for the display scaffold, where the nucleic acid sequence encoding the display scaffold has a restriction endonuclease site for custom insertion of candidate peptide sequences. In some embodiments, the kits and systems can include, in separate compartments or containers, one or more of the following: 1) one or more constructs encoding a display scaffold; 2) a candidate agent; and 3) a cell containing an expression construct for producing the display scaffold. The components of the kits may be modified commensurate to the disclosure provided above.

The kit components are typically present in a suitable storage medium, e.g., buffered solution, typically in a suitable container. In some embodiments, the kit comprises a plurality of different vectors each encoding the peptide display scaffold, where the nucleic acid sequence encoding the display scaffold has a restriction endonuclease site for custom insertion of candidate sequences and where the vectors are designed for expression in different environments and/or under different conditions, e.g., constitutive expression where the vector includes a strong promoter for expression in cells or conditional expression using an inducible promoter. Alternatively, the vector can be provided as a promoterless vector with a multiple cloning site for custom insertion of a promoter and tailored expression of a display scaffold, etc.

In addition to the above components, the kits will further include instructions for practicing the methods described herein. These instructions may be present in the kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the interne to access the information at a removed site. Any convenient means may be present in the kits.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure, is at or near atmospheric.

Methods and Materials

The following methods and materials are used in the examples below.

Reagents and Strains

Streptavidin-conjugated phycoerythrin (SA-PE) (Invitrogen), the catalytic subunit light chain of enteropeptidase (EP) (New England Biolabs), oligonucleotides (Operon), Ni-NTA resin (Qiagen), and synthetic peptides (New England Peptide) were used without modifications. Plasmid pET-23b containing procaspase-3 was obtained from ATCC (ATCC#99625). E. coli strain MC1061 was used for all experiments (Casadaban et al., JMB 138(2):179-207 (1980). All bacterial growth was performed at 37° C. with vigorous shaking in Luria-Bertani broth (LB) supplemented with 34 g/mL chloramphenicol (cm), unless another antibiotic is specified.

CLIPS Construction

Plasmid Vector and Library Construction

Construction of a control plasmid (pBSX) expressing a GGSG linker and the previously identified streptavidin binding peptide CX72-S8 was performed as described previously (Rice et. al., Protein Sci. 15(4):825-36 (2006)). Plasmids encoding surface displayed peptide substrates for enteropeptidase (DDDDK) (SEQ ID NO:02) or caspase-3 (DEVD) (SEQ ID NO:16) were constructed as follows. Primers 1 and 2 were used with primer 3 and primer 4 Table 1) to amplify the DNA fragments encoding an in frame fusion of the streptavidin-binding peptide (WCCHPMWEVMCLR) (SEQ ID NO:17), the substrate sequence flanked by flexible linkers, and a circularly permuted outer membrane protein X (CPX) as disclosed in U.S. patent application Ser. No. 10/920,244, now U.S. Pat. No. 7,256,038, which is herein incorporated by reference. Products were digested with SfiI and ligated to similarly digested pBAD33. A substrate library, of the form $X_6$, where X is any amino acid, was constructed using PCR with a synthetic oligonucleotide incorporating NNS codons along with primers 1, 5 and 6 (Table 1). The product was digested with SfiI and ligated into a similarly digested pBAD33 plasmid. Transformation of the plasmid library into electrocompetant MC1061 yielded $1.5 \times 10^8$ colony forming units.

Fluorescent proteins exhibiting Föster resonance energy transfer (FRET) (Nguyen et al., Nat. Biotech. 23(3):355-360

(2005)) (CyPet and YPet) were used to construct fluorogenic protease substrates. Substrates EP2.1, EP4.1, EP4.2, and EP4.3 identified for enteropeptidase by CLiPS were amplified with YPet using reverse primer 7 with forward primers 8, 9, 10, and 11, respectively (Table1). The canonical EP substrate was amplified as a fusion to YPet using primers 7 and 12 (Table 1). As a negative control, a GSGSGS (SEQ ID NO:18) linker was substituted for the six amino acid substrate sequence using primers 7 and 13 (Table 1). These products were digested with kpnI and sphI and ligated to similarly digested plasmid containing CyPET to yielded plasmids pBC21Y, pBC41Y, pBC42Y, pBC43Y pBCEPY and pBCGSY.

TABLE 1

| Primer Sequence (5' to 3') |
| --- |
| 1 GGCTGAAAATCTTCTCTC<br>(SEQ ID NO: 169) |
| 2 CTGGCCAGTCTGGCCAGTGGGTGTGCCACCCGATGTGGGAGGTGATG<br>TGCCTGAGGGGAG<br>(SEQ ID NO: 170) |
| 3 TGCCCAGACTGCCCTCCTTTATCATCGTCATCTTGTCCAGACCCTCC<br>CCTCAGGCACATC<br>(SEQ ID NO: 21) |
| 4 TGATGTGCCTGAGGGGAGGGTCTGGTCAAGATGAAGTTGATGGAGGG<br>CAGTCTGGGCAG<br>(SEQ ID NO: 22) |
| 5 TGACTGAGGCCAGTCTGGCCAGTGGGTGTGCCACCCGATGTGGGAGG<br>TGATGTGCCTGAG<br>(SEQ ID NO: 23) |
| 6 AGGTGATGTGCCTGAGGGGAGGGTCTNNSNNSNNSNNSNNSNNSGGA<br>GGGCAGTCTGGGC<br>(SEQ ID NO: 24) |
| 7 CAAAACAGCCAAGCTTGCATGCGGCCACCTTGGCCTTATTAGTGGTG<br>GTGGTGGTGGTGTTTGTACAATTCATTCAT<br>(SEQ ID NO: 25) |
| 8 GGTAGCGGTAGCGGTACCATGTCGGGGGAGCGGTGGGGCAGCGGTAG<br>CGGTGGCAGCATG<br>(SEQ ID NO: 26) |
| 9 GGTAGCGGTAGCGGTACCGTGGACTACCGCTTCCTCGGCAGCGGTAG<br>CGGTGGCAGCATG<br>(SEQ ID NO: 27) |
| 10 GGTAGCGGTAGCGGTACCATGCACGGGGAGAGGATGGGCAGCGGTAG<br>CGGTGGCAGCATG<br>(SEQ ID NO: 28) |
| 11 GGTAGCGGTAGCGGTACCTCCGGGGACAGGATGTGGGGCAGCGGTAG<br>CGGTGGCAGCATG<br>(SEQ ID NO: 29) |
| 12 GGTAGCGGTAGCGGTACCGGTGATGATGATGATAAAGGCAGCGGTAG<br>CGGTGGCAGCATG<br>(SEQ ID NO: 30) |
| 13 GGTAGCGGTAGCGGTACCGGTGGCAGCGGCGGTAGCGGTGGTGGTAG<br>CGGTGGCAGCATG<br>(SEQ ID NO: 31) |

Substrate Library Screening

For screening and clone analysis, overnight cultures were subcultured by dilution into fresh medium (1:50) and grown for 2 hours. The subculture was then induced with 0.04% arabinose and incubated with shaking at room temperature. Cell aliquots were harvested washed with PBS (pH 8.0) and absorbance at 600 nm (OD600) was measured to estimated density. Cells were pelleted by centrifugation, the supernatant removed and the cells resuspended in reaction buffer (10 L). The enzyme was added, and the reaction mixture was incubated at room temperature on rotary shaker (60 rpm). To stop the reaction cells were removed and diluted 100-fold in PBS, pelleted by centrifugation, and resuspended in PBS containing SA-PE (50 nM). After incubation at room temperature (1 hr), cells were washed with PBS and analyzed or sorted using a FACSAria™ cell sorter.

For enteropeptidase cleavage assays, cultures were induced for 2 hr. The reaction buffer for enteropeptidase was 50 mM Tris-Cl pH 8.0 supplemented with 20 mM NaCl and 2 mM $CaCl_2$. Three complete cycles of sorting for cleaved substrates were performed by alternating between sorting cells that display substrates (1A, 2A, and 3A) in the absence of any added enzyme, and for cells with hydrolyzed substrates (1B, 2B, 3B) after enzyme treatment. To remove clones from the library pool that did not properly display the substrate and binding peptide (e.g., stop codons or frame shift mutations), cells were sorted after 1 hr incubation in the reaction buffer without enzyme. Sorts for enteropeptidase hydrolysis (1B, 2B, 3B and 4), were performed after reactions with 2.9 nM of light-chain enteropeptidase for 22, 18, 4, and 1 hr, respectively. Control populations, MC1061/pBSEPX and MC1061/pBSX were used to set the sorting gates during each of the first three rounds, and the fourth round sort gate was set to isolate substrates that hydrolyzed faster than the canonical substrate (MC1061/pBSEPX). The enriched library pool was plated and individual clones were assayed for substrate conversion, using 1 hr reaction with, and without, 2.9 nM EP.

For caspase-3 assays, cultures were induced for 3 hr, reactions were carried out in PBS pH 8.0, and all sorting was performed after 5 hr reactions. The human pro-caspase-3 gene was amplified by PCR from pET23bcasp and digested and ligated into similarly digested pBAD30 yielding pB30CS using methods known in the art. Overnight cultures of MC1061/pBAD30 and MC1061/pB30CS were sub-cultured 1:100, grown in LB with 50 g/ml carbenicillin for 2 hr and induced for 5 hr at 37° C. From these cultures, soluble protein was isolated using B-PER-II™ Bacterial Protein Extraction Reagent (Pierce). Protein extracts were dialyzed in PBS to remove detergent. In an effort to enhance substrate specificity for caspase-3 over potential endogeneous proteases, 1 μL soluble protein from MC1061/pBAD30 culture was added to the induced library in sorting cycles 1A and 2A. An induction time of 3 hr was found to increase resolution between fluorescent and non-fluorescent cells, and was used for experiments with caspase-3. Reaction buffers used were based on known compatible reaction buffers, and reaction times were based on cleavage observed for positive control bacteria displaying known substrates. Background hydrolysis of the regions flanking the substrate site (i.e. a clone displaying the GGQSGQ (SEQ ID NO:44) linker and streptavidin-binding peptide), was measured under each reaction condition to ensure that hydrolysis occurred in the designated substrate region. Sorting for caspase-3 hydrolysis (1B and 2B) was performed after adding 1 μL, soluble protein prepared from MC1061/pB30CS. The enriched library pool was plated, and individual clones were assayed for specific conversion using 5 hr reactions with soluble protein preparations with and without caspase-3.

Recombinant and Synthetic Protein Substrate Reaction Conditions

Overnight cultures of MC 1061 transformed with the FRET substrate encoding expression vectors described above were subcultured 1:50 and grown for 2 hrs. The cultures were induced by addition of arabinose to 0.04% w/v and incubated at room temperature for 16 hrs with shaking. Soluble protein was prepared using BPER-II™ as above, and fusion proteins with C-terminal 6x-His tags were purified using Ni-NTA resin (Qiagen). Reactions were performed in 100 μL of enteropeptidase reaction buffer with ~0.5 μM fusion protein, as determined using the extinction coefficient of YPet at 514 nm (Nguyen et al., Nat Biotechnol 23:355-60 (2005)) and Beer's law. Enteropeptidase was added to each reaction to a final concentration of 0.29 nM and fluorescence emission at 475 nm (cyan) and 527 nm (yellow) was monitored upon excitation at 433 nm using a Safire fluorimeter (Tecan).

Synthetic substrates, utilizing Edans and Dabcyl as donor and quencher, were obtained from New England Peptide for the canonical substrate, Dabcyl-DDDDKGG-(E-Edans)-amide (SEQ ID NO:32), and EP4.3, Dabcyl-SGDRMW(E-Edans)-amide (SEQ ID NO:33). Reactions were performed in enteropeptidase reaction buffer with between 1 and 4 μM of each peptide as determined using the extinction coefficient of Dabcyl at 468 nm of 32,000 $M^{-1}cm^{-1}$. Enteropeptidase was added to each reaction to a final concentration of 0.29 nM, and fluorescence emission at 495 nm was monitored upon excitation at 340 nm using a Safire fluorimeter.

Plasmid Vector and Library Construction

Construction of a control plasmid (pBSGXP2) expressing a fusion of the streptavidin-binding peptide (WCHPMW-EVMCLR) (SEQ ID NO:34) (Rice et. al. 2006) and a GGSGGS (SEQ ID NO:01) sequence flanked by flexible linkers on the amino terminus of circularly permuted outer membrane X (CPX) and a binding peptide of SLP-76 (P2) on the carboxy-terminus was performed using primers 1, 2, and 3 with primers 4 and 5. Using pBSGXP2 as a template, a plasmid encoding surface displayed peptide substrate for tobacco etch virus protease (TEV, ENLYFQS (SEQ ID NO:06)) instead of the GGSGGS (SEQ ID NO:01) region above was constructed using primers 1, 6 and 7 with primer 8. Products were digested with SfiI and ligated to similarly digested pBAD33. A substrate library (pBS5XP2) of the form $X_5$, where X is any amino acid, was constructed using PCR with a synthetic oligonucleotide incorporating NNS codons (primer 9) along with primers 1 and 8 (Table 2). The product was digested with SfiI and ligated into a similarly digested pBAD33 plasmid. Transformation of the plasmid library into electrocompetent MC 1061 yielded $6\times10^7$ colony forming units.

A second substrate library (pBSToptP2) was created using primer 10 with primers 1 and 8. The product was digested with SfiI and ligated into a similarly digested pBAD33 plasmid. Transformation of the plasmid library into electrocompetent MC1061 yielded $5\times10^7$ colony forming units.

TABLE 2

| Primer Sequence (5' to 3') |
|---|
| 1 CTGGCCAGTCTGGCCAGTGGGTGTGCCACCCGATGTGGGAGGTGATGT<br>GCCTGAGGGGAG<br>(SEQ ID NO: 35) |
| 2 TGGGAGGTGATGTCCCTGAGGGGAGGGTCTGGTCAAAGTGCCTCCGGC<br>GGTGGCAGC<br>(SEQ ID NO: 36) |
| 3 GCCTCCGGCGGTGGCAGCGGCGGTAGCTCTCAATCTGCGGGAGGGCAG<br>TCTGGGCAG<br>(SEQ ID NO: 37) |
| 4 CTTCTGTCTATCGAAGGAGCTGGCTGACCGGACTGACCTCCGCTTGCA<br>GTACGGCTTTT<br>(SEQ ID NO: 38) |

TABLE 2-continued

| Primer Sequence (5' to 3') |
|---|
| 5 AGCTTGGCCACCTTGGCCTTATTACAGTGGGGGTTTCGTGCTTCTGTC<br>TATCGAAG<br>(SEQ ID NO: 39) |
| 6 TGGGAGGTGATGTGCCTGAGGGGAGGGTCTGGTCAAAGTGCCTCCGGC<br>GAAAACGTCTAC<br>(SEQ ID NO: 40) |
| 7 TCCGGCGAAAACGTCTACTTTCAGAGCTCTCAATCTGCGGGAGGGCAG<br>TCTGGGCAGTCT<br>(SEQ ID NO: 41) |
| 8 GGCTGAAAATCTTCTCTC<br>(SEQ ID NO: 42) |
| 9 GGTCAAAGTGCCTCCGGCCAATCCNNSNNSNNSNNSNNSTCTCAATCT<br>GCGGGAGGGCAG<br>(SEQ ID NO: 43) |

Carboxy Terminus (D2) Labeling Conditions

Streptavidin conjugated phycoerythrin (SAPE) was used for labeling streptavidin binding affinity ligand on the N- and C-termini of CPX (FIG. 15). Fluorescent proteins YPet, EGFP and AlajGFP (*Biotechnol. Prog.* 2004, 20, 963-967) fused to the SH3 domain of Mona were found to be the suitable probes for the C-terminus of CPX (D2). Of the three fluorescent proteins AlajGFP-Mona gave a higher fluorescence and was used for all labeling. The resulting CPX scaffold required a 3 hr induction time due to the additional peptide that was fused to the C-terminus. For optimum labeling of cells without protease reaction, the cells were incubated for 1 hr at 22° C. with SAPE (50 nM) and AlajGFPM (250 nM). Longer incubation time led to higher labeling with AlajGFPM, and 2 hrs could be used to further separate the cells displaying CPX from those that do not. For the described example below 1 hr incubation was used.

Recombinant and Synthetic Protein Substrate Reaction Conditions

For screening and clone analysis, overnight cultures were subcultured by dilution into fresh medium (1:50) and grown for 2 hrs at 37° C. The subculture was induced with 0.1% arabinose and incubated with shaking at room temperature for 3 hrs. Cell aliquots were washed with PBS (pH 8.0), and optical density at 600 nm ($OD_{600}$) was measured to estimate cell concentration. Cells ($10^8$) were pelleted by centrifugation, the supernatant was removed, and the cells were resuspended in reaction buffer (10 μL). Following addition of the enzyme, the reaction mixture was incubated at room temperature on a rotary shaker. Cells were removed and diluted 100-fold in PBS to stop the reaction, pelleted by centrifugation, and resuspended in PBS containing SA-PE (50 nM) and AlajGFP-MONA. After incubation at room temperature (1 hr), cells were washed with PBS and analyzed or sorted using a FACSAria™ cell sorter (Becton, Dickinson and Company).

Kinetic Data Analysis

The extent of conversion of cell surface displayed peptide substrates was measured directly, using flow cytometry to measure changes in mean fluorescence of clonal cell populations upon protease treatment. Specifically, for each sample, conversion was determined by flow cytometry analyses using the relationship $$\text{Conversion}_{CLiPS} = \frac{FL_- - FL_+}{FL_- - FL_0} \quad [1]$$

where (FL_) is the fluorescence after incubating without enzyme, (FL_+) is fluorescence after incubation with enzyme, and (FL_0) is fluorescence of unlabeled cells. For the recombinant FRET protein reactions, conversion was calculated by dividing the ratiometric FRET signal (yellow fluorescence/cyan fluorescence) by the FRET ratio that results from complete cleavage (Felber et al., Biotechniques 36:878-85 (2004)). For synthetic peptide reactions, conversion was calculated by dividing the fluorescence increase by the fluorescence change due to complete hydrolysis. The reported enteropeptidase $K_M$ for the physiological substrate tripsinogen is 17 μM (Light et al., J Biol Chem 259:13195-8 (1984)), but 600 for short DDDDK (SEQ ID NO:02) peptides (Lu et al., J Mol Biol 292:361-73 (1999)). Given $K_M$ for short peptides is much larger than the substrate concentrations that were used (<5 the Michaelis-Menton model simplifies to $$\frac{d[S]}{dt} \approx -\frac{k_{cat}}{k_M}[S][E] \quad [2]$$

allowing substrate conversion to be expressed as $$\text{Conversion}_{MM} = 1 - \exp\left(-\frac{k_{cat}}{k_M}[E] \cdot t\right) \quad [3]$$

where [S] is the substrate concentration, [E] is enzyme concentration and t is time. To determine the second order rate constant ($k_{cat}/K_M$), the time dependent conversion for each substrate was fit to equation [3]. Reported values represent the average $k_{cat}/k_M$ and standard deviation of three experiments.

Example 1

Development of a Whole-Cell Assay for Peptidase Activity

Figure 3:
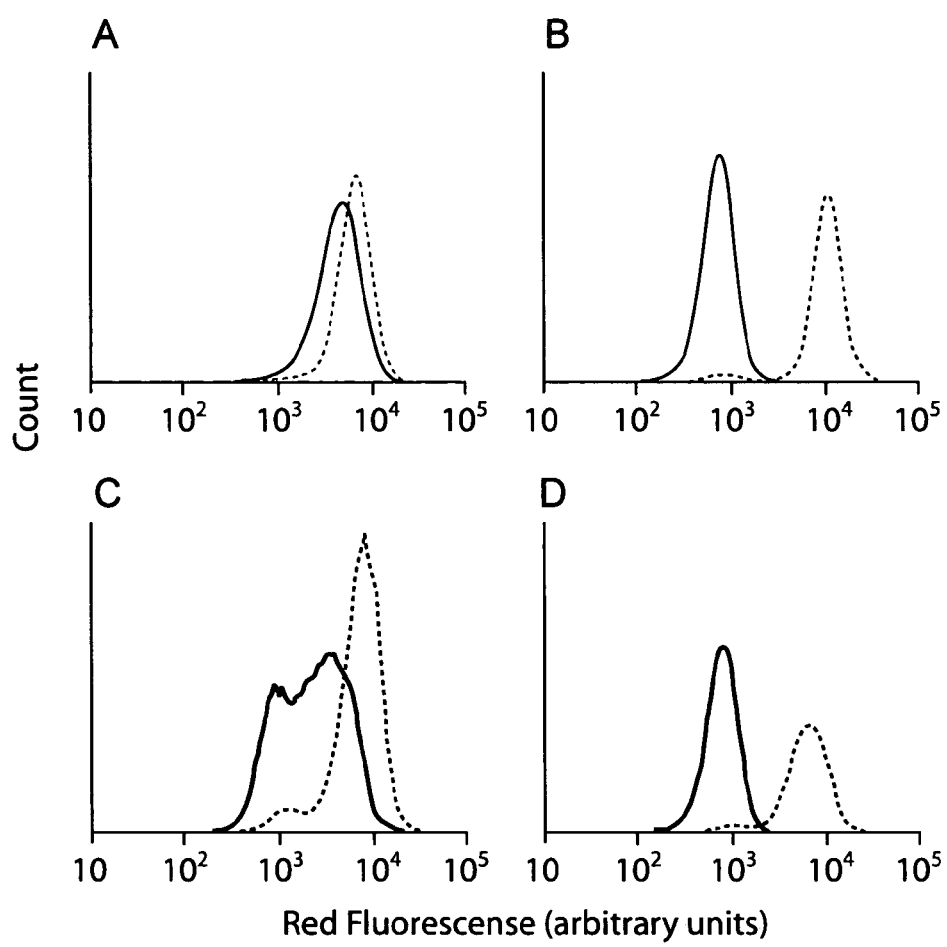
FIG. 3 shows measurement of substrate conversion by FACS. Flow cytometry analysis of bacterial cell populations displaying either a candidate peptide (GGSGGS (SEQ ID NO:01)) (Panel A) or a canonical substrate (DDDDK (SEQ ID NO:02)) (Panel B) before (dashed line) and after (solid line) treatment with enteropeptidase. During library screening for enteropeptidase substrates, cell populations collected from a first screen (Panel C) and a second screen (Panel D) were analyzed by flow cytometry before (dashed line) and after (solid line) enteropeptidase treatment. The loss of fluorescence due to treatment, shown by the shift in the solid line, demonstrates enrichment of enteropeptidase substrates after the second screen (Panel D).

Given the utility of fluorescence-activated cell sorting (FACS) as a quantitative library screening tool, peptidase activity was assayed by displaying reporter-substrates on the surface of *Esherichia coli* (FIG. 1, panel A). Reporter-substrates were designed consisting of a peptide ligand (D) that binds the fluorescent probe streptavidin-R-phycoerythrin (SA-PE) and a peptide substrate oriented such that cleavage removes the SA-PE-binding ligand from the cell surface. In this way, protease activity towards a given substrate would be detectable by monitoring whole-cell fluorescence using FACS. Reporter-substrates were displayed on *E. coli* using circularly permutated outer membrane protein X (CPX), which presents both N- and C-termini on the cell surface, enabling presentation of candidate peptides as non-constrained, terminal fusions (Rice et al., Protein Sci. 15(4):825-36 (2006)). As a control, a substrate-reporter display vector was constructed incorporating a known enteropeptidase cleavage site (DDDDK) (SEQ ID NO:02) flanked by flexible peptide linker sequences, as 'spacers' allowing protease access to the substrate, and a SA-PE binding peptide ligand. Cells displaying the substrate were fluorescently-labeled with SAPE, resulting in a more than twenty-fold increase in mean fluorescence intensity over background autofluorescence, as measured by flow cytometry (FIG. 3). Incubation of this cell population with enteropeptidase before labeling with SAPE resulted in a roughly twenty-fold decrease in mean fluorescence intensity (FIG. 3, panel B), while a negative control cell population displaying the sequence GGQSGQ (SEQ ID NO:44) exhibited minimal change in fluorescence (FIG. 3, panel A). These results demonstrated that enzymatic cleavage of reporter-substrates could be detected as a decrease in fluorescence intensity of cells using FACS and hydrolysis is not due to cleavage outside of the designated substrate region.

A substrate library was constructed in *E. coli* by combinatorial randomization of six sequential amino acid positions within the substrate region to identify optimal substrates for a given protease (FIG. 1, panel A). This cellular library of peptide substrates (CLiPS) comprised a theoretical diversity of $6.4 \times 10^7$ different amino acid sequences. The constructed library contained $1.5 \times 10^8$ independent transformants. Thus, this library is expected to include all possible 5-mer, and 4-mer substrate sequences with >95% and 99% confidence limits, respectively, assuming a random distribution (Bosley et al., *Biomol Eng* 22:57-61 (2005)). Using the whole-cell activity assay, a screening methodology was devised to isolate library members displaying substrates cleaved by a given protease, and thereby identify optimal substrates.

Example 2

Determination of Enteropeptidase and Caspase-3 Specificity Using CLiPS

To demonstrate the general utility of CLiPS, the 6-mer substrate library was screened to identify optimal substrates for two unrelated proteases: caspase-3 and enteropeptidase. These proteases recognize the canonical substrates DEVD↓ (SEQ ID NO:16) (Barrett et al., *Handbook of proteolytic enzymes* (Academic Press, San Diego) (2004)) and DDDDK↓ (SEQ ID NO:02) (Bricteux-Gregoire et al., *Comp Biochem Physiol B* 42:23-39 (1972)), respectively. Caspase-3 was chosen to validate CLiPS, since specificity has been investigated extensively using both substrate phage and fluorogenic substrates (Stennicke et al., *Biochem J* 350 Pt 2, 563-8 (2000); Lien et al., *Protein J* 23:413-25 (2004)). In contrast, enteropeptidase specificity is less well characterized and has been investigated primarily using individually synthesized, fluorogenic substrate variants (Likhareva et al., *Letters in Peptide Science* 9:71-76 (2002)). For each protease, optimal substrates were identified by performing a two-step screen for hydrolysis (FIG. 1). First, library members that display the affinity epitope were purified by sorting (FIG. 1, panel A), thereby removing library members that do not display substrates (i.e. members with stop codons and frameshift mutations). The resulting library population was amplified by growth, treated with protease, labeled with SA-PE, and cells with reduced fluorescence resulting from substrate hydrolysis were collected (FIG. 1, panel B). After three cycles of screening for enteropeptidase substrates, greater than 95% of the enriched library displayed reporter-substrates and exhibited cleavage similar to the canonical substrate (FIG. 3, panels C and D). Therefore, a final sort was performed to identify enteropeptidase substrates that hydrolyzed more rapidly than the canonical substrate.

In applications that involve complex protease-containing mixtures, such as cellular lysates or tissue extracts, we anticipated that specificity could be identified by removing substrates that are cleaved by an appropriate background mixture. For this reason, we investigated whether substrates of a target protease can be determined in the presence of cell lysates. Non-specifically cleaved substrates were first depleted from the library by incubation with *E. coli* lysate protein that does not contain the target protease, caspase-3 (FIG. 1, panel A). Subsequently, cells displaying specifically-cleaved substrates were isolated after incubating the library with lysate from *E. coli* expressing caspase-3 (FIG. 1, panel B). This process ensured that cleavage during screening was due to caspase-3 activity and not endogenous *E. coli* proteolytic activity. Two cycles of screening resulted in the enrichment of library members exhibiting caspase-3 dependent cleavage. Incubation of the enriched library with caspase-3 containing lysates, but not caspase-3 free lysates, resulted in a reduction of the mean fluorescence intensity of the population, as measured by flow cytometry. Single clones from the enriched library were isolated from the remaining population by plating. Thus, CLiPS was capable of identifying caspase-3 specific substrates in the presence of a complex mixture.

Example 3

Characterization of Substrate Cleavage Kinetics

Figure 4:
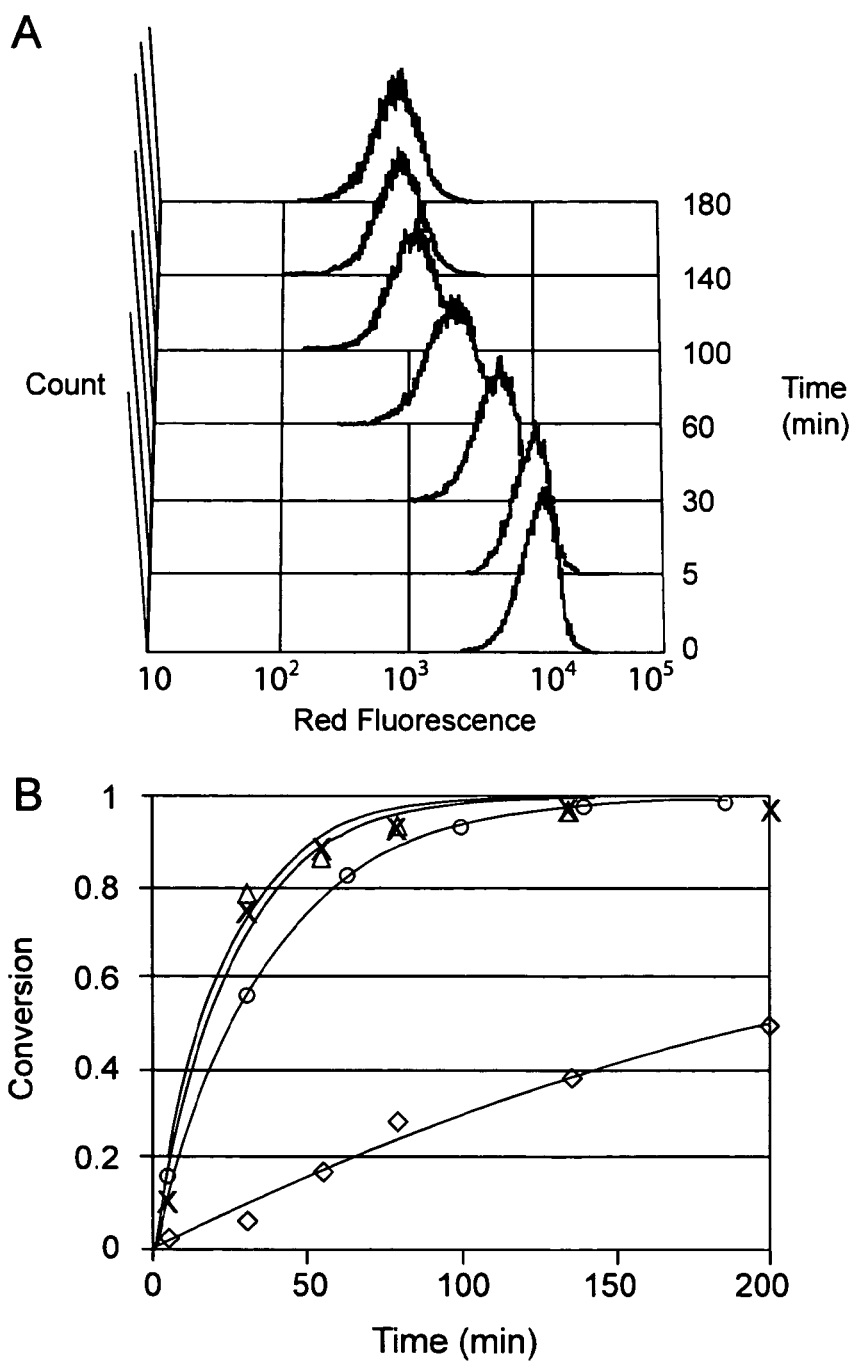
FIG. 4 shows enteropeptidase substrate cleavage kinetics. Panel A shows time-dependent substrate conversion for clone EP 4.1 (VDYRFL (SEQ ID NO:03)) measured by FACS. Panel B is a graph showing average conversion for cell surface displayed enteropeptidase substrates identified using CLiPS: VDYRFL (○) (SEQ ID NO:03), SGDRMW (Δ) (SEQ ID NO:04), and SGERMM (x) (SEQ ID NO:05) with canonical DDDDK (◇) (SEQ ID NO:02). Data was fit to Michaelis-Menton model, which is shown as a line for each substrate.
Figure 6:
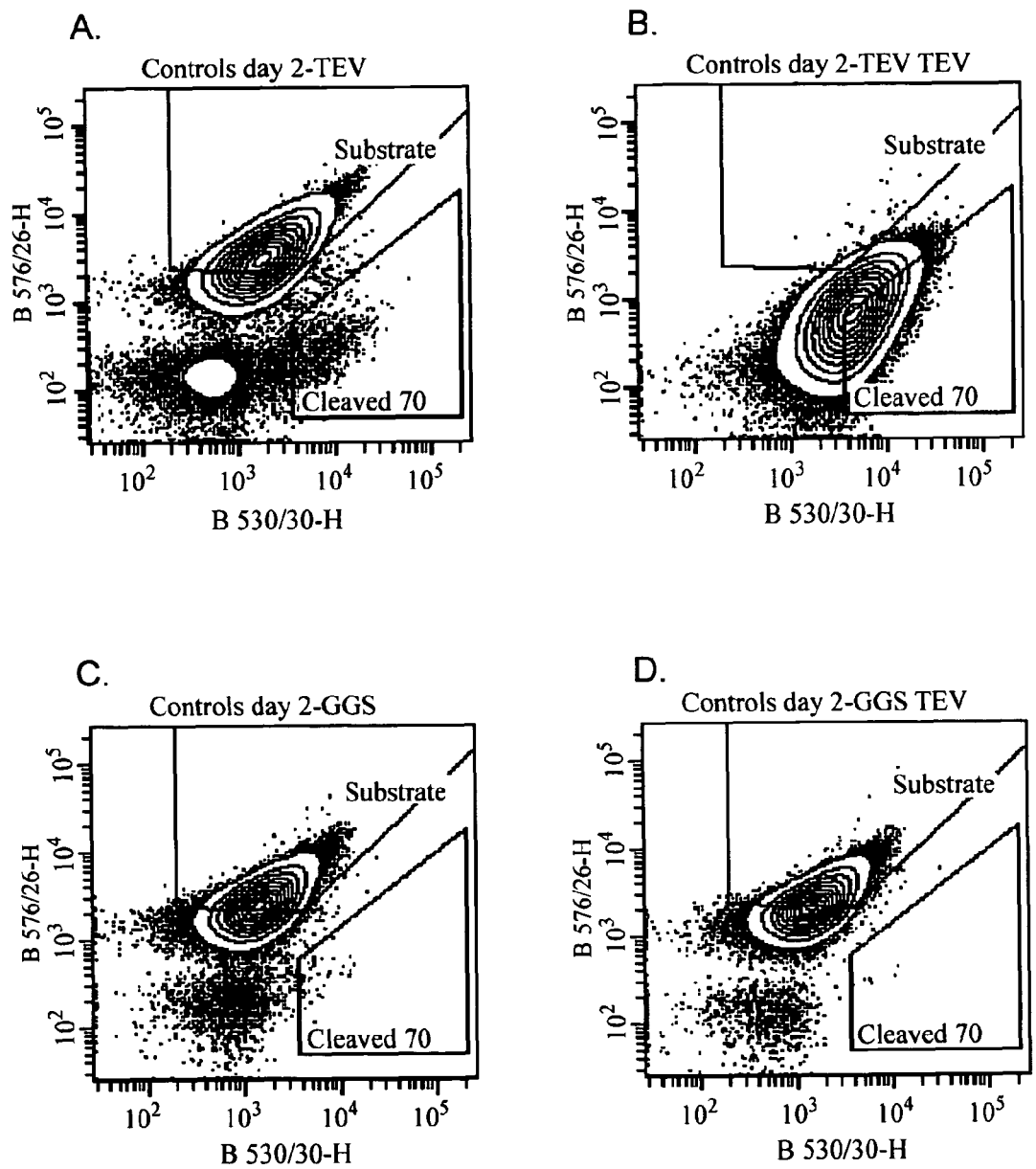
FIG. 6 shows flow cytometric analysis of controls for TEV assays under sorting conditions. Panel A is a plot of control bacteria expressing TEV substrate (ENLYFQS (SEQ ID NO:06)) in the absence of TEV protease. Panel B is a plot of control bacteria expressing TEV substrate (ENLYFQS (SEQ ID NO:06)) in the presence of TEV protease. Panel C is a plot of control bacteria expressing GGSGGS (SEQ ID NO:01) in substrate region in the absence of TEV protease. Panel D is a plot of control bacteria expressing GGSGGS (SEQ ID NO:01) in substrate region in the presence of TEV protease.

The use of multi-copy substrate display on whole cells enabled simple and direct quantitative characterization of cleavage kinetics. Consequently, flow cytometry was used to rank individual isolated clones on the basis of substrate conversion, and those clones exhibiting more than 50% conversion were identified by DNA sequencing (Tables 3 and 4). Substrates efficiently cleaved by caspase-3 revealed a strong substrate consensus of DxVDG (SEQ ID NO:45) (Table 3), in agreement with the known specificity of caspase-3. The substrates identified for enteropeptidase shared a consensus sequence of $^D/_E$RM, indicating a substrate preference at the P1' position (Table 3). Interestingly, enteropeptidase substrates identified by CLiPS were cleaved more rapidly than the canonical sequence, DDDDK (SEQ ID NO:2) (Table 4). Four isolated clones with high conversion were investigated further to quantify cleavage kinetics. Clones exhibiting multiple arginine residues were excluded to avoid substrates that may have multiple cleavage sites. Individual substrate displaying clones (e.g. EP4.1) exhibited uniform substrate turnover (FIG. 4, panel A), as determined by flow cytometry. In this way, the extent of conversion for each clone could be determined at several different time points and fit to a Michaelis-Menton model (FIG. 4, panel B). The observed second order rate constant ($k_{cat}/K_M$) for the most rapidly cleaved substrate (EP4.3 SGDRMW (SEQ ID NO:04)) was 13-fold greater than that for the canonical substrate DDDDK (SEQ ID NO:02) (Table 4).

To determine how cleavage kinetics ($k_{cat}/K_M$) measured using surface displayed reporter substrates relate to those measured in solution, two independent approaches were applied to measure $k_{cat}/K_M$ for soluble substrates. Since enteropeptidase is often used to remove peptide affinity tags, substrates were assayed in the context of a fusion protein. Specifically, fluorogenic substrates were constructed using fluorescent proteins that exhibit Föster resonance energy transfer (FRET) (CyPet and YPet) (Nguyen et al., *Nat Biotechnol* 23:355-60 (2005)) and were used to determine protease cleavage kinetics as described previously (Felber et al., *Biotechniques* 36:878-85 (2004)). CyPet-YPet substrates for enteropeptidase having recognition sequences of DDDDKG (SEQ ID NO:46), GGSGGS (SEQ ID NO:01), or four sequences identified by CLiPS (EP4.1, EP4.2, EP4.3 or EP4.6) were constructed, expressed in *E. coli*, and purified. Substrate conversion by enteropeptidase was measured in real-time by fluorimetry and fit to Michaelis-Menton kinetics (Table 4). In relative agreement with whole-cell assays, the CLiPS substrate, SGDRMW (SEQ ID NO:04), cleaved at a rate 17-fold faster than DDDDK (SEQ ID NO:02). Absolute values of $k_{cat}/K_M$ for cell-surface-tethered and soluble substrates differed systematically, but importantly, the relative ranking of the cleavage rates of individual substrates was identical in either context. To further confirm the improved hydrolysis rate for the SGDRMW (SEQ ID NO:04) substrate, relative to DDDDK (SEQ ID NO:02), fluorogenic peptide substrates were synthesized and cleavage was measured using fluorimetry (Table 4). The $k_{cat}/K_M$ of the CLiPS identified substrate SGDRMW (SEQ ID NO:04) was more than five-fold higher than that of DDDDK (SEQ ID NO:02). Collectively, these results demonstrate that whole-cell fluorescence assays provide a reliable means to quantitatively measure and rank cleavage kinetics of individual substrate sequences, and that CLiPS enables identification of substrates with improved cleavage kinetics.

TABLE 3

Caspase-3 substrates identified using CLiPS

| Substrate | | P5 | P4 | P3 | P2 | P1 | P1' | P2' | P3' | P4' | Conversion |
|---|---|---|---|---|---|---|---|---|---|---|---|
| Canonical | (SEQ ID NO: 47) | Q | D | E | V | D | G | G | Q | S | 0.95 ± 0.03 |
| CS 2.7 | (SEQ ID NO: 48) | S | D | G | V | D | G | W | G | G | 0.95 |
| CS 2.14 (4) | (SEQ ID NO: 49) | S | D | V | V | D | G | W | G | G | 0.94 ± 0.03 |
| CS 2.2 | (SEQ ID NO: 50)3 | S | D | G | V | D | G | V | G | G | 0.93 |
| CS 2.11 | (SEQ ID NO: 51) | G | G | S | L | D | T | W | T | A | 0.81 |
| CS 2.20 (2) | (SEQ ID NO: 52) | L | D | T | V | D | R | G | G | Q | 0.79 ± 0.01 |
| CS 2.59 | (SEQ ID NO: 53) | S | D | S | T | D | S | G | G | G | 0.79 |
| CS 2.1 | (SEQ ID NO: 54) | G | S | Q | V | D | G | V | G | G | 0.75 |
| CS 2.26 | (SEQ ID NO: 55) | G | S | E | V | D | G | R | H | G | 0.75 |
| CS 2.56 | (SEQ ID NO: 56) | S | T | E | V | D | G | P | G | G | 0.75 |
| CS 2.47 | (SEQ ID NO: 57) | G | S | E | V | D | G | G | W | G | 0.74 |

TABLE 3-continued

Caspase-3 substrates identified using CLiPS

| Substrate | | P5 | P4 | P3 | P2 | P1 | P1' | P2' | P3' | P4' | Conversion |
|---|---|---|---|---|---|---|---|---|---|---|---|
| CS 2.10 | (SEQ ID NO: 58) | T | D | G | T | D | G | G | G | Q | 0.72 |
| CS 2.62 | (SEQ ID NO: 59) | Q | D | G | V | D | T | G | G | Q | 0.70 |
| CS 2.2 | (SEQ ID NO: 60) | G | S | E | V | D | G | S | R | G | 0.67 |
| CS 2.4 | (SEQ ID NO: 61) | G | S | Y | V | D | G | V | V | G | 0.64 |
| CS 2.33 | (SEQ ID NO: 62) | S | D | F | V | D | R | V | G | G | 0.59 |
| CS 2.36 (2) | (SEQ ID NO: 63) | G | S | M | V | D | G | A | M | G | 0.56 ± 0.05 |
| Consensus | (SEQ ID NO: 64) | X | D | X | V | D | G | | | | |

TABLE 4

Enteropeptidase substrates identified using CLiPS

| Substrate | | P5 | P4 | P3 | P2 | P1 | P1' | P2' | P3' | P4' | Conversion |
|---|---|---|---|---|---|---|---|---|---|---|---|
| Canonical | (SEQ ID NO: 65) | D | D | D | D | K | G | G | Q | S | 0.15 ± 0.08 |
| ER 4.3 | (SEQ ID NO: 66) | S | S | G | D | R | M | W | G | G | 0.97 ± 0.01 |
| ER 4.6 | (SEQ ID NO: 67) | S | S | G | E | R | M | M | G | G | 0.93 ± 0.03 |
| ER 4.7 | (SEQ ID NO: 68) | G | S | O | D | R | R | A | G | G | 0.91 ± 0.03 |
| ER 4.8 | (SEQ ID NO: 69) | V | R | D | Y | R | M | G | G | Q | 0.87 ± 0.04 |
| ER 3.6 | (SEQ ID NO: 70) | G | S | S | D | R | A | K | V | W | 0.86 ± 0.05 |
| ER 4.1 | (SEQ ID NO: 71) | S | V | D | Y | R | F | L | G | S | 0.84 ± 0.02 |
| ER 4.2 | (SEQ ID NO: 72) | M | H | G | E | R | M | G | G | S | 0.84 ± 0.02 |
| ER 2.5 | (SEQ ID NO: 73) | M | S | G | E | R | M | G | G | S | 0.84 ± 0.03 |
| ER 4.10 | (SEQ ID NO: 74) | G | S | S | E | R | A | A | A | G | 0.78 ± 0.02 |
| ER 4.9 | (SEQ ID NO: 75) | S | V | L | D | R | W | M | G | G | 0.72 ± 0.05 |
| ER 4.4 | (SEQ ID NO: 76) | S | E | Y | D | R | Q | L | G | 5 | 0.71 ± 0.01 |
| ER 2.2 | (SEQ ID NO: 77) | A | A | V | E | R | W | G | G | 5 | 0.69 ± 0.14 |
| Consensus | (SEQ ID NO: 78) | | X | X | $^d/_E$ | R | M | X | | | |

While the primary physiological function of enteropeptidase is to activate trypsin, knowledge of enteropeptidase's recognition sequence, DDDDK (SEQ ID NO:02), and its tolerance for various amino acids at P1' (Hosfield et al., *Anal Biochem* 269:10-6 (1999)) have contributed to widespread use of this enzyme in protein purification applications. Typically, only the catalytic subunit is used since it exhibits an activity similar to the full length protein (Light et al., *J Biol Chem* 259:13195-8 (1984)). Enteropeptidase specificity has been investigated previously by comparing natural substrate sequences and by measurement of the hydrolysis rates of synthetic fluorogenic peptides (Bricteux-Gregoire et al., *Comp Biochem Physiol B* 42:23-39 (1972); Likhareva et al., *Letters in Peptide Science* 9:71-76 (2002); Light et al., *Anal Biochem* 106:199-206 (1980); Matsushima et al., *J Biochem (Tokyo)* 125:947-51 (1999)). However, substrate specificity has not been characterized in detail by screening combinatorial peptide libraries, despite the obvious importance of identifying unwanted secondary cleavage sites in fusion proteins (Likhareva et al., (2002)). Application of CLiPS to enteropeptidase revealed a remarkably broad substrate specificity, with a strong preference for arginine at P1, and one or more Asp or Glu residues at P2 or P3. While libraries constructed using NNS codons are expected to have a 3:1 ratio of Arg to Lys residues consistent with codon usage, the observed ratio (12:0) indicates a preference for arginine over lysine at the P1 position. Interestingly, the P1' position in those substrates with the highest levels of conversion was predominantly occupied by methionine, indicating for the first time that the positions carboxy-terminal to the scissile bond influence activity. CLiPS resulted in identification of a rapidly cleaved enteropeptidase substrate (SGDRMW) (SEQ ID NO:4), exhibiting a 17-fold faster cleavage than the DDDDK (SEQ ID NO:02) substrate, in the context of a fusion protein. The contextual dependence of substrate cleavage rates could reflect differences in substrate conformation and accessibility that are known to influence proteolysis (Hazebrouck et al., *Biochem J* 358:505-10 (2001); Coombs et al., *J Biol Chem* 273:4323-8 (1998)). Previously, others have observed differences in the rates of cleavage of surface-tethered peptide substrates and free substrates in solution prompting the use of relative $k_{cat}/K_M$ values for comparisons (Barrios et al., *Bioorg Med Chem Lett* 12:3619-23 (2002)). Nevertheless, the rapidly cleaved substrate SGDRMW (SEQ ID NO:04) identified here is useful in protein purification applications, since less enzyme or shorter reactions times could be used to harvest desired proteins, thereby minimizing unwanted hydrolysis that occurs at secondary sites (Sharma et al., *Proc Natl Acad Sci USA* 91:9337-41 (1994)).

Caspase-3, referred to as an executioner caspase of the apoptotic cascade, hydrolyzes a large number of different substrates that carry out the apoptotic program (Nicholson et al., *Cell Death Differ* 6:1028-42 (1999)). Given the importance of this enzyme in biology, substrate specificity has been investigated using several different approaches including a 4-mer substrate phage library (Lien et al., *Protein J* 23:413-25 (2004)) and by comparison of the activities towards a panel of fluorogenic substrates differing by single residues (Stennicke et al., *Biochem J* 350 Pt 2:563-8 (2000)). Collectively, these studies have clearly identified a consensus cleavage sequence of $Dx^V/_LDG$ (SEQ ID NO:79). Secondary analysis of substrate phage clones, using synthetic fluorogenic peptides revealed that substrates with the highest conversion also possessed a DxVD (SEQ ID NO:80) consensus (Lien et al., *Protein J* 23:413-25 (2004)). Consistent with these results, positional scanning with synthetic peptides indicated a preference for aspartic acid and glycine at the P4 and P1' positions, respectively (Stennicke et al., (2000)). In the present study, two rounds of screening with unpurified caspase-3-containing samples yielded an unambiguous consensus (Dx-VDG) (SEQ ID NO:81) consistent with previous reports. These results show that CLiPS does not require purified enzyme preparations, since two-step screening favors removal of substrates cleaved by endogenous *E. coli* proteases to identify target specific sequences. Such an approach is useful for identifying tissue or disease-specific protease substrates (Boder et al., *Nat Biotechnol* 15:553-7 (1997)) that indicate the presence of protease markers with high sensitivity or that enhance the specificity of therapeutics or imaging agents.

Example 4

Dual-Signal CLiPS

Figure 2:
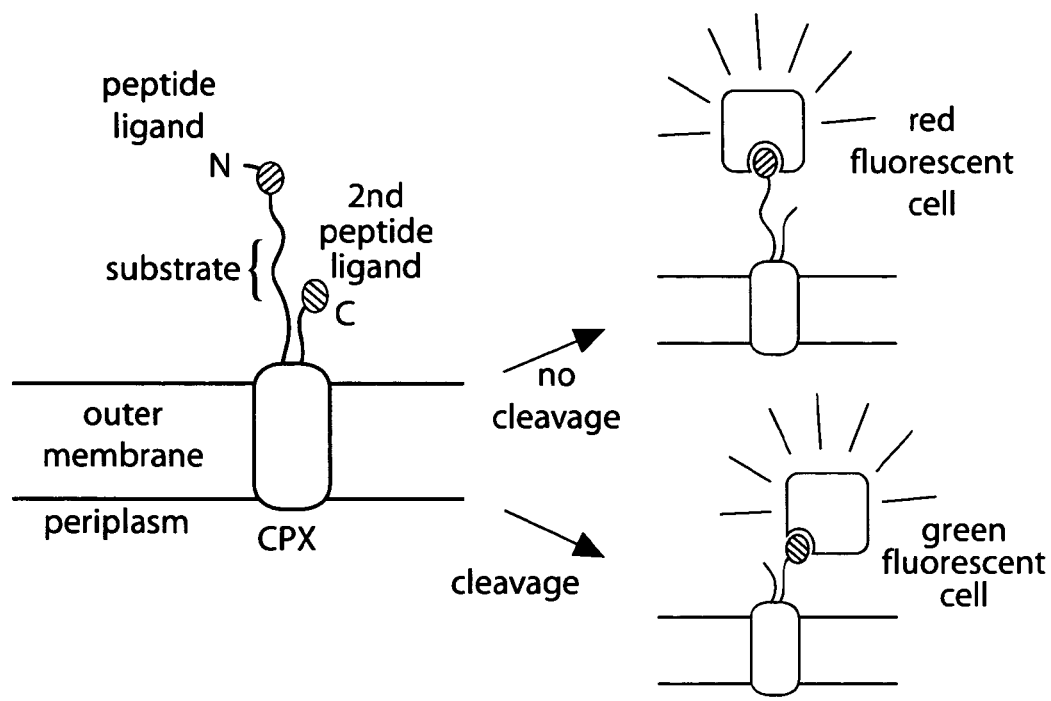
FIG. 2 shows a schematic diagram of a dual color CLiPS screening method. In the absence of a cleavage, a first fluorescent signal is detected and when cleavage occurs, a second fluorescent signal different form the first fluorescent signal is detected.

The dual-signal CLiPS method utilizes the N-terminus and C-terminus of CPX to display a candidate peptide on each terminus, where the candidate peptide displayed on the N-terminus is different than candidate peptide displayed on the C-terminus, and a detectable moiety at each terminus, where the second detectable moiety is different that the first detectable moiety (FIG. 2). This increases sorting efficiency as the cells that are not expressing the display scaffold are not carried over when sorting for proteolytic cleavage events. For example, where cleavage of the candidate peptide does not occur, a signal from the first detectable moiety on the N-terminus is detected. However, if cleavage of the candidate peptide does occur, a signal from the second detectable moiety on the C-terminus is detected. The dual-signal system ensures that only cells that properly expressed the display scaffold containing the candidate peptide are retained. Labeling conditions and detectable moiety positioning can be manipulated such that occupancy of the N-terminal peptide affinity ligand by a detectable label decreases efficiency of C-terminal labeling. As shown in FIG. 3, this system creates an increase in C-terminal labeling upon cleavage, leading to further separation between cells with intact N-termini (FIG. 5, top panel) and cleaved N-termini (FIG. 5, bottom panel). Using the dual-signal method, the substrates for tobacco etch virus protease (TEV) and matrix metalloprotease-1 (MMP-1) were mapped, as detailed below.

Dual-Signal CLiPS Screen for TEV Substrates

Figure 7:
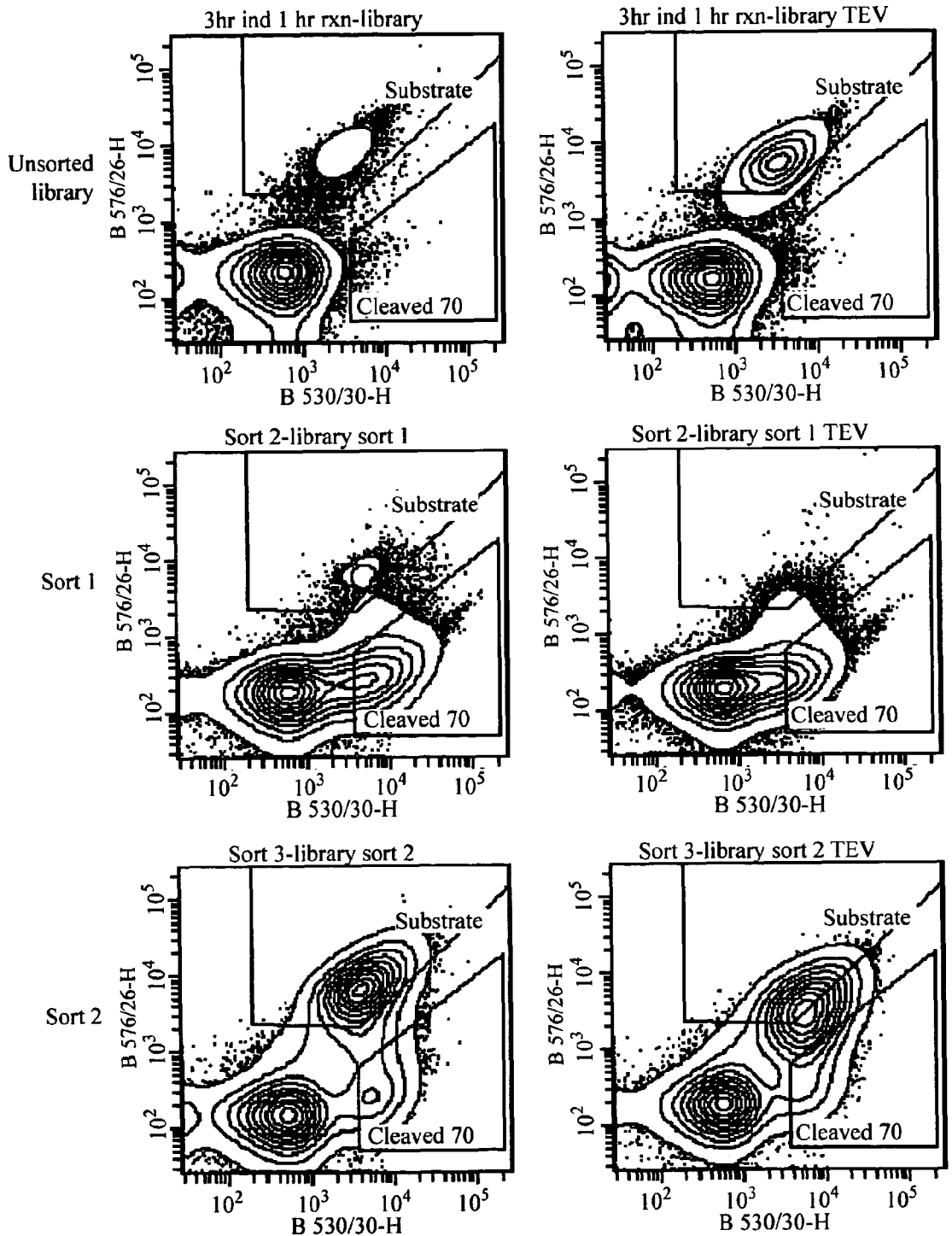
FIG. 7 shows flow cytometric analysis of sorts 1 and 2 with unsorted 5× library in the presence and absence of TEV. The term "5× library" refers to a library of cells presenting a library of 5 amino acid long peptides.
Figure 8:
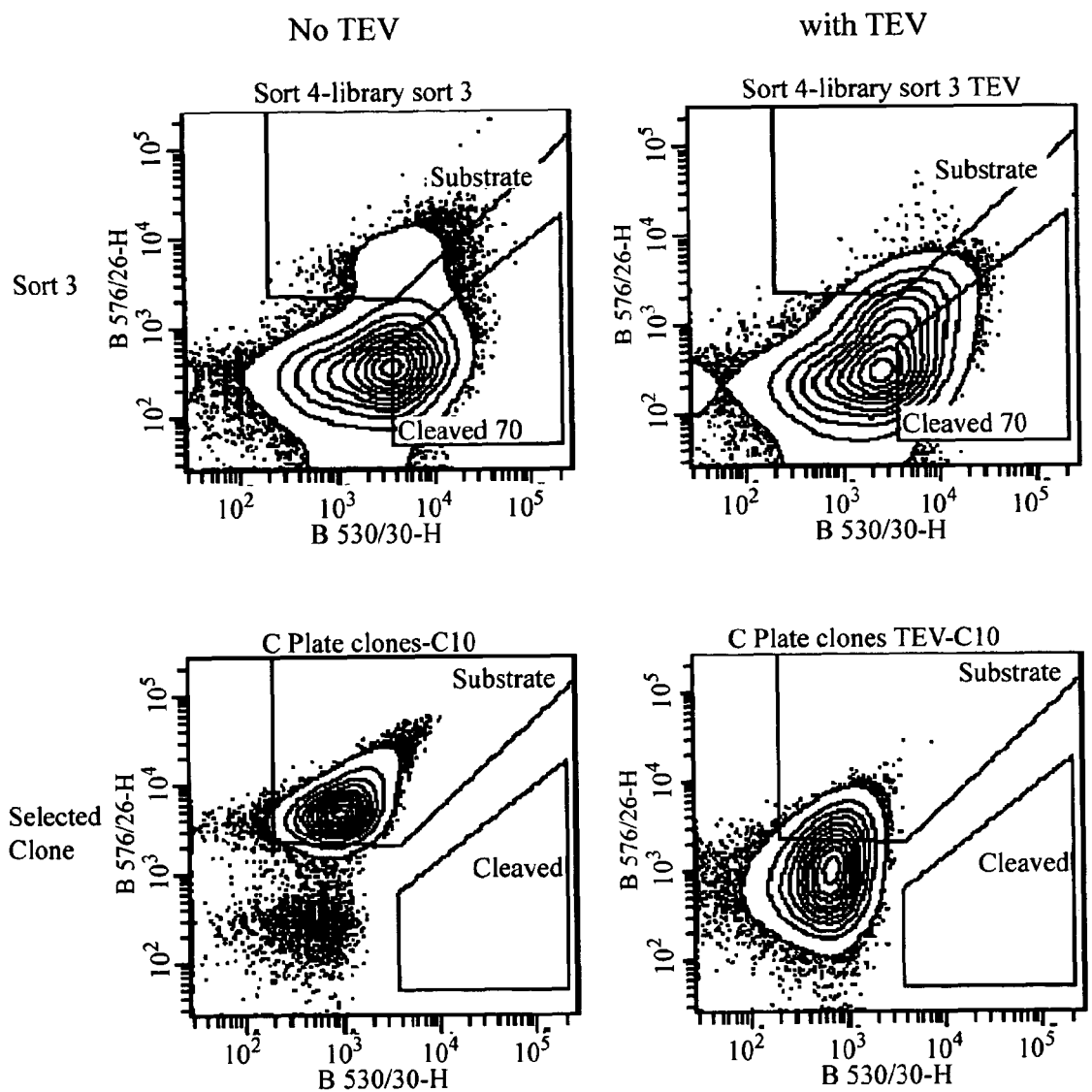
FIG. 8 shows flow cytometric analysis of cell populations after sort 3 in the presence and absence of TEV treatment (top panels). Flow cytometric analysis of representative clonal population C10 (PEVIY (SEQ ID NO:07) labeled with SAPE only and used for conversion calculations is provided in the bottom panels.

The reaction buffer for TEV assays was 50 mM Tris-Cl pH 8.0 supplemented with 20 mM NaCl and 2 mM $CaCl_2$. Four sorts were completed for TEV substrates by alternating between sorting cells that display substrates in the absence of any added enzyme and sorting cells with hydrolyzed substrates after enzyme treatment. Controls were used to set sort gates (FIG. 3). FIG. 3 shows positive controls in the absence (panel A) and presence (panel B) of TEV and negative controls in the absence (panel C) and presence (panel D) of TEV. Sorts for enteropeptidase hydrolysis (1 and 3) were performed after reactions with 10 units of AcTEV in 11 μL for 1 hr (FIGS. 7 and 8). To remove clones from the library pool that did not properly display the substrate and binding peptide (e.g., stop codons or frame shift mutations), cells were sorted (2 and 4) after 1 hr incubation in the reaction buffer without enzyme (FIGS. 7 and 8). The final sort was sorted to 96-well plate for individual clone analysis. 76 clones from the 96-well plate were subcultured into 200 μL fresh LB and cells were treated as described above. The clones were sequenced and ranked based on hydrolysis after 1 hr with 10 units of TEV (Tables 5A-C and 6).

Alignment of TEV Substrates from 5× Library Grouped by Conversion

TABLE 5A

| 60%-90% Conversion | |
|---|---|
| Name | Sequence |
| B02 (SEQ ID NO: 82) | EELY--- |
| H06 (SEQ ID NO: 83) | EELW--- |
| C10 (SEQ ID NO: 07) | PEVIY--- |
| D07 (SEQ ID NO: 84) | REVLY--- |
| D03 (SEQ ID NO: 85) | ENVYFQS |
| E03 (SEQ ID NO: 86) | -ENVYFQS |
| D11 (SEQ ID NO: 87) | GEEVY--- |
| H07 (SEQ ID NO: 88) | EEAVL--- |
| D01 (SEQ ID NO: 89) | DVQLY--- |
| D10 (SEQ ID NO: 90) | ---LYFQG |
| D02 (SEQ ID NO: 91) | DSELY--- |
| F04 (SEQ ID NO: 92) | DRELY--- |

TABLE 5A-continued

60%-90% Conversion

| Name | | Sequence |
|---|---|---|
| E11 | (SEQ ID NO: 93) | WESLY--- |
| B09 | (SEQ ID NO: 94) | LEQLI--- |
| D08 | (SEQ ID NO: 95) | LEWLK--- |
| F03 | (SEQ ID NO: 96) | LESLV--- |
| C04 | (SEQ ID NO: 97) | -RRMAE-- |
| G05 | (SEQ ID NO: 98) | LRELW--- |
| F09 | (SEQ ID NO: 99) | GEDLL--- |
| H09 | (SEQ ID NO: 100) | GEALF--- |
| D09 | (SEQ ID NO: 101) | MEMLR--- |
| E09 | (SEQ ID NO: 102) | SEPLR--- |
| G06 | (SEQ ID NO: 103) | SEDLW--- |
| G08 | (SEQ ID NO: 104) | MEWLW--- |
| H08 | (SEQ ID NO: 105) | WEPLW--- |
| Consensus | | E LY |

TABLE 5B

50%-60% Conversion

| Name | | Sequence |
|---|---|---|
| A05 | (SEQ ID NO: 107) | FEDLL |
| H04 | (SEQ ID NO: 108) | MEDLM |
| B07 | (SEQ ID NO: 109) | MEEVY |
| C11 | (SEQ ID NO: 110) | DGALY |
| F05 | (SEQ ID NO: 111) | DRELY |

TABLE 5B-continued

50%-60% Conversion

| Name | | Sequence |
|---|---|---|
| E07 | (SEQ ID NO: 112) | ETILY |
| D04 | (SEQ ID NO: 113) | GEALF |
| F11 | (SEQ ID NO: 114) | GEPLW |
| E01 | (SEQ ID NO: 115) | EEYLW |
| F07 | (SEQ ID NO: 116) | EENLG |
| Consensus | (SEQ ID NO: 117) | EE LY |

TABLE 5C

30%-50% conversion

| Name | | Sequence |
|---|---|---|
| A06 | (SEQ ID NO: 118) | FEDGL |
| B11 | (SEQ ID NO: 119) | GETVY |
| C09 | (SEQ ID NO: 120) | RELVY |
| C07 | (SEQ ID NO: 121) | VEPIY |
| C05 | (SEQ ID NO: 122) | REVGY |
| E05 | (SEQ ID NO: 123) | RDDGY |
| G03 | (SEQ ID NO: 124) | GDNGY |
| H03 | (SEQ ID NO: 125) | ARQIR |
| H11 | (SEQ ID NO: 126) | AEWGR |
| D05 | (SEQ ID NO: 127) | GEAGV |
| G02 | (SEQ ID NO: 128) | GEAGF |
| F02 | (SEQ ID NO: 129) | EEYLW |
| Consensus | (SEQ ID NO: 130) | GE LY |

TABLE 6

Conversion Data for Top TEV Substrates From 5X Library

| Name | | Sequence | % Conversion | F1 | F1 after TEV |
|---|---|---|---|---|---|
| D01 | (SEQ ID NO: 131) | GEVLW | 0.87 | 3839 | 725 |
| C10 | (SEQ ID NO: 07) | PEVIY | 0.81 | 6109 | 1381 |
| F04 | (SEQ ID NO: 132) | DRELY | 0.79 | 5906 | 1421 |
| E11 | (SEQ ID NO: 133) | WESLY | 0.77 | 5049 | 1362 |
| B09 | (SEQ ID NO: 134) | LEQLI | 0.76 | 3254 | 980 |
| H08 | (SEQ ID NO: 135) | WEPLW | 0.73 | 3971 | 1252 |
| B02 | (SEQ ID NO: 136) | EEELY | 0.72 | 3266 | 1081 |
| F09 | (SEQ ID NO: 137) | GEDLL | 0.71 | 4809 | 1552 |
| H07 | (SEQ ID NO: 138) | EEAVL | 0.71 | 2992 | 1043 |

TABLE 7

Clones from TEVopt Library with Highest Conversion after 2 Hour Incubation with 2 Units of TEV

| Name | Sequence | | % Conversion |
|---|---|---|---|
| A3 | (SEQ ID NO: 139) | ALYIQG | 0.92212 |
| A1 | (SEQ ID NO: 140) | FLYLQG | 0.918387 |
| E4 | (SEQ ID NO: 141) | SLYVQG | 0.863465 |
| A4 | (SEQ ID NO: 142) | VLYLQS | 0.854432 |
| C3 | (SEQ ID NO: 143) | DLYWQG | 0.733768 |
| D5 | (SEQ ID NO: 144) | SLYWQG | 0.716599 |
| C4 | (SEQ ID NO: 145) | ELYWQG | 0.689173 |
| D1 | (SEQ ID NO: 146) | WLYLQG | 0.680478 |
| Control | (SEQ ID NO: 06) | ENLYFQS | 0.663577 |
| C6 | (SEQ ID NO: 147) | QLYFQS | 0.617894 |
| B6 | (SEQ ID NO: 148) | EVYVQG | 0.610145 |
| C5 | (SEQ ID NO: 149) | ELYAQG | 0.588389 |
| E6 | (SEQ ID NO: 150) | VLYTQG | 0.548951 |
| A2 | (SEQ ID NO: 151) | DVYVQG | 0.526409 |
| D4 | (SEQ ID NO: 152) | LLYIQG | 0.516773 |

The results from the clones obtained by TEV sorting identified a strong consensus of X-E-X-(L/V)-(Y/W)-X (SEQ ID NO:153) in the substrate region with cleavage in the linker region. Based on this consensus a second library was created to identify the optimum TEV substrate that codes for E-X-(LN)-(Y/W/S/stop)-X-X-X (SEQ ID NO:154). This library was sorted using only 2 units of TEV (versus 10 from previous sorts) and sorts were carried out after 1 hour of reaction. The final sort 5 was onto agar plates and individual clones were assayed using Guava EasyCyte plate reading cytometer. This machine enabled identification clones with similar kinetics the TEV control ENLYFQS (SEQ ID NO:06) (Table 7). The top clones were further characterized in triplicate for multiple time points showing the top clones are marginally better than the previously reported sequence.

Dual-Signal CLiPS Screen for MMP-1 Substrates

Figure 9:
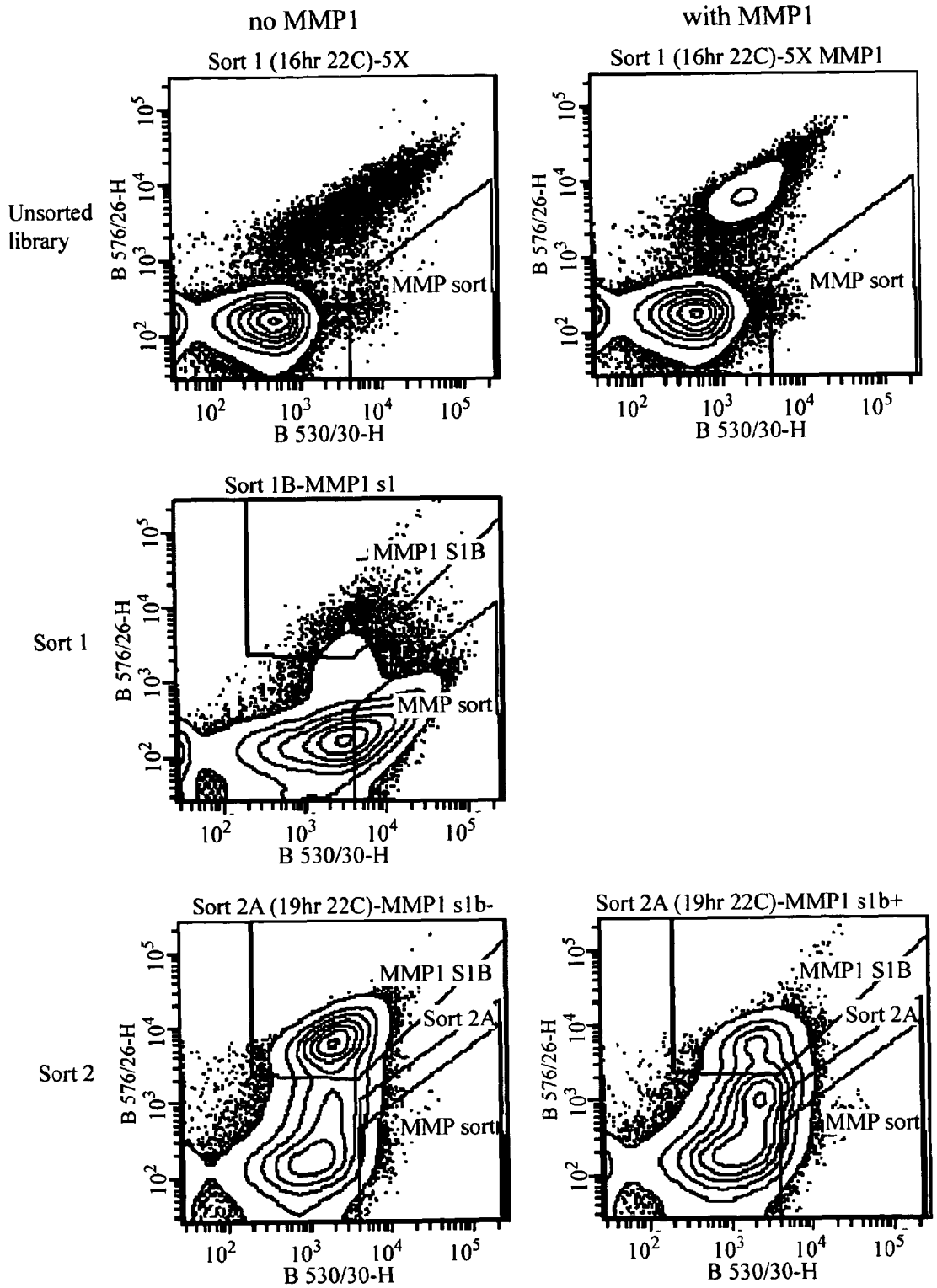
FIG. 9 shows flow cytometric analysis of sorts of 5× library for candidate MMP substrates in the presence and absence of MMP.
Figure 10:
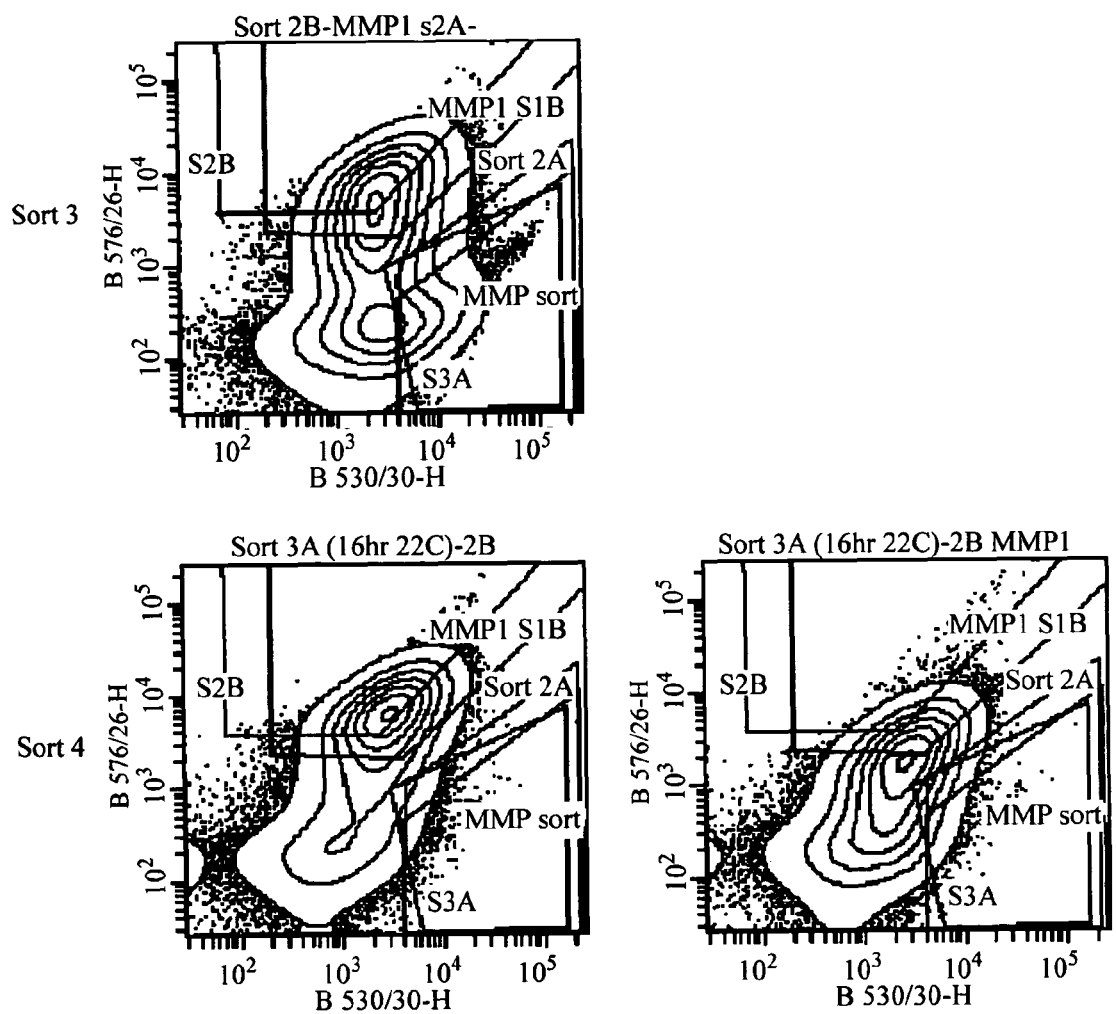
FIG. 10 shows flow cytometric analysis of cell populations after sorts 3 and sort 4 for MMP-1 substrates from 5× library in the presence and absence of MMP.

The MMP-1 assays were performed by incubating cells with 1.5 pM MMP-1. Sorts for hydrolysis were performed after 16 hrs, 19 hrs, and 16 hrs for sorts 1, 3 and 5, respectively (FIGS. 9 and 10). Enrichment after 4 sorts can be seen by the fluorescence shift due to MMP-1 incubation (FIG. 10) and this population was sorted a final time for hydrolyzed substrates. These clones were sequences and assayed for conversion (Table 8). These data was then confirmed by repetition at multiple time points. Many of these sequences have been reported as MMP-1 substrates. However, substrates of MMP-1 with amino acids M and L at positions P1 and P3 have not previously been reported. This data shows that the system can be used to identify substrates from a library of peptides for a particular enzyme.

TABLE 8

Conversion of MMP Substrates from sort 4 of 5X Library.

| Sequence | | %Conversion |
|---|---|---|
| VPLNM | (SEQ ID NO: 155) | 0.844 |
| VPMVV | (SEQ ID NO: 156) | 0.814 |
| PVNVV | (SEQ ID NO: 157) | 0.789 |
| VPVNM | (SEQ ID NO: 158) | 0.760 |
| PVANR | (SEQ ID NO: 159) | 0.729 |
| PMAVI | (SEQ ID NO: 160) | 0.699 |
| MPLVM | (SEQ ID NO: 161) | 0.659 |
| VPLNM | (SEQ ID NO: 162) | 0.610 |
| PMAVT | (SEQ ID NO: 163) | 0.504 |
| PVPMV | (SEQ ID NO: 164) | 0.496 |
| VPMVV | (SEQ ID NO: 165) | 0.443 |
| MPVVL | (SEQ ID NO: 166) | 0.428 |
| TPLAL | (SEQ ID NO: 167) | 0.417 |
| VPVVM | (SEQ ID NO: 168) | 0.366 |

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A peptide display scaffold, comprising a fusion protein comprising:
a $D_1$ moiety positioned N-terminal to a $C_1$ moiety in the fusion protein, which $C_1$ moiety is positioned N-terminal to a TM moiety in the fusion protein, which TM moiety is positioned N-terminal to a $D_2$ moiety in the fusion protein; or
a $D_2$ moiety positioned N-terminal to a TM moiety in the fusion protein, which TM moiety is positioned N-terminal to a $C_1$ moiety in the fusion protein, which $C_1$ moiety is positioned N-terminal to a $D_1$ moiety in the fusion protein; wherein
the TM moiety is a circularly permuted bacterial outer membrane protein;
the $C_1$ moiety comprises a candidate peptide; and
the $D_1$ and $D_2$ moieties are first and second detectable moieties, wherein the $D_1$ and $D_2$ moieties are not the same, wherein the $D_1$ moiety and the $D_2$ moiety are each a heterologous peptide or polypeptide relative to the circularly permuted bacterial outer membrane protein, and wherein, when the fusion protein is expressed in a cell comprising a cell outer membrane, the $D_1$, $C_1$ and $D_2$ moieties are exposed at an extracellular surface of the cell outer membrane and one or both of the N- and C-termini of the fusion protein are exposed at the extracellular surface of the cell outer membrane.

2. The peptide display scaffold of claim 1, wherein the fusion protein comprises at least one linker, wherein the linker is between the $C_i$ moiety and the TM moiety or between the $D_2$ moiety and the TM moiety.

3. The peptide display scaffold of claim 1, wherein detectable moieties $D_1$ and $D_2$ are first and second affinity tags which are not the same.

4. The peptide display scaffold of claim 1, wherein the fusion protein comprises a $C_2$ moiety between the TM moiety and the $D_2$ moiety, wherein the fusion protein comprises
the $D_1$ moiety positioned N-terminal to the $C_1$ moiety in the fusion protein, which $C_1$ moiety is positioned N-terminal to the TM moiety in the fusion protein, which TM moiety is positioned N-terminal to the $C_2$ moiety in the fusion protein, which $C_2$ moiety is positioned N-terminal to the $D_2$ moiety in the fusion protein; or
the $D_2$ moiety positioned N-terminal to the $C_2$ moiety in the fusion protein, which $C_2$ moiety is positioned N-terminal to the TM moiety in the fusion protein, which TM moiety is positioned N-terminal to the $C_1$ moiety in the fusion protein, which $C_1$ moiety is positioned N-terminal to the $D_1$ moiety in the fusion protein;
wherein the $C_2$ moiety comprises a candidate peptide, and the $C_1$ and $C_2$ moieties are not the same, and wherein when the fusion protein is expressed in the cell, the $D_1$, $C_1$, $C_2$ and $D_2$ moieties are exposed at the extracellular surface of the cell outer membrane.

5. The peptide display scaffold of claim 4, wherein the fusion protein comprises at least one linker, wherein the linker is between the $C_1$ moiety and the TM moiety or between the $C_2$ moiety and the TM moiety.

6. The peptide display scaffold of claim 4, wherein detectable moieties $D_1$ and $D_2$ are first and second affinity tags which are not the same.

7. A method for identifying a peptide ligand of an enzyme, comprising:
contacting a cell expressing a peptide display scaffold according to claim 4 with an enzyme; and
detecting the presence or absence of a $D_1$ signal and a $D_2$ signal, wherein said detecting indicates whether $C_2$ comprises a peptide ligand for the enzyme.

8. The peptide display scaffold of claim 1, wherein the $C_1$ moiety comprises a member of a library of candidate peptide substrates for an enzyme.

9. The peptide display scaffold of claim 1, wherein the fusion protein comprises a linker between the $C_1$ moiety and the TM moiety and a linker between the $D_2$ moiety and the TM moiety.

10. The peptide display scaffold of claim 1, wherein at least one of detectable moieties $D_1$ and $D_2$ is an affinity tag.

11. The peptide display scaffold of claim 1, wherein at least one of detectable moieties $D_1$ and $D_2$ is a binding peptide selected from the group consisting of a streptavidin binding peptide and a monocytic adaptor protein (MONA) binding peptide.

12. The peptide display scaffold of claim 1, wherein at least one of detectable moieties $D_1$ and $D_2$ is a fluorescent protein.

13. The peptide display scaffold of claim 1, wherein the $D_1$ and $C_1$ moieties are located at an N-terminal domain of the fusion protein and the $D_2$ moiety is located at a C-terminal domain of the fusion protein.

14. The peptide display scaffold of claim 1, wherein the $D_1$ and $C_1$ moieties are located at a C-terminal domain of the fusion protein and the $D_2$ moiety is located at an N-terminal domain of the fusion protein.

15. The peptide display scaffold of claim 4, wherein the $C_1$ moiety comprises a member of a library of candidate peptide substrates for an enzyme.

16. The peptide display scaffold of claim 4, wherein the fusion protein comprises a linker between the $C_1$ moiety and the TM moiety and a linker between the $C_2$ moiety and the TM moiety.

17. The peptide display scaffold of claim 4, wherein at least one of detectable moieties $D_1$ and $D_2$ is an affinity tag.

18. The peptide display scaffold of claim 4, wherein at least one of detectable moieties $D_1$ and $D_2$ is a binding peptide selected from the group consisting of a streptavidin binding peptide and a monocytic adaptor protein (MONA) binding peptide.

19. The peptide display scaffold of claim 4, wherein at least one of detectable moieties $D_1$ and $D_2$ is a fluorescent protein.

20. The peptide display scaffold of claim 4, wherein the $D_1$ and $C_i$ moieties are located at an N-terminal domain of the fusion protein and the $C_2$ and $D_2$ moieties are located at a C-terminal domain of the fusion protein.

21. The peptide display scaffold of claim 4, wherein the $D_1$ and $C_i$ moieties are located at a C-terminal domain of the fusion protein and the $C_2$ and $D_2$ moieties are located at an N-terminal domain of the fusion protein.

22. The peptide display scaffold of claim 1, wherein the circularly permuted bacterial outer membrane protein is a circularly permuted OmpX.

23. The peptide display scaffold of claim 4, wherein the circularly permuted bacterial outer membrane protein is a circularly permuted OmpX.

24. The method of claim 7, wherein the circularly permuted bacterial outer membrane protein is a circularly permuted OmpX.

25. A method for identifying a peptide ligand of an enzyme, comprising:
    contacting a cell expressing a peptide display scaffold according to claim 1 with an enzyme; and
    detecting the presence or absence of a $D_1$ signal and a $D_2$ signal, wherein said detecting indicates whether $C_1$ comprises a peptide ligand for the enzyme.

* * * * *